(12) United States Patent
Borzilleri et al.

(10) Patent No.: US 9,453,048 B2
(45) Date of Patent: Sep. 27, 2016

(54) IAP ANTAGONISTS

(71) Applicant: BRISTOL-MYERS SQUIBB COMPANY, Princeton, NJ (US)

(72) Inventors: Robert M. Borzilleri, New Hope, PA (US); Heidi L. Perez, Ewing, NJ (US); Donna D. Wei, Belle Mead, NJ (US); Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 14/419,975

(22) PCT Filed: Aug. 6, 2013

(86) PCT No.: PCT/US2013/053764
§ 371 (c)(1),
(2) Date: Feb. 6, 2015

(87) PCT Pub. No.: WO2014/025759
PCT Pub. Date: Feb. 13, 2014

(65) Prior Publication Data
US 2015/0225452 A1    Aug. 13, 2015

Related U.S. Application Data

(60) Provisional application No. 61/681,277, filed on Aug. 9, 2012.

(51) Int. Cl.
| | |
|---|---|
| *A61K 38/06* | (2006.01) |
| *C07K 5/09* | (2006.01) |
| *C07D 401/12* | (2006.01) |
| *C07D 207/16* | (2006.01) |
| *C07K 5/062* | (2006.01) |
| *C07K 5/083* | (2006.01) |
| *A61K 45/06* | (2006.01) |

(52) U.S. Cl.
CPC ............ *C07K 5/0815* (2013.01); *A61K 38/06* (2013.01); *A61K 45/06* (2013.01); *C07D 207/16* (2013.01); *C07D 401/12* (2013.01); *C07K 5/06026* (2013.01); *C07K 5/0806* (2013.01)

(58) Field of Classification Search
None
See application file for complete search history.

(56) References Cited

U.S. PATENT DOCUMENTS 7,807,699 B2 * 10/2010 Hanson .............. C07D 207/16
514/359

FOREIGN PATENT DOCUMENTS

| WO | WO2007136921 A2 * | 11/2007 |
| WO | WO 2009/136290 | 11/2009 |
| WO | WO 2011/059763 | 5/2011 |
| WO | WO2011059763 A2 * | 5/2011 |
| WO | WO 2011/104266 | 9/2011 |

OTHER PUBLICATIONS

Oost, Thorsten K. et al, "Discovery of potent antagonists of the antiapoptotic protein xiap for the treatment of cancer." J. Med. Chem. (2004) 47 p. 4417-4426.*

* cited by examiner

*Primary Examiner* — Maury Audet
*Assistant Examiner* — Fred Reynolds
(74) *Attorney, Agent, or Firm* — Elliott Korsen

(57) ABSTRACT

There are disclosed compounds of formula (I) that modulate the activity of inhibitors of apoptosis (IAPs), pharmaceutical compositions containing said compounds and methods of treating proliferative disorders and disorders of dysregulated apoptosis, such as cancer, utilizing said compounds.

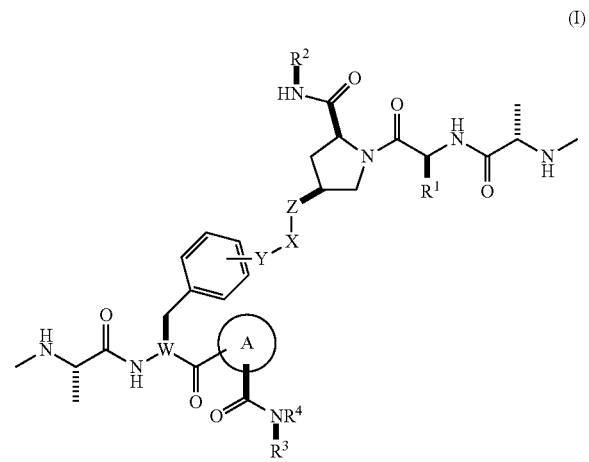

6 Claims, No Drawings

IAP ANTAGONISTS

FIELD OF THE INVENTION

The invention relates generally to compounds that modulate the activity of inhibitors of apoptosis (IAPs), pharmaceutical compositions containing said compounds and methods of treating proliferative disorders and disorders of dysregulated apoptosis, such as cancer, utilizing the compounds of the invention.

BACKGROUND OF THE INVENTION

Apoptosis or programmed cell death is a genetically and biochemically regulated mechanism that plays an important role in development and homeostasis in invertebrates as well as vertebrates.

Aberrancies in apoptosis that lead to premature cell death have been linked to a variety of developmental disorders. Deficiencies in apoptosis that result in the lack of cell death have been linked to cancer and chronic viral infections.

Caspases are cysteine-containing aspartate specific proteases that play a key role in effecting apoptosis. Once activated from their inactive zymogen form by proteolytic processing, caspases digest vital cell proteins from within the cell. Since caspases are such strong proteases, tight control of this family of proteins is necessary to prevent premature cell death. In addition to proteolytic processing, caspases are also regulated by a family of molecules known as Inhibitors of Apoptosis Proteins (IAPs). IAPs are naturally occurring intra-cellular proteins that suppress caspase-dependent apoptosis. SMAC, an intracellular protein also known as DIABLO, functions to modulate the activity of IAPs. In normal healthy cells, SMAC and IAPs function together to maintain healthy cells. However, in certain disease states, e.g., cancers and other proliferative disorders, the activities of IAPs are not adequately modulated and therefore, prevent apoptosis and cause or exacerbate abnormal proliferation and survival.

IAP antagonists, also known as SMAC mimetics, are synthetic molecules that mimic the structure and IAP modulating activity of the four N-terminal amino acids of SMAC (AVPI). When administered to a subject suffering proliferative disorders, the compounds antagonize IAP activities causing an increase in apoptosis among abnormally proliferating cells.

IAPs are found in all organisms ranging from *Drosophila* to human and are known to be overexpressed in many human cancers. IAPs comprise one to three Baculovirus IAP repeat (BIR) domains. The BIR domain is a zinc binding domain of about 70 residues comprising 4 alpha-helices and 3 beta strands, with cysteine and histidine residues that coordinate the zinc ion. The BIR 2 and 3 domains contain a conserved inhibitor of apoptosis binding motif (IBM) capable of binding caspases—and inhibiting their proteolytic activity.

As an example, human X-chromosome linked IAP (XIAP) inhibits the executioner caspases-3, and -7 as well as the Apaf-1-cytochrome C mediated activation of the initiator caspase-9. Caspases-3 and -7 are inhibited by the BIR2 domain of XIAP, while the BIR3 domain of XIAP is responsible for the inhibition of caspase-9 activation. XIAP is expressed ubiquitously in most adult and fetal tissues. Overexpression of XIAP in tumor cells has been demonstrated to confer protection of the tumor cells against a variety of pro-apoptotic stimuli and promotes resistance to chemotherapy. Consistent with this, a strong correlation between XIAP protein levels and survival has been demonstrated for patients with acute myelogenous leukemia.

Other BIR2-3 containing IAP family members, while capable of binding caspases, do not directly inhibit their proteloytic activity. Rather they inhibit apoptosis by affecting signaling activities of key proteins in cell survival pathways. Like XIAP, these IAPs possess a carboxyl-terminal RING finger domain capable of conjugating ubiquitin to specific protein substrates. As an example, cellular IAPs 1 and 2 (cIAP1/2), ubiquitinate RIPK, a signaling intermediate of tumor necrosis death receptor (TNF-DR) activation. Ubiquitinated RIPK is unable to activate caspase-8 in the context of DR activation by TNF family DR ligands. On the contrary, the long ubiquitin chains attached to RIPK provide a scaffold by which cell components of the NFkB cell survival signaling cascade can attach and become activated.

In normal cells undergoing apoptosis, the IAP-mediated inhibition is removed by the mitochondrial protein SMAC (second mitochondrial activator of caspases; also known as DIABLO). SMAC is synthesized as a precursor molecule of 239 amino acids; the N-terminal 55 residues serving as the mitochondria targeting sequence that is removed after import. The mature form of SMAC resides in the intermembrane space of mitochondria. At the time of apoptosis induction, SMAC is released from mitochondria into the cytosol where, together with cytochrome c, it binds to XIAP, and eliminates its' inhibitory effect on caspases. SMAC also binds cIAP1/2 and inhibits their ability to ubiquitinate RIPK. SMAC interacts with essentially all IAPs that have been examined to date and thus appears to be a master regulator of apoptosis in mammals.

Down-regulation of XIAP expression by antisense oligonucleotides has been shown to sensitize tumor cells to death induced by a wide range of pro-apoptotic agents, both in vitro and in vivo. SMAC/DIABLO-derived peptides have also been demonstrated to sensitize a number of different tumor induced select cell lines to undergo apoptosis as single agents, while other cell lines require an additional stimulus such as DR agonists or co-treatment with pro-apoptotic drugs. Because IAP inhibition appears to be a viable mechanism for promoting apoptosis and treating diseases and conditions that are sensitive to apoptosis, there is a continuing need to develop compounds that can inhibit IAP.

SUMMARY OF THE INVENTION

The present invention provides compounds, methods of modulating the activity of IAP, and methods for treating various medical conditions using said compounds.

The present invention also provides processes and intermediates for making the compounds of the present invention or stereoisomers, tautomers or pharmaceutically acceptable salts thereof.

The present invention also provides pharmaceutical compositions comprising a pharmaceutically acceptable carrier and one or more of the compounds of the present invention or stereoisomers, tautomers or pharmaceutically acceptable salts thereof.

The compounds of the invention may be used in the treatment and/or prophylaxis of multiple diseases or disorders associated with IAP inhibition, such as cancer and other maladies.

The compounds of the invention may be used in therapy.

The compounds of the invention may be used for the manufacture of a medicament for the treatment and/or prophylaxis of multiple diseases or disorders associated with IAP inhibition.

The compounds of the invention can be used alone, in combination with other compounds of the present invention, or in combination with one or more other agent(s).

Other features and advantages of the invention will be apparent from the following detailed description and claims.

DETAILED DESCRIPTION OF THE INVENTION

I. Compounds of the Invention

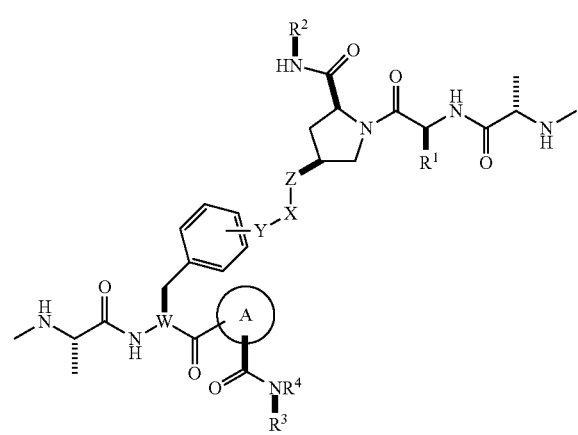

(I)

wherein

A is

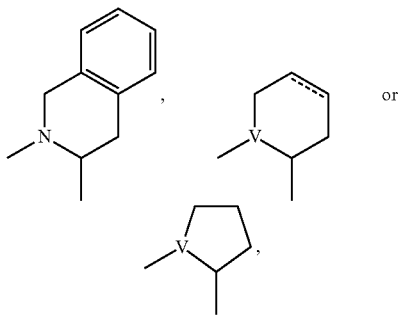

where the dotted line represents an optional double bond;

X is a —(CR$^7$R$^8$)$_m$—,

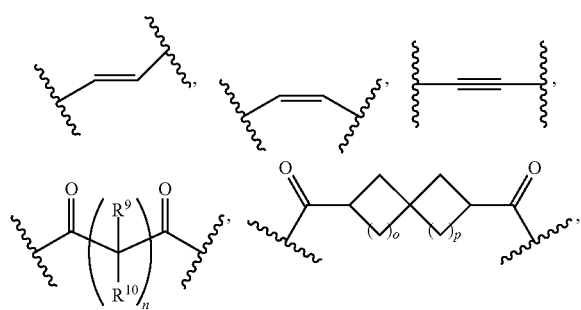

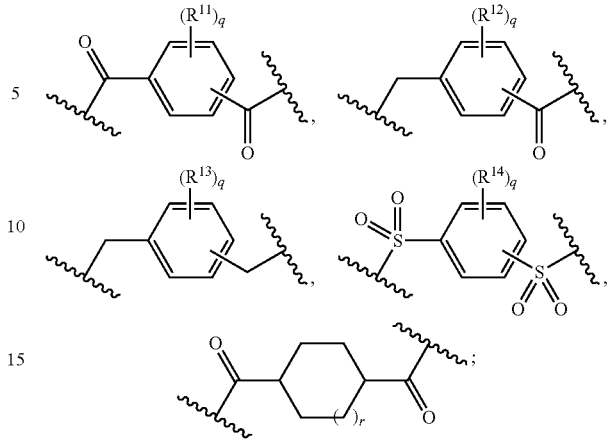

Y and Z are independently —O—, —NR$^6$— or are absent;

V is —N— or —CH—;

W is —CH— or —N—;

R$^1$ is optionally substituted alkyl, optionally substituted cycloalkyl, optionally substituted cycloalkylalkyl, optionally substituted arylalkyl or optionally substituted aryl;

R$^2$ and R$^3$ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R$^4$ is hydrogen or optionally substituted alkyl;

R$^6$ is hydrogen or optionally substituted alkyl, optionally substituted cycloalkyl;

R$^7$ and R$^8$ are independently hydrogen, halogen or optionally substituted alkyl;

R$^9$ and R$^{10}$ are independently hydrogen, halogen or optionally substituted alkyl, or R$^9$ and R$^{10}$ can be taken together to form a ring;

R$^{11}$, R$^{12}$, R$^{13}$ and R$^{14}$ are independently hydrogen, halogen, optionally substituted alkyl or OR$^{15}$;

R$^{15}$ is hydrogen, optionally substituted alkyl or optionally substituted cycloalkyl;

m and n are independently 0, 1, 2, 3, or 4;

o and p are independently 0, 1, 2 or 3;

q is 0, 1, 2, 3, or 4;

r is 0 or 1;

or a pharmaceutically acceptable salt, tautomer or stereoisomer thereof.

In a second aspect, the invention provides a compound of Formula (I) within the scope of the first aspect, wherein:

R$^1$ is optionally substituted alkyl;

R$^2$ and R$^3$ are independently optionally substituted alkyl, optionally substituted aryl or optionally substituted arylalkyl;

R$^4$ is hydrogen or alkyl;

R$^6$ is hydrogen or optionally substituted alkyl;

R$^7$ and R$^8$ are independently alkyl;

or a pharmaceutically acceptable salt, tautomer or stereoisomer thereof.

In a third aspect, the invention provides a compound of Formula (I) within the scope of the first or second aspect, wherein:

R$^1$ is alkyl;

R$^2$ and R$^3$ are independently aryl;

R⁴ is hydrogen or methyl;

or a pharmaceutically acceptable salt, tautomer or stereoisomer thereof.

In a fourth aspect, the invention provides a compound of Formula (I) within the scope of the first, second or third aspect, wherein:

R¹ is t-butyl;

R² and R³ are independently 1,2,3,4-tetrahydronaphthalene;

or a pharmaceutically acceptable salt, tautomer or stereoisomer thereof.

In a fifth aspect, the invention provides a compound of Formula (II) wherein A is

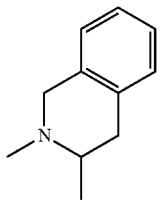

as shown below

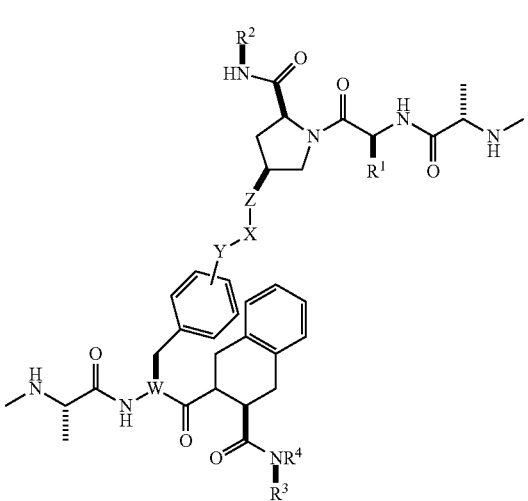

X is a —(CR⁷R⁸)ₘ—,

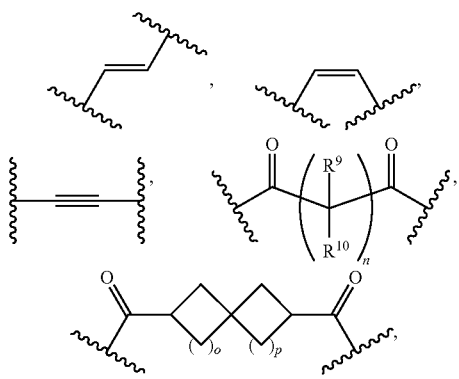

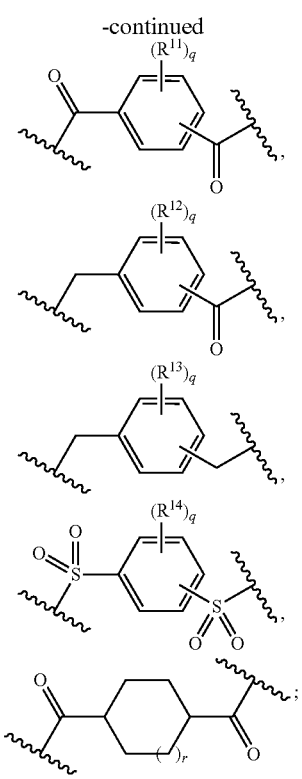

Y and Z are independently —O—, —NR⁶— or are absent;

V is —N— or —CH—;

W is —CH— or —N—;

R¹ is optionally substituted alkyl, optionally substituted cycloalkyl, optionally substituted cycloalkylalkyl, optionally substituted arylalkyl or optionally substituted aryl;

R² and R³ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;

R⁴ is hydrogen or optionally substituted alkyl;

R⁶ is hydrogen or optionally substituted alkyl, optionally substituted cycloalkyl;

R⁷ and R⁸ are independently hydrogen, halogen or optionally substituted alkyl;

R⁹ and R¹⁰ are independently hydrogen, halogen or optionally substituted alkyl, or R⁹ and R¹⁰ can be taken together to form a ring;

R¹¹, R¹², R¹³ and R¹⁴ are independently hydrogen, halogen, optionally substituted alkyl or OR¹⁵;

R¹⁵ is hydrogen, optionally substituted alkyl or optionally substituted cycloalkyl;

m and n are independently 0, 1, 2, 3, or 4;

o and p are independently 0, 1, 2 or 3;

q is 0, 1, 2, 3, or 4;

r is 0 or 1;

or a pharmaceutically acceptable salt, tautomer or stereoisomer thereof.

In a sixth aspect, the invention provides a compound of Formula (II) within the scope of the fifth aspect, wherein X is

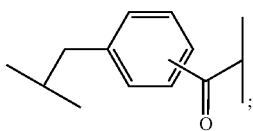

Y is —O—, —NH—, —N-alkyl or is absent, preferably —O— or —NH—;
R¹ is alkyl, preferably t-butyl;
R² and R³ are independently alkyl, aryl or arylalkyl, preferably 1,2,3,4-tetrahydronaphthalene;
R⁴ is hydrogen or alkyl, preferably hydrogen;
or a pharmaceutically acceptable salt, tautomer or stereoisomer thereof.

In a seventh aspect, the invention provides a compound of Formula (III) wherein A is

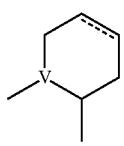

as shown below

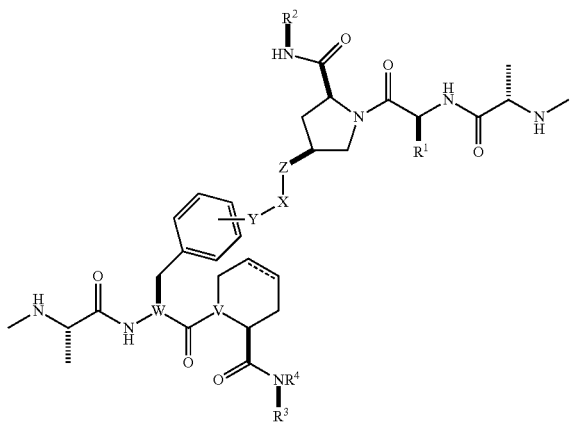

wherein
X is a —(CR⁷R⁸)$_m$—,

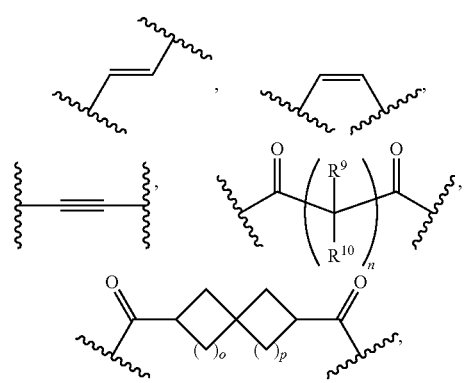

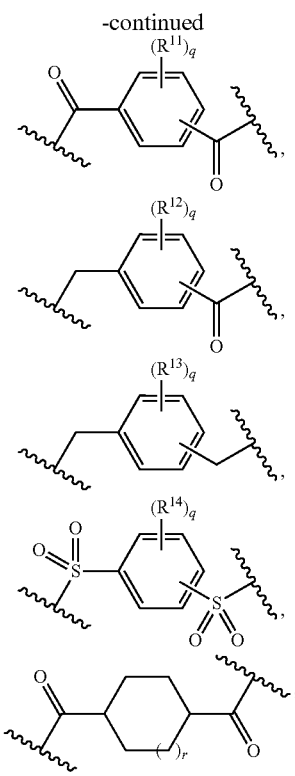

Y and Z are independently —O—, —NR⁶— or are absent;
V is —N— or —CH—;
W is —CH— or —N—;
R¹ is optionally substituted alkyl, optionally substituted cycloalkyl, optionally substituted cycloalkylalkyl, optionally substituted arylalkyl or optionally substituted aryl;
R² and R³ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;
R⁴ is hydrogen or optionally substituted alkyl;
R⁶ is hydrogen or optionally substituted alkyl, optionally substituted cycloalkyl;
R⁷ and R⁸ are independently hydrogen, halogen or optionally substituted alkyl;
R⁹ and R¹⁰ are independently hydrogen, halogen or optionally substituted alkyl, or R⁹ and R¹⁰ can be taken together to form a ring;
R¹¹, R¹², R¹³ and R¹⁴ are independently hydrogen, halogen, optionally substituted alkyl or OR¹⁵;
R¹⁵ is hydrogen, optionally substituted alkyl or optionally substituted cycloalkyl;
m and n are independently 0, 1, 2, 3, or 4;
o and p are independently 0, 1, 2 or 3;
q is 0, 1, 2, 3, or 4;
r is 0 or 1;
or a pharmaceutically acceptable salt, tautomer or stereoisomer thereof.

In an eighth aspect, the invention provides a compound of Formula (III) within the scope of the seventh aspect, wherein X is R¹ is alkyl, preferably t-butyl;
R² and R³ are independently alkyl, aryl or arylalkyl, preferably 1,2,3,4-tetrahydronaphthalene;
R⁴ is hydrogen or alkyl, preferably hydrogen;
or a pharmaceutically acceptable salt, tautomer or stereoisomer thereof.

In a ninth aspect, the invention provides a compound of Formula (IV) wherein A is as shown below (IV)

wherein
X is a —(CR⁷R⁸)$_m$—,

Y and Z are independently —O—, —NR⁶— or are absent;
V is —N— or —CH—;
W is —CH— or —N—;
R¹ is optionally substituted alkyl, optionally substituted cycloalkyl, optionally substituted cycloalkylalkyl, optionally substituted arylalkyl or optionally substituted aryl;
R² and R³ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl;
R⁴ is hydrogen or optionally substituted alkyl;
R⁶ is hydrogen or optionally substituted alkyl, optionally substituted cycloalkyl;
R⁷ and R⁸ are independently hydrogen, halogen or optionally substituted alkyl;
R⁹ and R¹⁰ are independently hydrogen, halogen or optionally substituted alkyl, or R⁹ and R¹⁰ can be taken together to form a ring;
R¹¹, R¹², R¹³ and R¹⁴ are independently hydrogen, halogen, optionally substituted alkyl or OR¹⁵;
R¹⁵ is hydrogen, optionally substituted alkyl or optionally substituted cycloalkyl;
m and n are independently 0, 1, 2, 3, or 4;
o and p are independently 0, 1, 2 or 3;
q is 0, 1, 2, 3, or 4;
r is 0 or 1;
or a pharmaceutically acceptable salt, tautomer or stereoisomer thereof.

In a tenth aspect, the invention provides a compound of Formula (IV) within the scope of the ninth aspect, wherein X is R¹ is alkyl, preferably t-butyl;
R² and R³ are independently alkyl, aryl or arylalkyl, preferably 1,2,3,4-tetrahydronaphthalene;
R⁴ is hydrogen or alkyl, preferably hydrogen;

or a pharmaceutically acceptable salt, tautomer or stereoisomer thereof.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In one embodiment, Y is a direct bond, —O—. —NH— or —CONH—.

In another embodiment, Y is a direct bond or —CONH—.

In another embodiment, Y is a direct bond.

In another embodiment, Z is —CONH—.

In another embodiment, $R^1$ is t-butyl.

In another embodiment, $R^2$ and $R^3$ are independently 1,2,3,4-tetrahydronaphthalenyl.

In another embodiment, $R^4$ is hydrogen or methyl.

In another embodiment, $R^{12}$ is fluoro or chloro.

In another aspect, the invention provides a compound selected from the exemplified examples within the scope of the first aspect, or a pharmaceutically acceptable salt, tautomer or stereoisomer thereof.

In another aspect, the invention provides a compound selected from any subset list of compounds within the scope of any of the above aspects.

In another embodiment, the compounds of the invention have BIR3 $IC_{50}$ values≤0.40.

In another embodiment, the compounds of the invention have BIR3 $IC_{50}$ values≤0.20.

In another embodiment, the compounds of the invention have BIR3 $IC_{50}$ values≤0.10.

In another embodiment, the compounds of the invention have BIR3 $IC_{50}$ values≤0.05.

In another embodiment, the compounds of the invention have BIR2-3 $IC_{50}$ values≤3.00.

In another embodiment, the compounds of the invention have BIR2-3 $IC_{50}$ values≤2.00.

In another embodiment, the compounds of the invention have BIR2-3 $IC_{50}$ values≤1.00.

In another embodiment, the compounds of the invention have BIR2-3 $IC_{50}$ values≤0.50.

II. Other Embodiments of the Invention

In another embodiment, the present invention provides a composition comprising one or more compounds of the present invention or a stereoisomer, a tautomer, a pharmaceutically acceptable salt, or a solvate thereof In another embodiment, the present invention provides a pharmaceutical composition comprising a pharmaceutically acceptable carrier and at least one of the compounds of the present invention or a stereoisomer, a tautomer, a pharmaceutically acceptable salt, or a solvate thereof.

In another embodiment, the present invention provides a pharmaceutical composition, comprising: a pharmaceutically acceptable carrier and a therapeutically effective amount of at least one of the compounds of the present invention or a stereoisomer, a tautomer, a pharmaceutically acceptable salt, or a solvate thereof.

In another embodiment, the present invention provides a process for making a compound of the present invention or a stereoisomer, a tautomer, a pharmaceutically acceptable salt, or a solvate thereof.

In another embodiment, the present invention provides an intermediate for making a compound of the present invention or a stereoisomer, a tautomer, a pharmaceutically acceptable salt, or a solvate thereof.

In another embodiment, the present invention provides a method for the treatment and/or prophylaxis of various types of cancer, comprising administering to a patient in need of such treatment and/or prophylaxis a therapeutically effective amount of one or more compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment and/or prophylaxis of multiple diseases or disorders associated with the inhibition of apoptosis.

In another aspect, the invention provides a method of treating a patient suffering from or susceptible to a medical condition that is sensitive to apoptosis. A number of medical conditions can be treated. The method comprises administering to the patient a therapeutically effective amount of a composition comprising a compound described herein. For example, the compounds described herein may be used to treat or prevent infections, proliferative diseases (e.g., cancer), and autoimmune diseases.

In another aspect, the invention provides a method of inhibiting the activity of an IAP in a cell, thus promoting apoptosis. The method comprises exposing the cell to a compound described herein.

III. Therapeutic Applications

The compounds and pharmaceutical compositions of the present invention are useful in treating or preventing any disease or conditions that are sensitive to apoptosis. These include infections (e.g., skin infections, GI infection, urinary tract infections, genitourinary infections, systemic infections), proliferative diseases (e.g., cancer), and autoimmune diseases (e.g., rheumatoid arthritis, lupus). The compounds and pharmaceutical compositions may be administered to animals, preferably mammals (e.g., domesticated animals, cats, dogs, mice, rats), and more preferably humans. Any method of administration may be used to deliver the compound or pharmaceutical composition to the animal. In certain embodiments, the compound or pharmaceutical composition is administered orally. In other embodiments, the compound or pharmaceutical composition is administered parenterally.

In one embodiment, the compounds of this invention can be used for the treatment of any cancer type that fails to undergo apoptosis in a patient. This includes, but is not limited to: solid tumors, including but not limited to carcinomas; sarcomas including Kaposi's sarcoma; erythroblastoma; glioblastoma; meningioma; astrocytoma; melanoma; and myoblastoma. Treatment or prevention of non-solid tumor cancers, such as leukemia, is also contemplated by this invention.

Types of cancers that may be treated with the compounds of this invention include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tong carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

In addition to apoptosis defects found in tumors, defects in the ability to eliminate self-reactive cells of the immune system due to apoptosis resistance are considered to play a key role in the pathogenesis of autoimmune diseases. Autoimmune diseases are characterized in that the cells of the immune system produce antibodies against its own organs and molecules or directly attack tissues resulting in the destruction of the latter. A failure of those self-reactive cells to undergo apoptosis leads to the manifestation of the disease. Defects in apoptosis regulation have been identified in autoimmune diseases such as systemic lupus erythematosus or rheumatoid arthritis.

Thus, according to another embodiment, the invention provides a method of treating an autoimmune disease by providing to a patient in need thereof a compound or composition of the present invention. Examples of such autoimmune diseases include, but are not limited to, collagen diseases such as rheumatoid arthritis, systemic lupus erythematosus. Sharp's syndrome, CREST syndrome (calcinosis, Raynaud's syndrome, esophageal dysmotility, telangiectasia), dermatomyositis, vasculitis (Morbus Wegener's) and Sjögren's syndrome, renal diseases such as Goodpasture's syndrome, rapidly-progressing glomerulonephritis and membrano-proliferative glomerulonephritis type II, endocrine diseases such as type-I diabetes, autoimmune polyendocrinopathy-candidiasis-ectodermal dystrophy (APECED), autoimmune parathyroidism, pernicious anemia, gonad insufficiency, idiopathic Morbus Addison's, hyperthyreosis, Hashimoto's thyroiditis and primary myxedema, skin diseases such as *pemphigus vulgaris*, bullous pemphigoid, herpes gestationis, epidermolysis bullosa and erythema multiforme major, liver diseases such as primary biliary cirrhosis, autoimmune cholangitis, autoimmune hepatitis type-1, autoimmune hepatitis type-2, primary sclerosing cholangitis, neuronal diseases such as multiple sclerosis, myasthenia gravis, myasthenic Lambert-Eaton syndrome, acquired neuromyotomy, Guillain-Barre syndrome (Muller-Fischer syndrome), stiff-man syndrome, cerebellar degeneration, ataxia, opsoclonus, sensoric neuropathy and achalasia, blood diseases such as autoimmune hemolytic anemia, idiopathic thrombocytopenic purpura (Morbus Werlhof), infectious diseases with associated autoimmune reactions such as AIDS, Malaria and Chagas disease.

Compounds of the invention are useful for sensitizing cells to apoptotic signals. Thus, in one embodiment, the compounds of the invention are co-administered with radiation therapy or a second therapeutic agent with cytostatic or antineoplastic activity. Suitable cytostatic chemotherapy compounds include, but are not limited to (i) antimetabolites; (ii) DNA-fragmenting agents, (iii) DNA-crosslinking agents, (iv) intercalating agents (v) protein synthesis inhibitors, (vi) topoisomerase I poisons, such as camptothecin or topotecan; (vii) topoisomerase II poisons, (viii) microtubule-directed agents, (ix) kinase inhibitors (x) miscellaneous investigational agents (xi) hormones and (xii) hormone antagonists. It is contemplated that compounds of the invention may be useful in combination with any known agents falling into the above 12 classes as well as any future agents that are currently in development. In particular, it is contemplated that compounds of the invention may be useful in combination with current Standards of Care as well as any that evolve over the foreseeable future. Specific dosages and dosing regimens would be based on physicians' evolving knowledge and the general skill in the art.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

IV. Pharmaceutical Compositions and Dosing

The invention also provides pharmaceutically acceptable compositions which comprise a therapeutically effective amount of one or more of the compounds of Formula I, formulated together with one or more pharmaceutically acceptable carriers (additives) and/or diluents, and optionally, one or more additional therapeutic agents described above. As described in detail below, the pharmaceutical compositions of the present invention may be specially formulated for administration in solid or liquid form, including those adapted for the following: (1) oral administration, for example, drenches (aqueous or nonaqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained release formulation; (3) topical application, for example, as a cream, ointment, or a controlled release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, troches and the like), the active ingredient is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or non-aqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Injectable depot forms are made by forming microencapsuled matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

V. Definitions

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C=C double bonds, C=N double bonds, ring systems, and the like can also be present in the compounds, and all such stable isomers are contemplated in the present invention. Cis- and trans- (or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained either in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

As used herein, the term "alkyl" or "alkylene" is intended to include both branched and straight-chain saturated aliphatic hydrocarbon groups having the specified number of carbon atoms. For example, "$C_1$-$C_6$ alkyl" denotes alkyl having 1 to 6 carbon atoms. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl).

The term "alkoxy" or "alkyloxy" refers to an —O-alkyl group. "$C_{1-6}$ alkoxy" (or alkyloxy), is intended to include $C_1$, $C_2$, $C_3$, $C_4$, $C_5$, and $C_6$ alkoxy groups. Example alkoxy groups include, but are not limited to, methoxy, ethoxy, propoxy (e.g., n-propoxy and isopropoxy), and t-butoxy. Similarly, "alkylthio" or "thioalkoxy" represents an alkyl group as defined above with the indicated number of carbon atoms attached through a sulphur bridge; for example methyl-S— and ethyl-S—.

The term "aryl", either alone or in combination with another radical, means a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, 1-naphthyl, 2-naphthyl and tetrahydronaphthyl. The fused aryls may be connected to another group either at a suitable position on the cycloalkyl ring or the aromatic ring. For example:

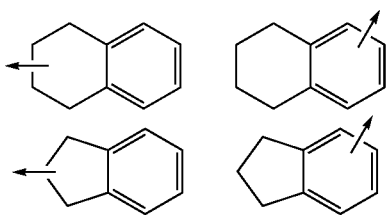

Arrowed lines drawn from the ring system indicate that the bond may be attached to any of the suitable ring atoms.

The term "cycloalkyl" refers to cyclized alkyl groups. $C_{3-6}$ cycloalkyl is intended to include $C_3$, $C_4$, $C_5$, and $C_6$ cycloalkyl groups. Example cycloalkyl groups include, but are not limited to, cyclopropyl, cyclobutyl, cyclopentyl, cyclohexyl, and norbornyl. Branched cycloalkyl groups such as 1-methylcyclopropyl and 2-methylcyclopropyl are included in the definition of "cycloalkyl". The term "cycloalkenyl" refers to cyclized alkenyl groups. $C_{4-6}$ cycloalkenyl is intended to include $C_4$, $C_5$, and $C_6$ cycloalkenyl groups. Example cycloalkenyl groups include, but are not limited to, cyclobutenyl, cyclopentenyl, and cyclohexenyl.

"Halo" or "halogen" includes fluoro, chloro, bromo, and iodo. "Haloalkyl" is intended to include both branched and straight-chain saturated aliphatic hydrocarbon groups having the specified number of carbon atoms, substituted with 1 or more halogens.

Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" that is intended to include both branched and straight-chain saturated aliphatic hydrocarbon groups having the specified number of carbon atoms, substituted with 1 or more fluorine atoms.

"Haloalkoxy" or "haloalkyloxy" represents a haloalkyl group as defined above with the indicated number of carbon atoms attached through an oxygen bridge. For example, "$C_{1-6}$ haloalkoxy", is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluorothoxy. Similarly, "haloalkylthio" or "thiohaloalkoxy" represents a haloalkyl group as defined above with the indicated number of carbon atoms attached through a sulphur bridge; for example trifluoromethyl-S—, and pentafluoroethyl-S—.

As used herein, the term "heteroaryl" or "aromatic heterocyclic group" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., N or NR wherein R is H or another substituent, if defined). The nitrogen and sulfur heteroatoms may optionally be oxidized (i.e., N→O and $S(O)_p$, wherein p is 0, 1 or 2).

As used herein, the term "heterocyclo", "heterocyclic" or "heterocyclyl" is intended to mean a 5-, 6- or 7-membered non-aromatic ring system containing from 1 to 4 heteroatoms selected from O, N or S. Examples of heterocycles include, but are not limited to, pyrrolidinyl, tetrahydrofuranyl, tetrahydropyranyl, piperidyl, pyrrolinyl, piperazinyl, imidazolinyl, morpholinyl, imidazolidinyl, pyrazolidinyl and pyrazolinyl.

The term "counter ion" is used to represent a negatively charged species such as chloride, bromide, hydroxide, acetate, and sulfate or a positively charged species such as sodium (Na+), potassium (K+), ammonium ($R_nNH_m+$ where n=0-4 and m=0-4) and the like.

The term "electron withdrawing group" (EWG) refers to a substituent which polarizes a bond, drawing electron density towards itself and away from other bonded atoms. Examples of EWG include, but are not limited to, $CF_3$, $CF_2CF_3$, CN, halogen, haloalkyl, $NO_2$, sulfone, sulfoxide, ester, sulfonamide, carboxamide, alkoxy, alkoxyether, alkenyl, alkynyl, OH, C(O)alkyl, $CO_2H$, phenyl, heteroaryl, —O-phenyl, and —O— heteroaryl. Preferred examples of EWG include, but are not limited to, $CF_3$, $CF_2CF_3$, CN, halogen, $SO_2(C_{1-4}$ alkyl), $CONH(C_{1-4}$ alkyl), $CON(C_{1-4}$ alkyl$)_2$, and heteroaryl. More preferred examples of EWG include, but are not limited to, $CF_3$ and CN.

As used herein, the term "amine protecting group" means any group known in the art of organic synthesis for the protection of amine groups which is stable to an ester reducing agent, a di-substituted hydrazine, a nucleophile, a hydrazine reducing agent, an activator, a strong base, a hindered amine base and a cyclizing agent. Such amine protecting groups fitting these criteria include those listed in Greene et al., *Protective Groups in Organic Synthesis*, John Wiley & Sons, New York (1991) and *The Peptides: Analysis, Synthesis, Biology*, Vol. 3, Academic Press, New York (1981), the disclosure of which is hereby incorporated by reference. Examples of amine protecting groups include, but are not limited to, the following: (1) acyl types such as formyl, trifluoroacetyl, phthalyl, and p-toluenesulfonyl; (2) aromatic carbamate types such as benzyloxycarbonyl (Cbz) and substituted benzyloxycarbonyls, 1-(p-biphenyl)-1-methylethoxycarbonyl, and 9-fluorenylmethyloxycarbonyl (Fmoc); (3) aliphatic carbamate types such as tert-butyloxycarbonyl (Boc), ethoxycarbonyl, diisopropylmethoxycarbonyl, and allyloxycarbonyl; (4) cyclic alkyl carbamate types such as cyclopentyloxycarbonyl and adamantyloxycarbonyl; (5) alkyl types such as triphenylmethyl and benzyl; (6) trialkylsilane such as trimethylsilane; (7) thiol containing types such as phenylthiocarbonyl and dithiasuccinoyl; and (8) alkyl types such as triphenylmethyl, methyl, and benzyl; and substituted alkyl types such as 2,2,2-trichloroethyl, 2-phenylethyl, and t-butyl; and trialkylsilane types such as trimethylsilane.

As referred to herein, the term "substituted" means that at least one hydrogen atom is replaced with a non-hydrogen group, provided that normal valencies are maintained and that the substitution results in a stable compound. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→O) derivative.

When any variable occurs more than one time in any constituent or formula for a compound, its definition at each occurrence is independent of its definition at every other occurrence. Thus, for example, if a group is shown to be substituted with 0-3 R, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The phrase "pharmaceutically acceptable" is employed herein to refer to those compounds, materials, compositions, and/or dosage forms that are, within the scope of sound medical judgment, suitable for use in contact with the tissues of human beings and animals without excessive toxicity, irritation, allergic response, and/or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic groups such as amines; and alkali or organic salts of acidic groups such as carboxylic acids. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, and nitric; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, and isethionic, and the like.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 18th Edition, Mack Publishing Company, Easton, Pa. (1990), the disclosure of which is hereby incorporated by reference.

In addition, compounds of formula I may have prodrug forms. Any compound that will be converted in vivo to provide the bioactive agent (i.e., a compound of formula I) is a prodrug within the scope and spirit of the invention. Various forms of prodrugs are well known in the art. For examples of such prodrugs derivatives, see:

a) Bundgaard, H., ed., *Design of Prodrugs*, Elsevier (1985), and Widder, K. et al., eds., *Methods in Enzymology*, 112:309-396, Academic Press (1985);

b) Bundgaard, H., Chapter 5, "Design and Application of Prodrugs", Krosgaard-Larsen, P. et al., eds., *A Textbook of Drug Design and Development*, pp. 113-191, Harwood Academic Publishers (1991);

c) Bundgaard, H., Adv. *Drug Deliv. Rev.*, 8:1-38 (1992);

d) Bundgaard, H. et al., *J. Pharm. Sci.*, 77:285 (1988); and e) Kakeya, N. et al., *Chem. Pharm. Bull.*, 32:692 (1984).

Compounds containing a carboxy group can form physiologically hydrolyzable esters that serve as prodrugs by being hydrolyzed in the body to yield formula I compounds per se. Such prodrugs are preferably administered orally since hydrolysis in many instances occurs principally under the influence of the digestive enzymes. Parenteral administration may be used where the ester per se is active, or in those instances where hydrolysis occurs in the blood. Examples of physiologically hydrolyzable esters of compounds of formula I include $C_{1-6}$alkyl, $C_{1-6}$alkylbenzyl, 4-methoxybenzyl, indanyl, phthalyl, methoxymethyl, $C_{1-6}$ alkanoyloxy-$C_{1-6}$alkyl (e.g., acetoxymethyl, pivaloyloxymethyl or propionyloxymethyl), $C_{1-6}$alkoxycarbonyloxy-$C_{1-6}$alkyl (e.g., methoxycarbonyl-oxymethyl or ethoxycarbonyloxymethyl, glycyloxymethyl, phenylglycyloxymethyl, (5-methyl-2-oxo-1,3-dioxolen-4-yl)-methyl), and other well known physiologically hydrolyzable esters used, for example, in the penicillin and cephalosporin arts. Such esters may be prepared by conventional techniques known in the art.

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, Calif. (1999).

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

The term "solvate" means a physical association of a compound of this invention with one or more solvent molecules, whether organic or inorganic. This physical association includes hydrogen bonding. In certain instances the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. "Solvate" encompasses both solution-phase and isolable solvates. Exemplary solvates include, but are not limited to, hydrates, ethanolates, methanolates, and isopropanolates. Methods of solvation are generally known in the art.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "therapeutically effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

Compounds of the invention may be prepared according to the general routes illustrated in Schemes 1 to 8. Tautomers and solvates (e.g., hydrates) of the compounds are also within the scope of the present invention. Methods of solvation are generally known in the art. Accordingly, the compounds of the instant invention may be in the free or hydrate form, and may be obtained by methods exemplified by the following Schemes.

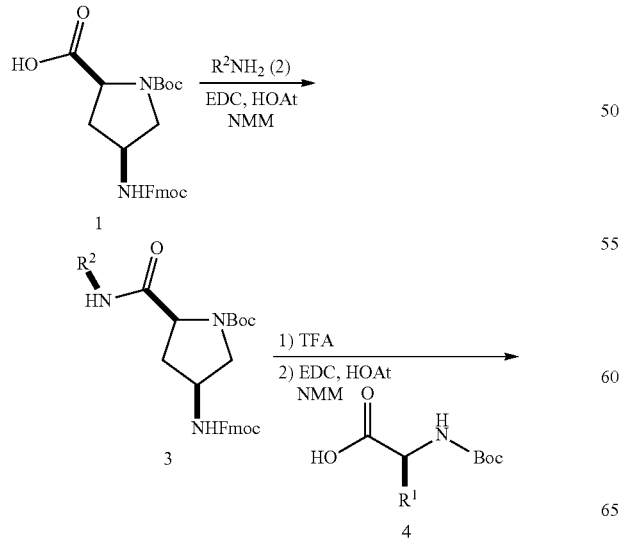

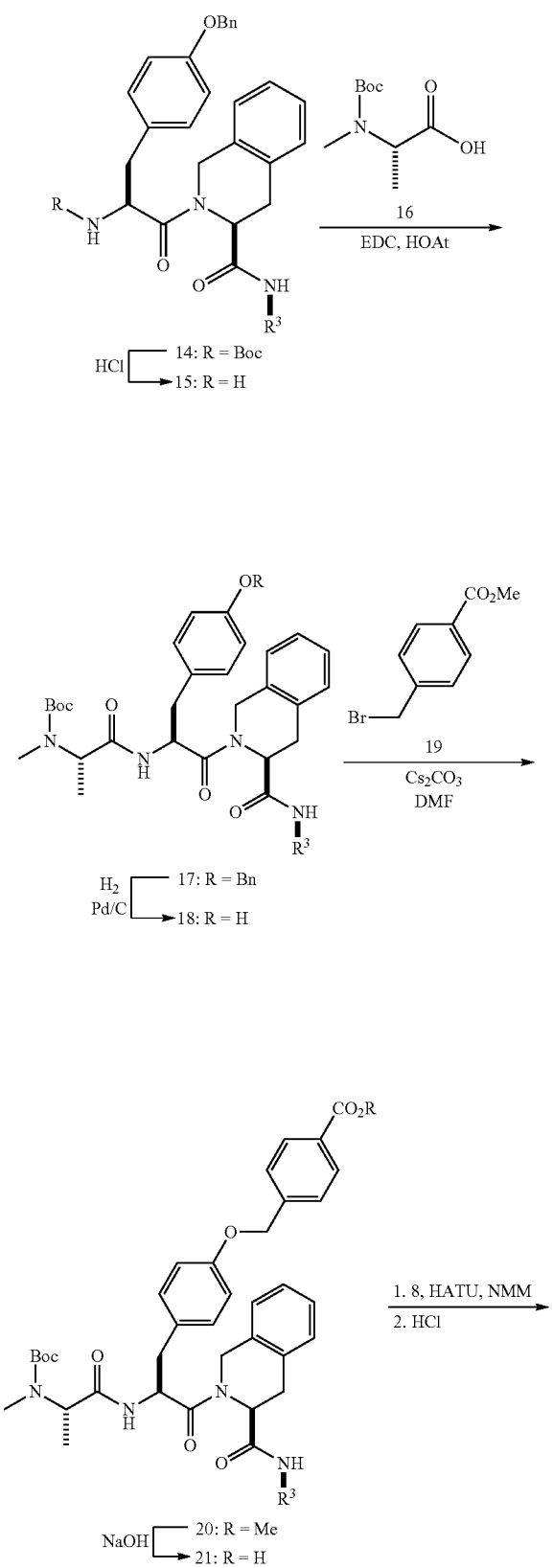

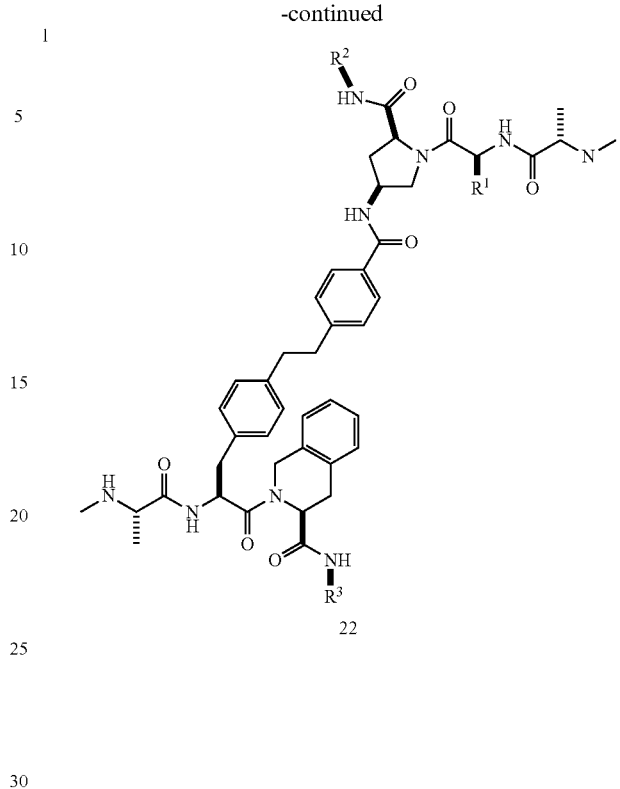

Heterodimeric analogues 22 can be prepared using the chemistry outlined above in Scheme 1. Key peptide intermediate 8 can be derived from commercially available (2S,4S)-Boc-gamma-(Fmoc-amino)-proline (1) using straightforward chemistry. Specifically, proline acid 1 can be converted to amide 3 by employing primary amines 2 and coupling reagents, such as EDC-HOAt. Removal of the N-Boc protecting group of 3 under acidic conditions, followed by coupling of the secondary amine with the N-Boc amino acid 4 can furnish 5. Removal of the N-Boc group of intermediate 5, followed by coupling with N-Boc amino acid 6 afforded compound 7. Removal of the N-Fmoc group of 7 with piperidine provided peptide intermediate 8. The lower half of compound 22 can be derived from commercially available tetrahydroisoquinoline (THIQ) carboxylic acid 9. Thus, compound 9 can be converted to amide 11 using primary amines 10 and coupling reagents, such as EDC-HOAt. Removal of the N-Boc protecting group of 11 under acidic conditions, followed by coupling with the N-Boc amino acid 13 can furnish 14. Removal of the N-Boc group of intermediate 14, followed by coupling with N-Boc amino acid 16 gave derivative 17. Phenol 18, derived from benzyl ether 17, can be coupled with methyl 4-(bromomethyl)benzoate (19) under basic conditions to provide compound 20. Base-promoted hydrolysis of ester 20 led to carboxylic acid 21. Subsequent coupling of compound 21 to intermediate 8, followed by global deprotection provided the desired analogues 22.

Scheme 2

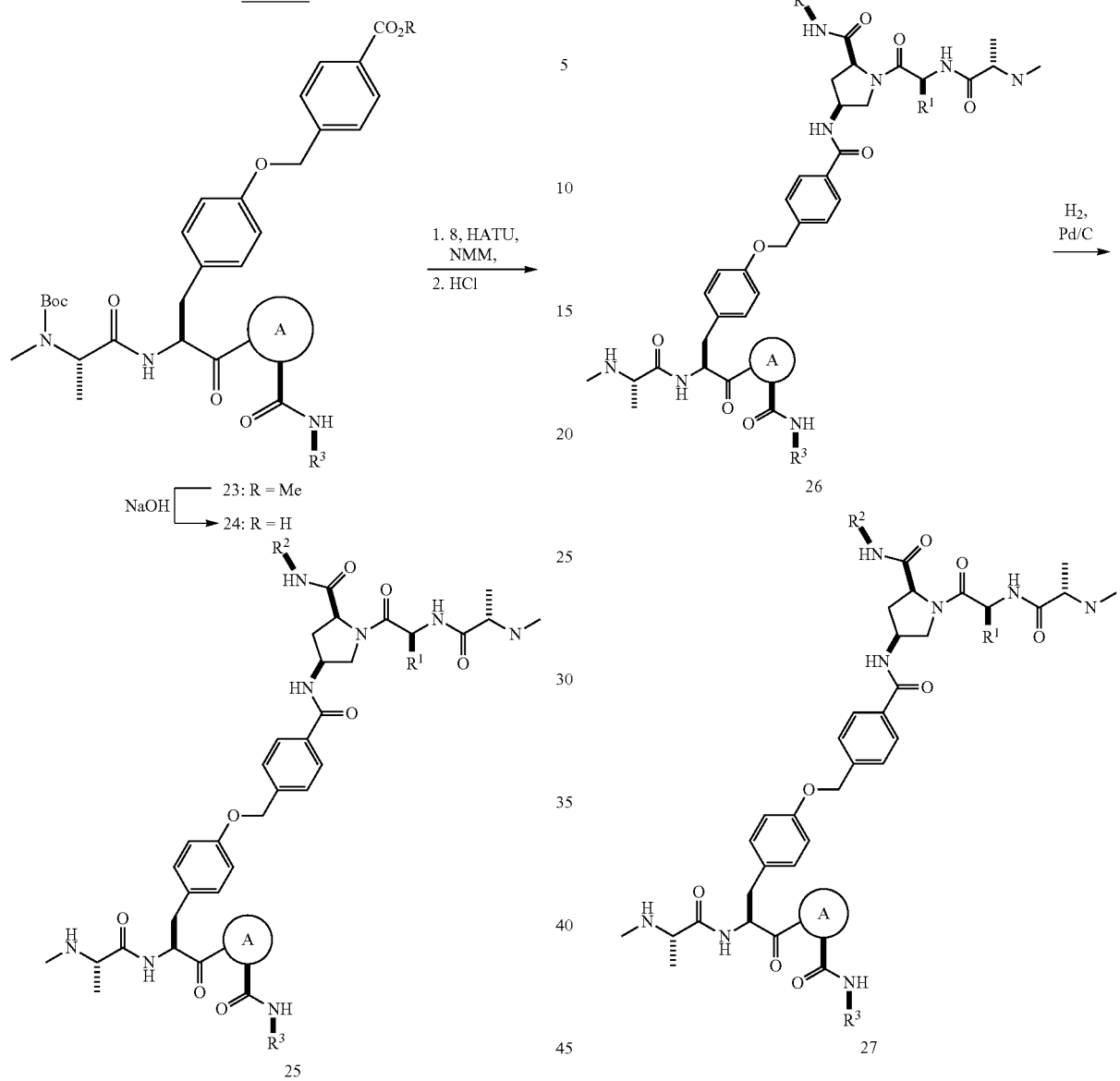

For example:

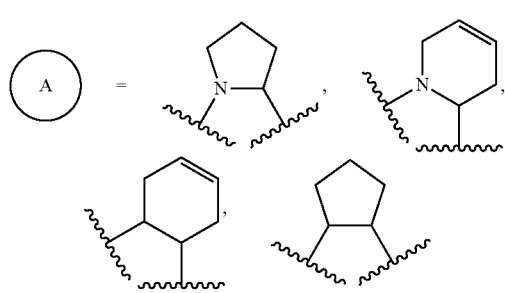

Dimeric analogues 25 (with A groups other than THIQ) can be obtained in a similar manner according to Scheme 2. Hydrolysis of ester 23 with for example, sodium hydroxide afforded the carboxylic acid 24. Subsequent coupling of compound 24 with amine 8, followed by global deprotection with acid provided the desired analogues 25.

For example:

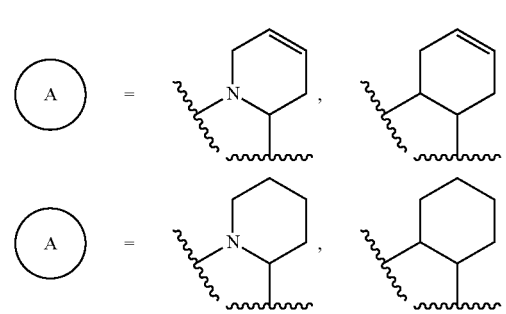

Compounds with double bonds embedded within the A group can be reduced to provide analogues 27 (Scheme 3). For example, hydrogenation of 26 afforded the desired analogues 27.

Scheme 4
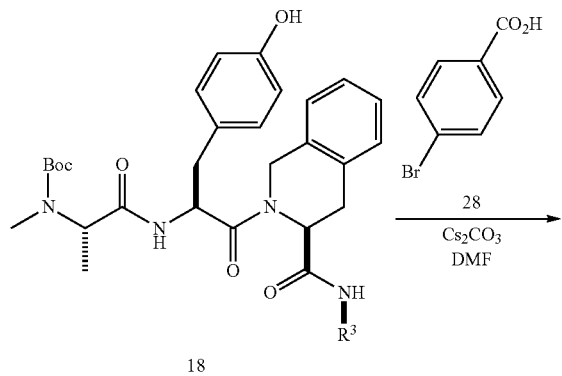
18
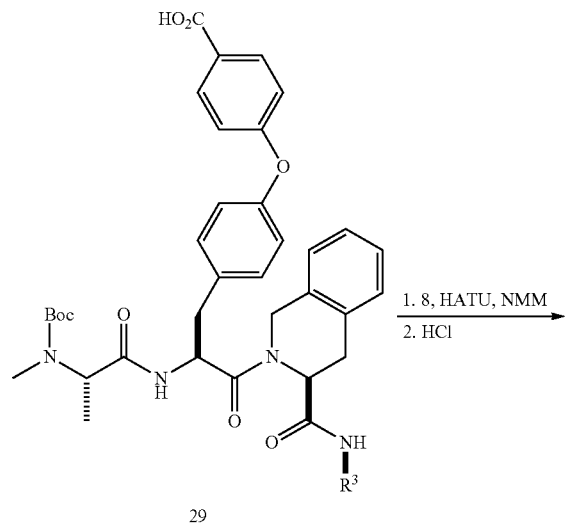
29
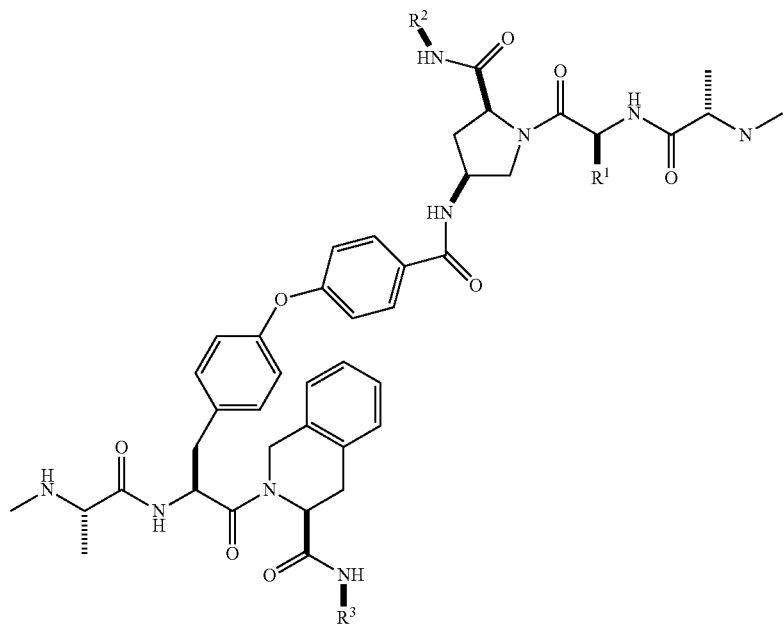
30

Biaryl ether analogues 30 can be prepared according to the synthetic route shown above in Scheme 4. The benzoic acid intermediate 29, derived from tyrosine derivative 18 and 4-bromobenzoic acid (28) can be coupled to amine 8 and subsequently treated with acid to furnish 30.

Scheme 5

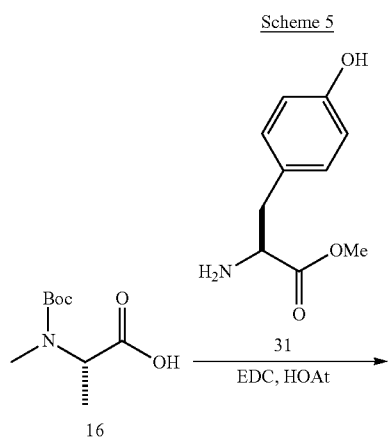

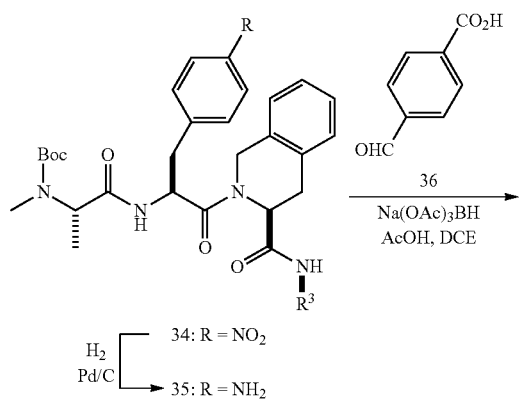

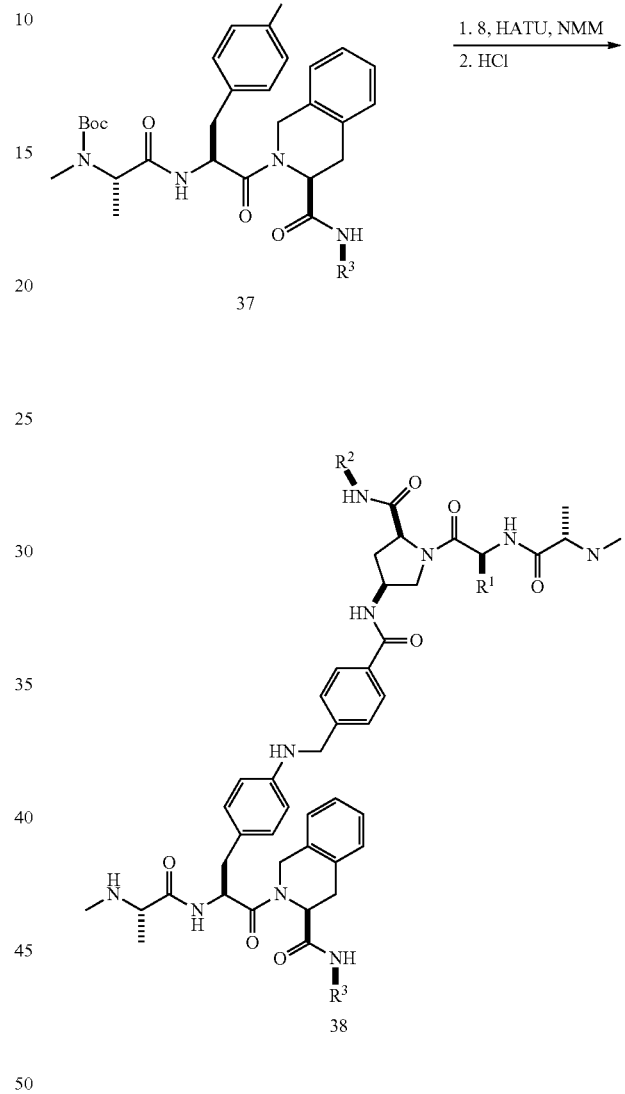

Heterodimeric analogues 38 can be prepared according to the synthetic route outlined above in Scheme 5. Commercially available (S)-2-((tert-butoxycarbonyl)(methyl)amino)propanoic acid (16) can be coupled to amino acid 31 using standard peptide coupling reagents (e.g., EDC-HOAt). Base-promoted hydrolysis of ester 32 and subsequent coupling of the requisite acid 33 with secondary amine 12 afforded the peptide 34. Chemoselective reduction of the nitro group of 34 under hydrogenation conditions, followed by reductive alkylation of aniline 35 with 4-formylbenzoic acid (36) provided intermediate 37. Coupling of acid 37 with intermediate 8, followed by global deprotection gave the desired analogues.

35

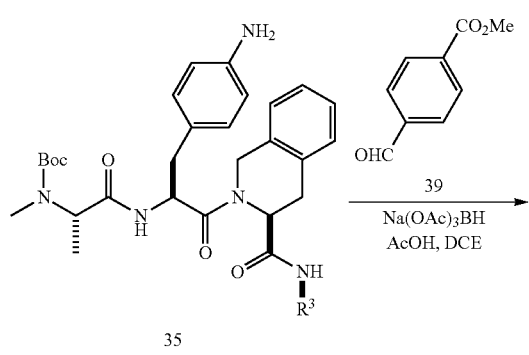

35

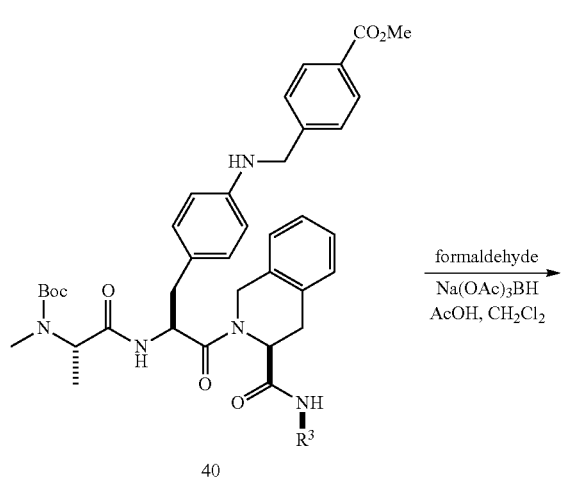

40

41: R = Me
42: R = H

36

-continued

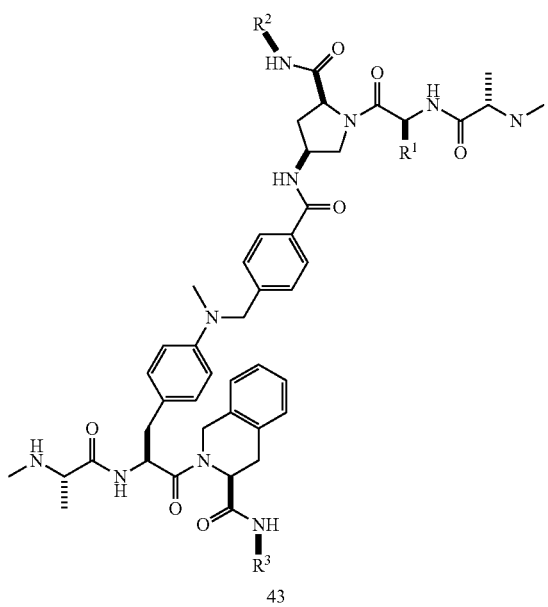

43

The N-methyl analogues 43 can be prepared according to the synthetic route outlined above in Scheme 6. Reductive alkylation of aniline 35 and methyl 4-formylbenzoate (39) with sodium triacetoxyborohydride in the presence of acetic acid provided intermediate 40. A subsequent reductive alkylation reaction between aniline 40 and formaldehyde gave intermediate 41. Compounds 41 were converted to the desired analogues 43 using chemistry previously described.

Scheme 7

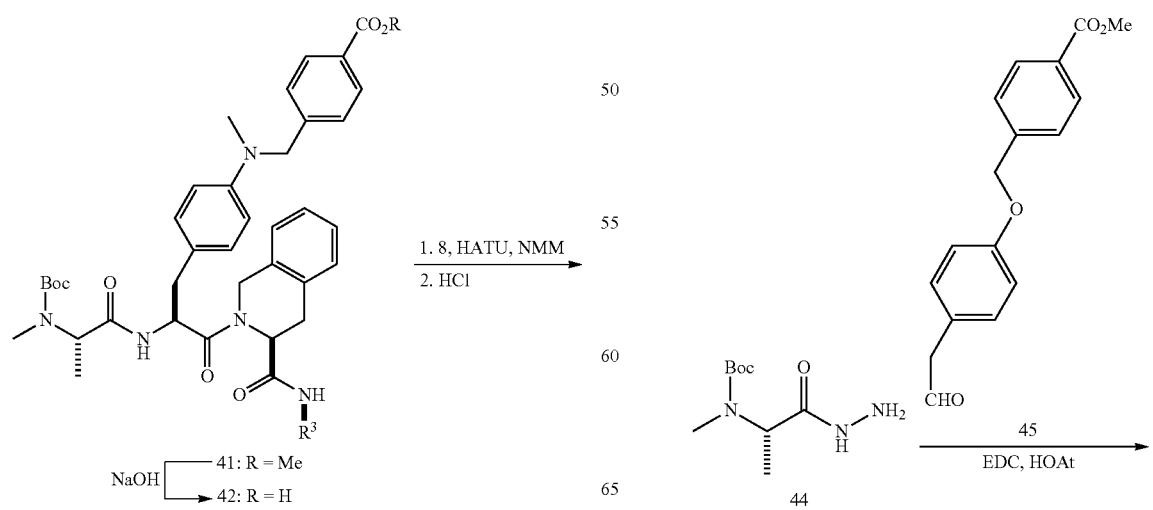

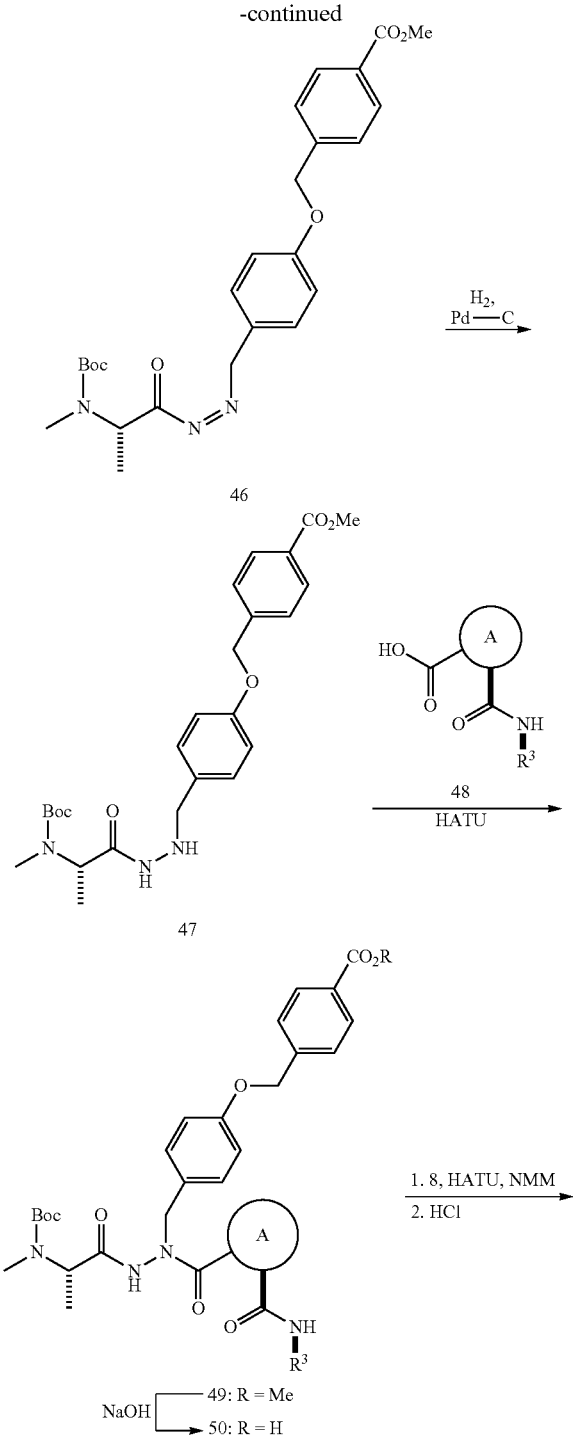
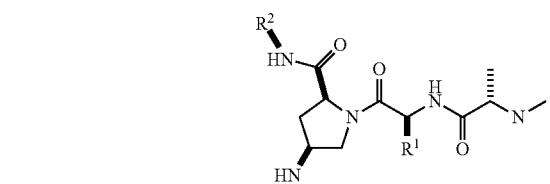
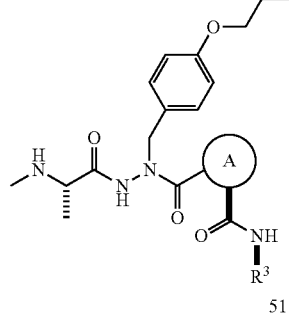

Heterodimeric ether analogues 51 can be prepared using the synthetic sequence shown above in Scheme 7. Hydrazide intermediate 44, derived from commercially available (S)-2-((tert-butoxycarbonyl)(methyl)amino)propanoic acid (16) and hydrazine, can undergo a reductive alkylation reaction with methyl 4-((4-(2-oxoethyl)phenoxy)methyl)benzoate (45) to afford compound 46. Reduction of diazene derivative 46, followed by the coupling of the requisite hydrazide 47 with acid 48 using for example, HATU provided intermediate 49. Compound 49 can be converted to the desired analogues 51 using chemistry previously described.

Scheme 8
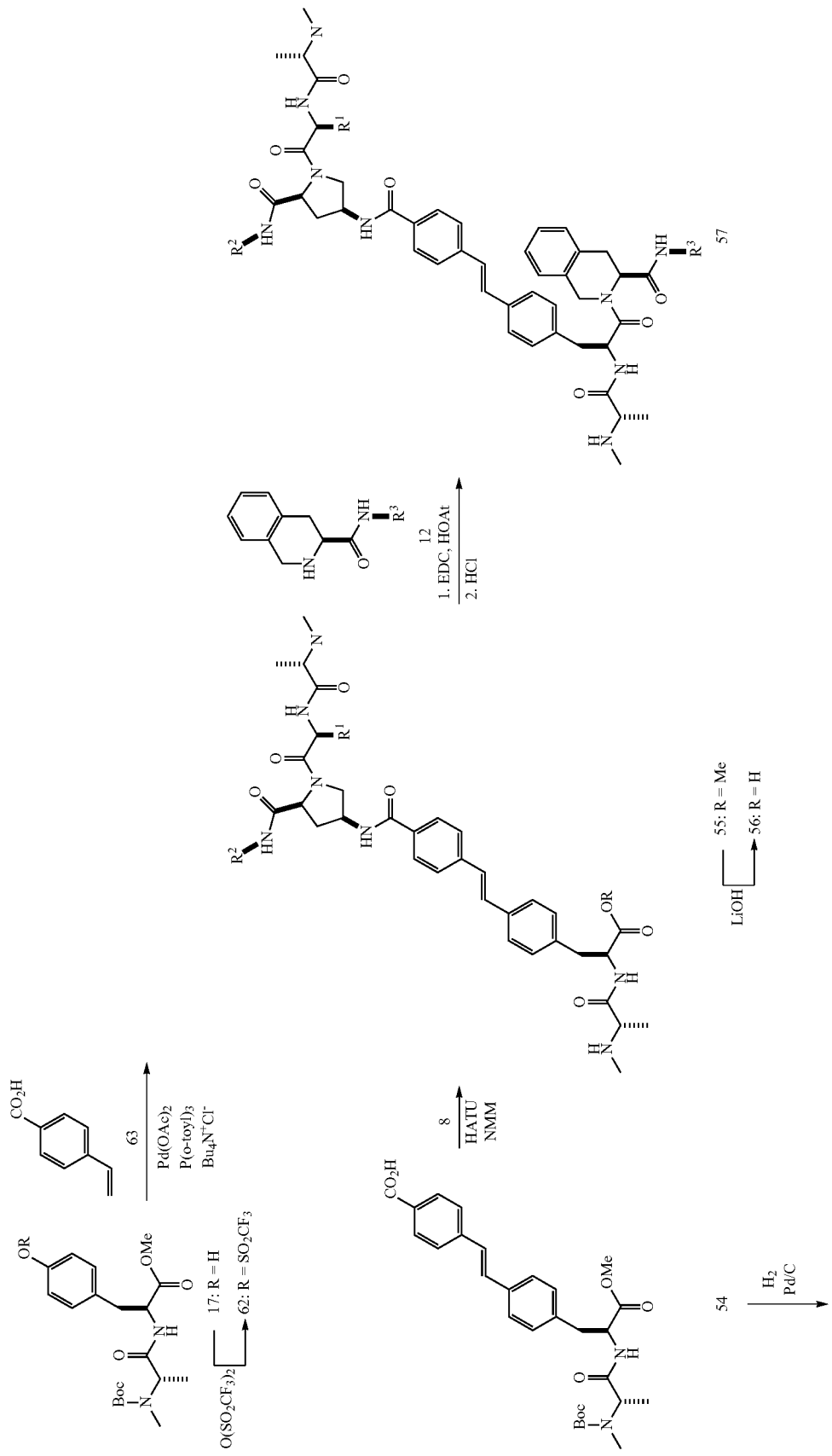

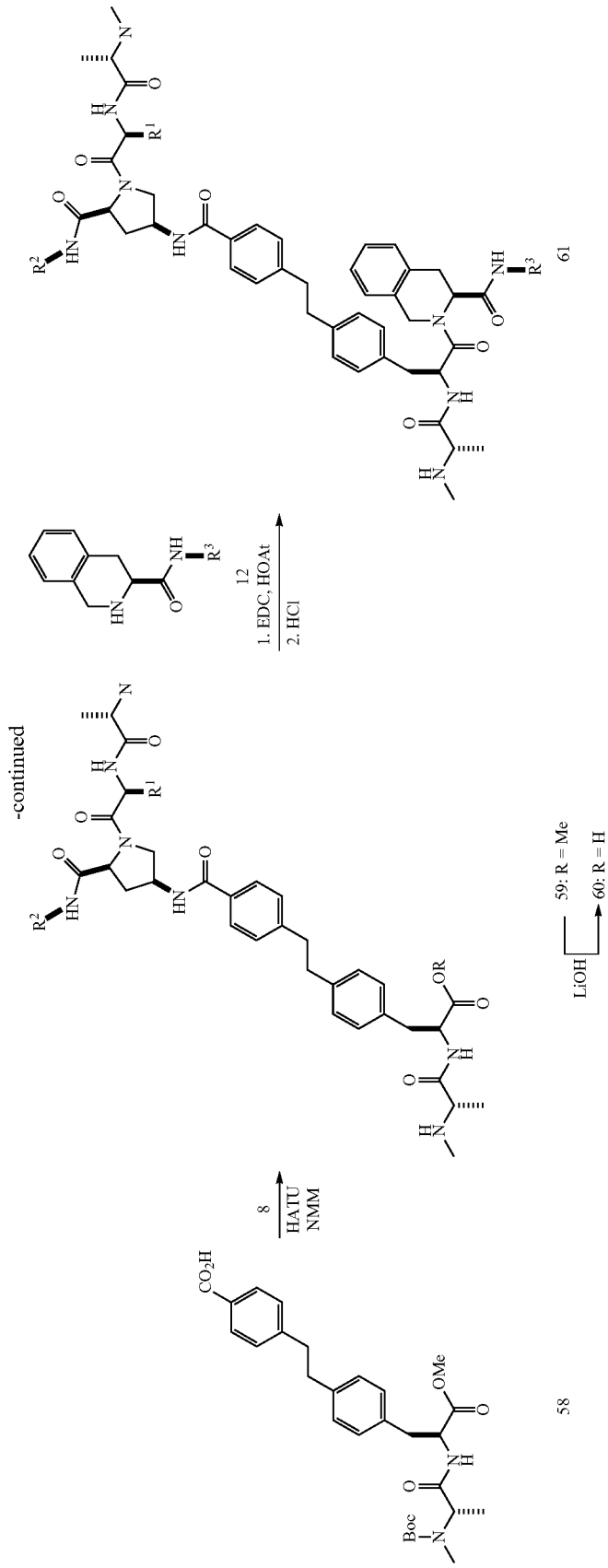

Heterodimeric analogues 57 and 61 can be prepared using the chemistry shown above in Scheme 8. The triflate 52, derived from phenol 17 can undergo a Heck reaction with 4-vinylbenzoic acid (53) and a palladium catalyst to afford the styryl benzoic acid derivative 54. Reduction of compound 54, under hydrogenation conditions afforded phenethyl benzoic acid derivative 58. Intermediates 54 and 58 can be converted to the desired analogues 57 and 61, respectively using chemistry previously described.

EXAMPLES

General Experimental

All reactions were carried out with continuous magnetic stirring under an atmosphere of dry nitrogen or argon. All evaporations and concentrations were carried out on a rotary evaporator under reduced pressure. Commercial reagents were obtained from Aldrich Chemical Co. unless otherwise noted and were used as received without additional purification. Solvents were commercial anhydrous grades and were used without further drying or purification. Flash chromatography was performed using prepacked REDISEP® $R_f$ silica gel columns on a CombiFlash Companion instrument.

Preparative Reverse Phase HPLC was performed with a linear gradient elution using $H_2O$/MeOH or $H_2O$/MeCN mixtures buffered with 0.1% trifluoroacetic acid or 10 mM $NH_4OAc$ and detection at 220 nm on one of the following columns: Shimadzu Sunfire S10 30×250 mm (flow rate=40 mL/min), or C18 PHENOMENEX® Luna S5 ODS 21×100 mm (flow rate=20 mL/min), or YMC S5 ODS 20×100 mm (flow rate=20 mL/min) or Waters XBridge C18 19×250 mm (flow rate=20 mL/min) Preparative Supercritical Fluid Chromatography (SFC) was performed using 78% $CO_2$/MeOH buffered with 0.1% diethylamine and detection at 220 nm on a CHIRALPAK® AS-H IDS 25×3 cm column (flow rate=85 mL/min).

All final products were characterized by $^1$H NMR, RP HPLC and electrospray ionization (ESI) or atmospheric pressure ionization (API) mass spectrometry (MS). $^1$H NMR spectra were obtained a 500 MHz or a 400 MHz Bruker instrument. Field strengths are expressed in units of δ (parts per million, ppm) relative to the solvent peaks, and peak multiplicities are designated as follows: s, singlet; d, doublet; dd, doublet of doublets; t, triplet; q, quartet; sxt, sextet; br s, broad singlet; m, multiplet.

Abbreviations

| | |
|---|---|
| Ac | acetyl |
| AcOH | acetic acid |
| Ac$_2$O | acetic anhydride |
| aq. | aqueous |
| Bn | benzyl |
| Boc | t-butyl carbamate |
| Boc$_2$O | di-t-butyl dicarbonate |
| Bu | butyl |
| Bu$_4$NI | tetrabutylammonium iodide |
| CDI | 1,1'-carbonyldiimidazole |
| conc. | concentrated |
| DBU | 1,8-diazabicyclo[5.4.0]undec-7-ene |
| DCE | dichloroethane |
| DCM | dichloromethane |
| DIEA | diisopropylethylamine |
| DMAP | 4-N,N-dimethylaminopyridine |
| DMF | dimethyl formamide |
| DMSO | dimethyl sulfoxide |
| EDC | 1-(dimethylaminopropyl)-3-ethylcarbodiimide hydrochloride |
| Et | ethyl |
| EtOAc | ethyl acetate |
| EtOH | ethanol |
| Et$_2$O | diethyl ether |
| Et$_3$N | triethylamine |
| FMOC (Fmoc) | Fluorenylmethyloxycarbonyl |
| h | hour(s) |
| HATU | O-(7-azabenzotriazol-1-yl)-N,N,N',N'-tetramethyluronium hexafluorophosphate |
| HPLC | high pressure liquid chromatography |
| i-PrOH | isopropanol |
| i-Pr$_2$EtN | di(isopropyl)ethylamine |
| min | minute(s) |
| Me | methyl |
| MeCN | acetonitrile |
| MeOH | methanol |
| Na(OAc)$_3$BH | sodium triacetoxyborohydride |
| NMM | N-methylmorpholine |
| NMP | n-methylpyrrolidinone |
| NMR | nuclear magnetic resonance |
| OTf | trifluoromethylsulfonyloxy |
| Pd/C | palladium on carbon |
| Pd(dppf)$_2$Cl$_2$ | [1,1'-bis(diphenylphosphino)ferrocene] dichloropalladium(II) |
| Pd(OAc)$_2$ | palladium acetate |
| Pd(PPh$_3$)$_4$ | tetrakis(triphenylphosphine)palladium |
| Pd$_2$(dba)$_3$ | tris(dibenzylideneacetone)dipalladium(0) |
| Ph | phenyl |
| PhMe | toluene |
| Ph$_2$TfN | 1,1,1-trifluoro-N-phenyl-N-(trifluoromethyl)sulfonyl methanesulfonamide |
| sat. | saturated |
| TBAI | tetrabutylammonium iodide |
| t-Bu | tertiary butyl |
| t-BuOH | tertiary butanol |
| t-BuOK | potassium tertiary-butoxide |
| t-BuOH | tertiary butanol |
| TFA | trifluoroacetic acid |
| Tf$_2$O | trifluoromethylsulfonic anhydride |
| THF | tetrahydrofuran |
| THIQ | tetrahydroisoquinoline |
| THP | tetrahydro-2H-pyran-2-yl |
| TMS | trimethylsilyl |
| TMS-OTf | trimethylsilyl triflate |
| TsO | p-toluenesulfonyl |

Example 1

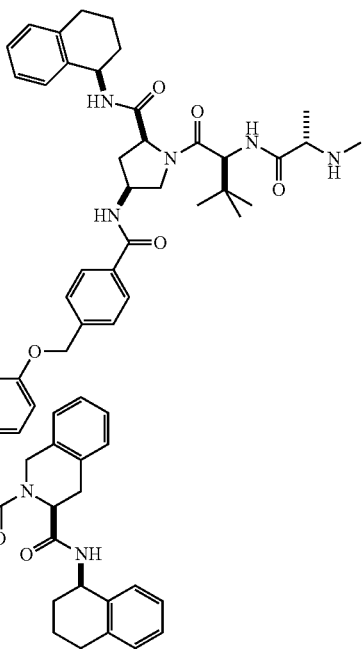

(S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide

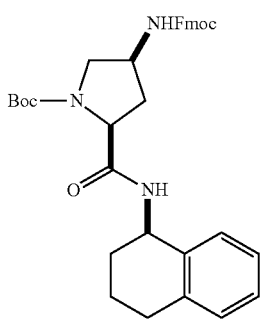

A) (2S,4S)-tert-Butyl 4-((((9H-fluoren-9-yl)methoxy)carbonyl)amino)-2-(((R)-1,2,3,4-tetrahydronaphthalen-1-yl)carbamoyl)pyrrolidine-1-carboxylate To a solution of (2S,4S)-Boc-gamma-(Fmoc-amino)-proline (Chem-Impex, 6.00 g, 13.3 mmol) in DMF (20 mL) at 0° C. were added EDC (3.05 g, 15.9 mmol), HOAt (2.17 g, 15.9 mmol) and 4-methylmorpholine (4.38 mL, 39.8 mmol). The reaction mixture was stirred at ice bath temperature for 20 min then treated with a solution of (R)-1,2,3,4-tetrahydronaphthalen-1-amine (ALFA AESAR®, 2.15 g, 14.6 mmol) in DMF (2 mL). The reaction mixture was stirred at rt for 1 h and cold water (100 mL) was added to the reaction mixture. The solid that formed was collected by filtration and washed with cold water (100 mL). The solid was dissolved in CH$_2$Cl$_2$ (200 mL) and the organic solution was washed with 5% aq. citric acid solution and brine, dried over MgSO$_4$, and filtered. The filtrate was concentrated in vacuo. The residue was dissolved in CH$_2$Cl$_2$ and purified by flash column chromatography (gradient elution from 10 to 30% EtOAc in CH$_2$Cl$_2$) provided the title compound (6.7 g, 87%) as a light tan solid. $^1$H NMR (400 MHz, CDCl$_3$) δ 7.79 (d, J=7.5 Hz, 2H), 7.67 (d, J=7.3 Hz, 2H), 7.42 (td, J=7.2, 4.0 Hz, 2H), 7.37-7.03 (m, 6H), 5.22 (br. s., 1H), 4.57-4.23 (m, 5H), 3.68-3.49 (m, 2H), 2.91-2.74 (m, 2H), 2.52 (d, J=13.4 Hz, 1H), 2.35-2.21 (m, 1H), 2.14 (d, J=5.1 Hz, 1H), 1.97-1.80 (m, 3H), 1.44 (s, 9H); MS(ESI$^+$) m/z 582.2 (M+H)$^+$.

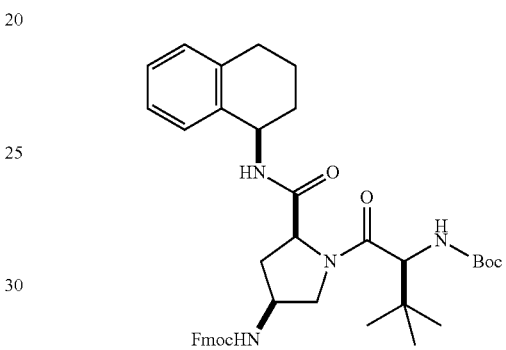

B) tert-Butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate To a solution of (2S,4S)-tert-butyl 4-((((9H-fluoren-9-yl)methoxy)carbonyl) amino)-2-(((R)-1,2,3,4-tetrahydronaphthalen-1-yl)carbamoyl)pyrrolidine-1-carboxylate (6.70 g, 11.5 mmol) in CH$_2$Cl$_2$ (50 mL) at rt was added TFA (15 mL) dropwise. The reaction mixture was stirred at rt for 2 h, and then concentrated in vacuo. The residue was dissolved in CH$_2$Cl$_2$ (200 mL) and washed with aq. K$_2$HPO$_4$ solution (50 mL). The organic layer was dried over MgSO$_4$, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 100%), which was used directly in the next step.

To a solution of (S)-2-((tert-butoxycarbonyl)amino)-3,3-dimethylbutanoic acid (3.19 g, 13.8 mmol) in DMF (20 mL) at 0° C. were added EDC (3.31 g, 17.3 mmol), HOAt (2.35 g, 17.3 mmol) and 4-methylmorpholine (3.80 mL, 34.5 mmol). The reaction mixture was stirred at ice bath temperature for 20 min, then treated with a suspension of (9H-fluoren-9-yl)methyl ((3S,5S)-5-(((R)-1,2,3,4-tetrahydronaphthalen-1-yl)carbamoyl)pyrrolidin-3-yl)carbamate (5.54 g, 11.5 mmol) in DMF (5 mL). The reaction mixture was stirred at rt for 1 h and cold water (200 mL) was added to the reaction mixture. The solid that formed was collected by filtration and washed with of cold water (100 mL). The solid was dissolved in CH$_2$Cl$_2$ (200 mL). The organic solution was washed with sat. aq. NaHCO₃ solution, 5% aq. citric acid solution and brine, dried over MgSO₄ and filtered. The filtrate was concentrated in vacuo. The residue was dissolved in CH₂Cl₂ and purified using flash column chromatography (gradient elution from 10 to 30% EtOAc in CH₂Cl₂) provided the title compound (7.10 g, 89%) as a light tan solid. MS(ESI⁺) m/z 695.5 (M+H)⁺.

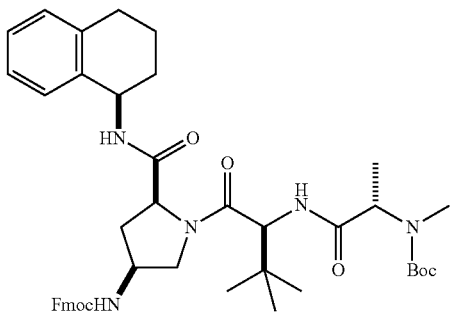

C) tert-Butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-3,3-dimethyl-1-((2S,4S)-4-(((9H-fluoren-9-yl)methoxy)carbonyl)amino)-2-(((R)-1,2,3,4-tetrahydronaphthalen-1-yl)carbamoyl)pyrrolidin-1-yl)-1-oxobutan-2-yl)carbamate (7.10 g, 10.2 mmol) in CH₂Cl₂ (50 mL) at rt was added TFA (15 mL) dropwise. The reaction mixture was stirred at rt for 2 h, and then concentrated in vacuo. The residue was dissolved in CH₂Cl₂ (200 mL) and washed with aq. K₂HPO₄ solution (50 mL). The organic layer was dried over MgSO₄, filtered and concentrated in vacuo to give crude (9H-fluoren-9-yl)methyl ((3S,5S)-5-(((R)-1,2,3,4-tetrahydronaphthalen-1-yl)carbamoyl)pyrrolidin-3-yl)carbamate (6.08 g, 100%), which was used directly in the next step.

To a solution of (S)-2-((tert-butoxycarbonyl)(methyl)amino)propanoic acid (Chem-Impex, 2.49 g, 12.3 mmol) in DMF (20 mL) at 0° C. were added EDC (2.94 g, 15.3 mmol), HOAt (2.09 g, 15.3 mmol) and 4-methylmorpholine (2.81 mL, 25.6 mmol). The reaction mixture was stirred at ice bath temperature for 20 min, and then treated with a solution of (9H-fluoren-9-yl)methyl ((3S,5S)-5-(((R)-1,2,3,4-tetrahydronaphthalen-1-yl)carbamoyl)pyrrolidin-3-yl)carbamate (6.45 g, 10.2 mmol) in DMF (5 mL). The reaction mixture was stirred at rt for 2 h and then cold water (200 mL) was added to the reaction mixture. The solid that formed was collected by filtration and washed with cold water (100 mL). The solid was dissolved in CH₂Cl₂ (200 mL). The organic solution was washed with sat. aq. NaHCO₃ solution, 5% aq. citric acid solution and brine, dried over MgSO₄, and filtered. The filtrate was concentrated in vacuo. The residue was dissolved in CH₂Cl₂ and purified by flash column chromatography (gradient elution from 10 to 40% EtOAc in CH₂Cl₂) provided the title compound (6.14 g, 77%) as a light tan solid. MS(ESI⁺) m/z 780.5 (M+H)⁺.

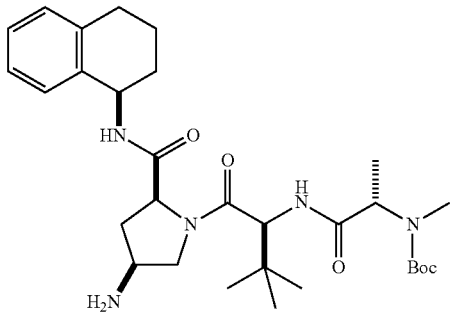

D) tert-Butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate To a solution of tert-butyl ((S)-1-(((S)-1-((2S,4S)-4-((((9H-fluoren-9-yl)methoxy)carbonyl)amino)-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (6.14 g, 7.87 mmol) in CH₂Cl₂ (40 mL) was added piperidine (4.67 mL, 47.2 mmol) dropwise. The reaction mixture was stirred at rt for 2 h and concentrated in vacuo. The residue was washed with methanol and the resulting solid was removed by filtration. The filtrate was concentrated in vacuo and purified by flash column chromatography (gradient elution from CH₂Cl₂ to 10% MeOH in DCM) to give the title compound (3.48 g, 79%) as a light tan solid. MS(ESI⁺) m/z 558.4 (M+H)⁺.

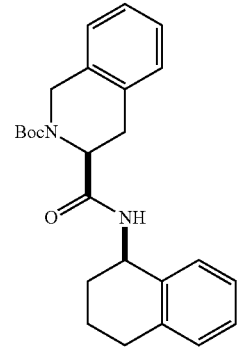

E) (S)-tert-Butyl 3-(((R)-1,2,3,4-tetrahydronaphthalen-1-yl)carbamoyl)-3,4-dihydroisoquinoline-2(1H)-carboxylate To a 0° C. solution of (S)-2-(tert-butoxycarbonyl)-1,2,3,4-tetrahydroisoquinoline-3-carboxylic acid (Synthetech, 800 mg, 2.88 mmol) and HOAt (412 mg, 3.03 mmol) in THF (9.5 mL) was added a solution of EDC (774 mg, 4.04 mmol) in THF (2.4 mL) and DMF (2.4 mL). The resulting heterogeneous mixture was stirred at 0° C. for 30 min and then (R)-1,2,3,4-tetrahydronaphthalen-1-amine (Aldrich, 466 μL, 3.17 mmol) was added. The reaction mixture was allowed to warm to room temperature overnight and then poured into a separatory funnel containing EtOAc and sat. aq. NaHCO₃ solution. The aqueous layer was extracted with EtOAc (3×), and the combined organic extracts were washed with 1N HCl. The combined aqueous layer was extracted an additional time with EtOAc. The combined organic extracts were dried over Na$_2$SO$_4$, filtered, concentrated in vacuo to give the title compound (1.17 g, 100%) as a viscous yellow oil. MS(ESI$^+$) m/z 407.2 (M+H)$^+$.

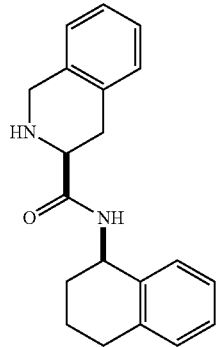

F) (S)—N—((R)-1,2,3,4-Tetrahydronaphthalen-1-yl)-1,2,3,4-tetrahydroisoquinoline-3-carboxamide To a solution of (S)-tert-butyl 3-((R)-1,2,3,4-tetrahydronaphthalen-1-ylcarbamoyl)-3,4-dihydroisoquinoline-2(1H)-carboxylate (1.17 g, 2.88 mmol) in CH$_2$Cl$_2$ (11.5 mL) was added HCl (18.0 mL, 72.0 mmol, 4 N in dioxane). The resulting solution was stirred at room temperature for 1 h and then concentrated in vacuo until a white solid precipitated. Vacuum filtration of the solution provided the title compound (885 mg, 90%) as a white solid. $^1$H NMR (CD$_3$OD, mixture of amide rotamers) δ 7.35-7.22 (m, 5H), 7.20-7.09 (m, 3H), 5.17 (t, J=5.3 Hz, 1H), 4.56 (br s, 1H), 4.42 (s, 2H), 4.13 (dd, J=11.8, 5.0 Hz, 1H), 3.27-3.10 (m, 1H), 2.93-2.71 (m, 2H), 2.13-1.78 (m, 4H); MS(ESI$^+$) m/z 307.2 (M+H)$^+$.

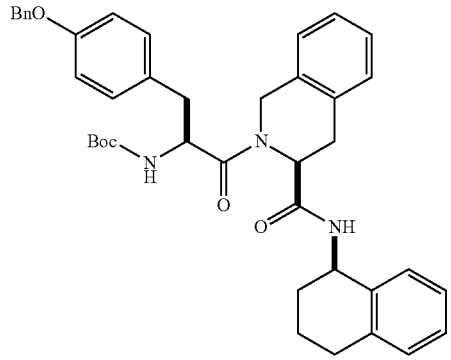

G) tert-Butyl ((S)-3-(4-(benzyloxy)phenyl)-1-oxo-1-((S)-3-(((R)-1,2,3,4-tetrahydronaphthalen-1-yl)carbamoyl)-3,4-dihydroisoquinolin-2(1H)-yl)propan-2-yl)carbamate To a 0° C. solution of (S)-3-(4-(benzyloxy)phenyl)-2-((tert-butoxycarbonyl)amino)propanoic acid (TCI, 275 mg, 0.74 mmol) in DMF (3.7 mL) was added EDC (170 mg, 0.89 mmol) followed by HOAt (121 mg, 0.89 mmol). The resulting reaction mixture was stirred at room temperature for 10 min and then recooled to 0° C. (S)—N—((R)-1,2,3,4-tetrahydronaphthalen-1-yl)-1,2,3,4-tetrahydroisoquinoline-3-carboxamide (227 mg, 0.74 mmol) was added followed by NMM (244 μL, 2.22 mmol). The reaction mixture was stirred warming to room temperature over 2 h and then poured into a separatory funnel containing EtOAc and sat.

aq. NaHCO$_3$ solution. The aqueous layer was extracted with EtOAc (3×), and the combined organic extracts were washed with 1N HCl, sat. aq. NaHCO$_3$ solution and brine. The extracts were dried over Na$_2$SO$_4$, filtered, concentrated in vacuo to give the title compound (489 mg, 100%) as a white, oily solid. MS(ESI$^+$) m/z 660.3 (M+H)$^+$.

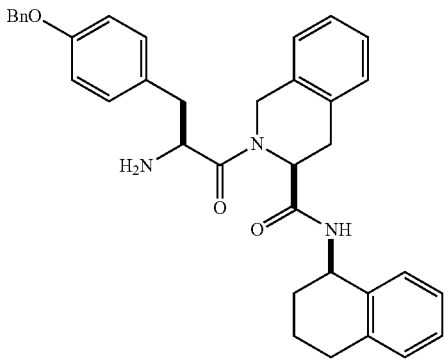

H) (S)-2-((S)-2-Amino-3-(4-(benzyloxy)phenyl)propanoyl)-N—((R)-1,2,3,4-tetrahydronaphthalen-1-yl)-1,2,3,4-tetrahydroisoquinoline-3-carboxamide To tert-butyl ((S)-3-(4-(benzyloxy)phenyl)-1-oxo-1-((S)-3-(((R)-1,2,3,4-tetrahydronaphthalen-1-yl)carbamoyl)-3,4-dihydroisoquinolin-2(1H)-yl)propan-2-yl)carbamate (489 mg, 0.74 mmol) in CH$_2$Cl$_2$ (20 mL) was added TFA (5.0 mL, 65.2 mmol). The resulting solution was stirred at room temperature for 1 h, then concentrated in vacuo and redissolved in EtOAc and sat. aq. NaHCO$_3$ solution. The aqueous layer was extracted with EtOAc (3×). The combined organics were washed with sat. aq. NaHCO$_3$ solution and brine, dried over Na$_2$SO$_4$, filtered and concentrated in vacuo to provide the title compound (348 mg, 84%) as a white solid. MS(ESI$^+$) m/z 560.3 (M+H)$^+$.

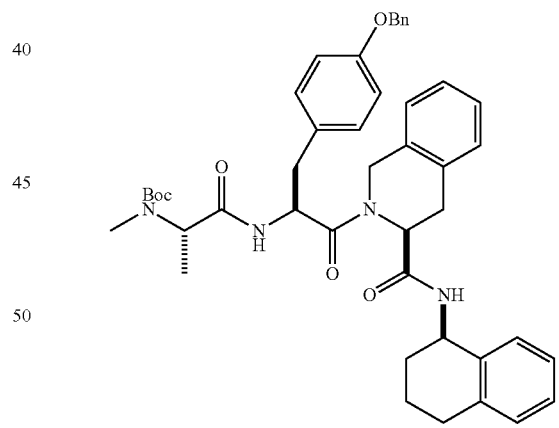

I) tert-Butyl ((S)-1-(((S)-3-(4-(benzyloxy)phenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate Following a procedure analogous to that for the synthesis of Compound G, (S)-2-((tert-butoxycarbonyl)(methyl)amino)propanoic acid (Advanced ChemTech, 126 mg, 0.62 mmol) and (S)-2-((S)-2-amino-3-(4-(benzyloxy)phenyl)propanoyl)-N—((R)-1,2,3,4-tetrahydronaphthalen-1-yl)-1,2,3,4-tetrahydroisoquinoline-3-carboxamide (347 mg, 0.62 mmol) were converted to the title compound (446 mg, 97%). MS(ESI⁺) m/z 745.5 (M+H)⁺.

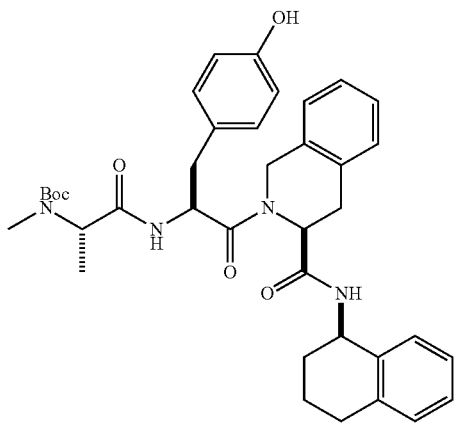

J) tert-Butyl ((S)-1-(((S)-3-(4-hydroxyphenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl) carbamate To a 50 mL pressure flask containing 5% Pd/C (64 mg, 0.60 mmol) was added tert-butyl ((S)-1-(((S)-3-(4-(benzyloxy)phenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate (445 mg, 0.597 mmol). EtOAc (5.0 mL) and MeOH (5.0 mL) were added, and the resulting suspension was stirred under 5 psi H₂ for 12 h and then under 25 psi H₂ for 5 h. The reaction mixture was filtered through a pad of CELITE® washing with EtOAc. The filtrate was concentrated in vacuo to give the title compound (383 mg, 98%) as a colorless, oily solid. MS(ESI⁺) m/z 655.3 (M+H)⁺.

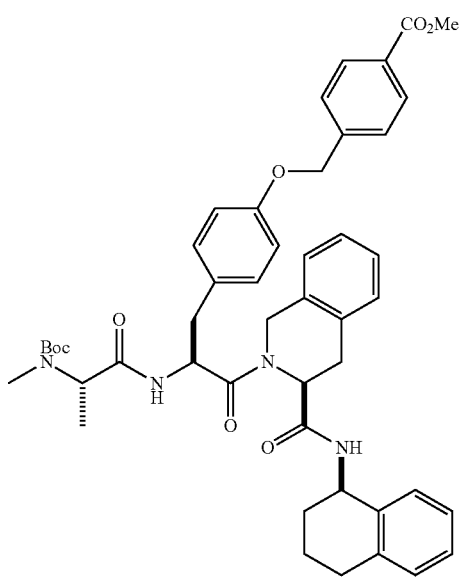

K) Methyl 4-((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)methyl)benzoate To tert-butyl ((S)-1-(((S)-3-(4-hydroxyphenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate (81 mg, 0.12 mmol) and methyl 4-(bromomethyl)benzoate (42 mg, 0.19 mmol) in DMF (620 µL) was added Cs₂CO₃ (81 mg, 0.25 mmol). The resulting reaction mixture was stirred overnight at room temperature and then poured into a separatory funnel containing EtOAc and sat. aq. NH₄Cl solution. The aqueous layer was extracted with EtOAc (3×). The combined organic extracts were washed with 1N HCl and brine, dried over Na₂SO₄, filtered and concentrated in vacuo to provide the title compound (99 mg, 100%) as a colorless oil. MS(ESI⁺) m/z 803.4 (M+H)⁺.

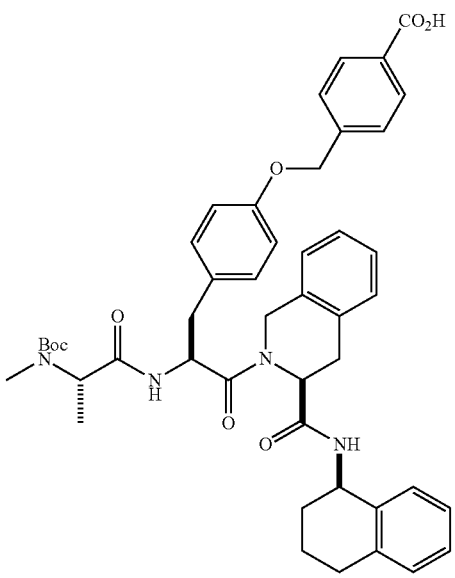

L) 4-((4-((S)-2-((S)-2-((tert-Butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)methyl)benzoic acid To a solution of methyl 4-((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)methyl)benzoate (99 mg, 0.12 mmol) in THF (550 µL) and MeOH (270 µL) was added 1N NaOH (620 µL, 0.62 mmol). The reaction mixture was stirred at room temperature for 2 h. Additional 1N NaOH (500 µL, 0.50 mmol) was then added and stirring was continued for 1.5 h. Additional 1N NaOH (500 µL, 0.50 mmol) was added and stirring was continued for 1.5 h. The reaction mixture was then poured into EtOAc and 1N HCl. The aqueous layer was extracted with EtOAc (3×). The combined organic extracts were dried over Na₂SO₄, filtered and concentrated in vacuo to give the title compound (97 mg, 100%) as a white solid. MS(ESI⁺) m/z 789.5 (M+H)⁺.

M) (S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide To a solution of 4-((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)methyl)benzoic acid (65 mg, 0.082 mmol) and HATU (41 mg, 0.11 mmol) in DMF (500 µL) and THF (500 µL) was added a solution of tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D, 46 mg, 0.082 mmol) and NMM (27 µL, 0.25 mmol) in THF (500 µL) dropwise via syringe. The resulting reaction mixture was stirred at room temperature overnight and then poured into a sep funnel containing EtOAc and sat. NH$_4$Cl. The aqueous layer was extracted with EtOAc (3×). The combined organic layer was washed with 1N HCl and sat. NaCl, dried over Na$_2$SO$_4$, filtered and concentrated in vacuo. The crude oil was dissolved in CH$_2$Cl$_2$ (820 µL) and DMF (820 µL). HCl (510 µL, 2.05 mmol, 4 N in dioxane) was added, and the resulting reaction mixture was stirred at room temperature for 3 h, then concentrated in vacuo and purified using prep HPLC to give the title compound (11 mg, 11%) as an off-white solid after lyophilization. MS(ESI$^+$) m/z 1128.2 (M+H)$^+$.

Examples 2 to 5

The following examples were prepared according to the procedures described for the synthesis of Example 1.

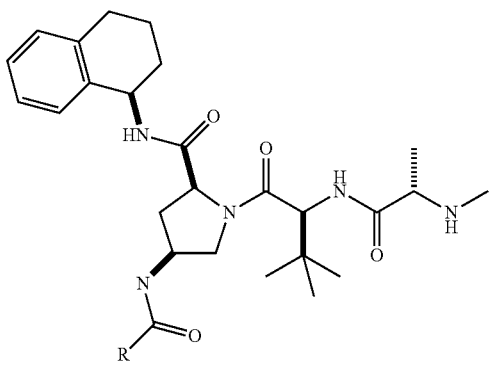

| Example No. | R | Name | LCMS (M + H) |
|---|---|---|---|
| 2 | 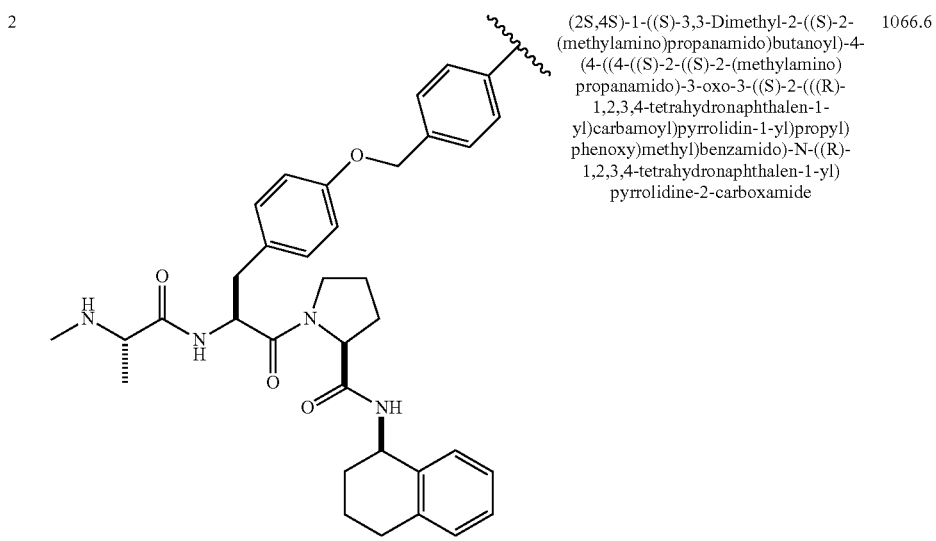 | (2S,4S)-1-((S)-3,3-Dimethyl-2-((S)-2-(methylamino)propanamido)butanoyl)-4-(4-((4-((S)-2-((S)-2-(methylamino)propanamido)-3-oxo-3-((S)-2-(((R)-1,2,3,4-tetrahydronaphthalen-1-yl)carbamoyl)pyrrolidin-1-yl)propyl)phenoxy)methyl)benzamido)-N-((R)-1,2,3,4-tetrahydronaphthalen-1-yl)pyrrolidine-2-carboxamide | 1066.6 |

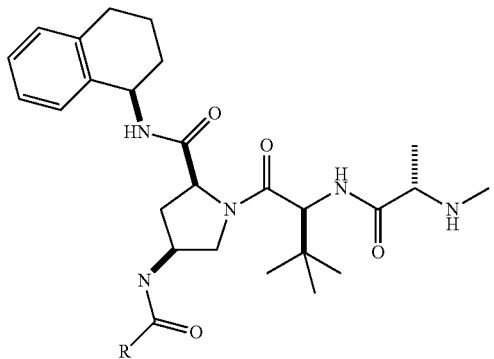

| Example No. | R | Name | LCMS (M + H) |
|---|---|---|---|
| 3 | 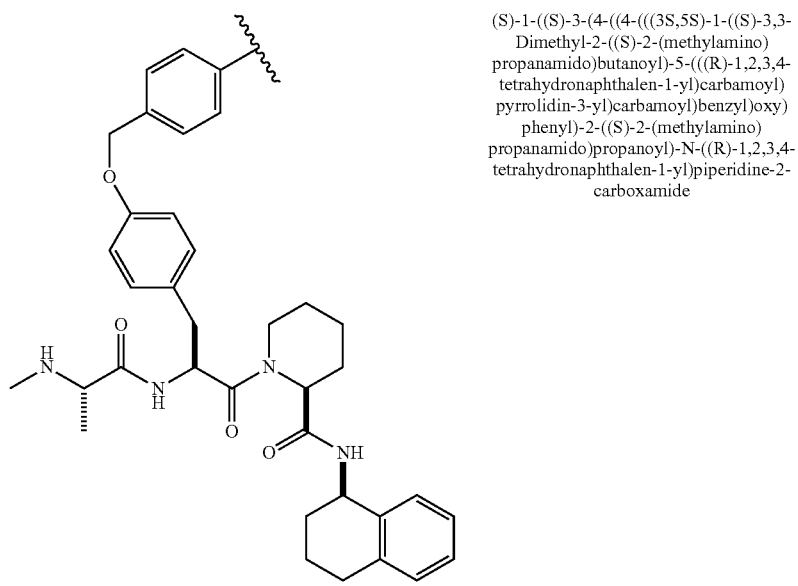 | (S)-1-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanamido)propanoyl)-N-((R)-1,2,3,4-tetrahydronaphthalen-1-yl)piperidine-2-carboxamide | 1080.7 |
| 4 | 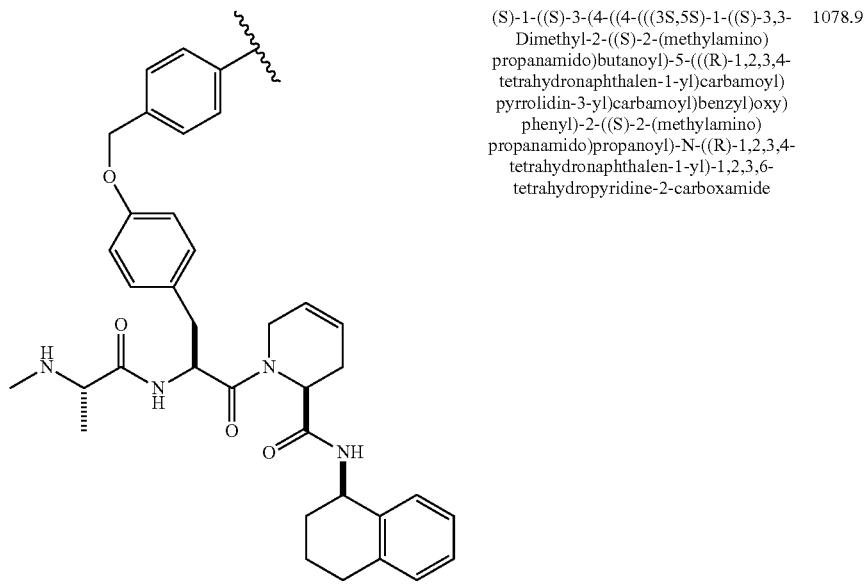 | (S)-1-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanamido)propanoyl)-N-((R)-1,2,3,4-tetrahydronaphthalen-1-yl)-1,2,3,6-tetrahydropyridine-2-carboxamide | 1078.9 |

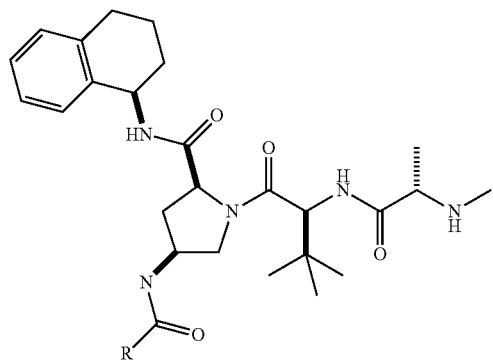
| Example No. | R | Name | LCMS (M + H) |
|---|---|---|---|
| 5 | 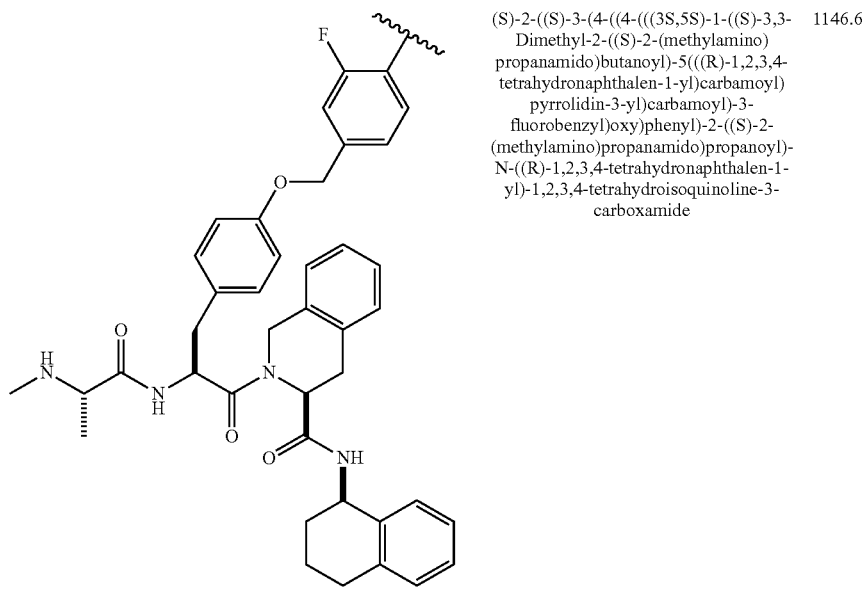 | (S)-2-((S)-3-(4-((4-(((3S,5S)-1-((S)-3,3-Dimethyl-2-((S)-2-(methylamino)propanamido)butanoyl)-5(((R)-1,2,3,4-tetrahydronaphthalen-1-yl)carbamoyl)pyrrolidin-3-yl)carbamoyl)-3-fluorobenzyl)oxy)phenyl)-2-((S)-2-(methylamino)propanamido)propanoyl)-N-((R)-1,2,3,4-tetrahydronaphthalen-1-yl)-1,2,3,4-tetrahydroisoquinoline-3-carboxamide | 1146.6 |

Example 6

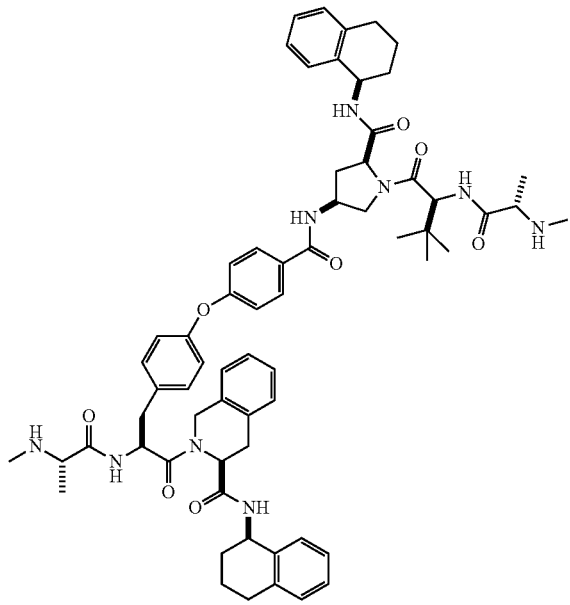

(S)-2-((S)-3-(4-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenoxy)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide

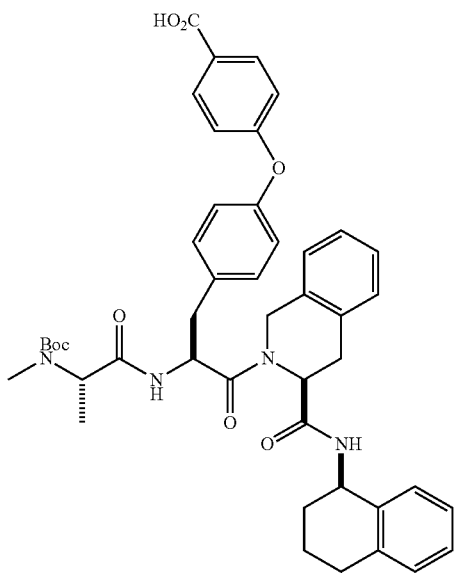

A) 4-(4-((S)-2-((S)-2-((tert-Butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)benzoic acid To a 1 dram pressure vial containing tert-butyl ((S)-1-((S)-3-(4-hydroxyphenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate (Compound I of Example 1, 50 mg, 0.076 mmol) in dioxane (510 µL) was added N,N-dimethylglycine (3 mg, 0.025 mmol), Cs$_2$CO$_3$ (50 mg, 0.15 mmol), 4-bromobenzoic acid (16 mg, 0.080 mmol) and CuI (1 mg, 7.6 µmol). The vial was capped, and the resulting mixture was stirred at 100° C. overnight. Additional 4-bromobenzoic acid (16 mg, 0.080 mmol), CuI (1 mg, 7.6 µmol) and N,N-dimethylglycine (3 mg, 0.025 mmol) were added and the sides of the vial were rinsed with dioxane (500 µL). The reaction mixture was stirred at 95° C. for 24 h, then at room temperature for 3 days and then poured into a separatory funnel containing EtOAc and sat. aq. NH$_4$Cl solution. The aqueous layer was extracted with EtOAc (3×), and the combined organics were dried over Na$_2$SO$_4$. Filtration and concentration in vacuo provided a crude oil which was purified using prep HPLC to give the title compound (26 mg, 44%) as a colorless oil. MS(ESI$^+$) m/z 775.5 (M+H)$^+$.

B) (S)-2-((S)-3-(4-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenoxy)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide Following a procedure analogous to that for the synthesis of Compound M of Example 1, 4-(4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenoxy)benzoic acid (26 mg, 0.034 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D of Example 1, 19 mg, 0.034 mmol) were converted to the title compound (8 mg, 19%). MS(ESI$^+$) m/z 1114.6 (M+H)$^+$.

Example 7

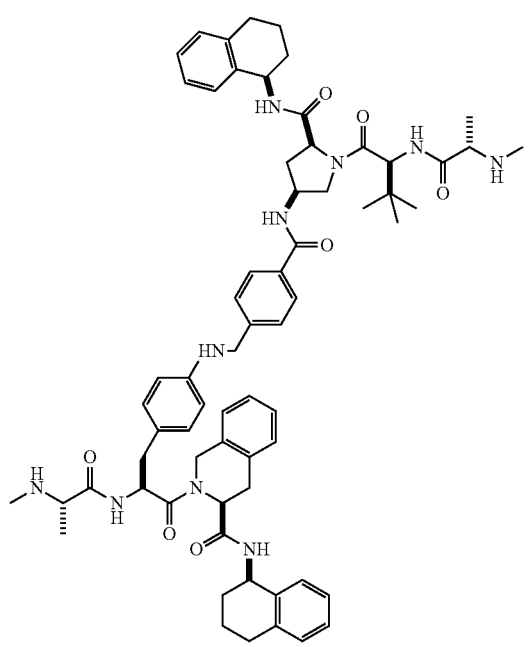

(S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)amino)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide

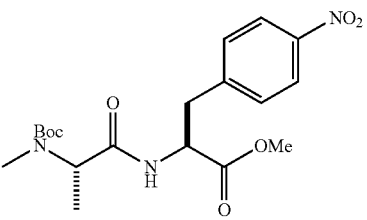 [SMILES: COC(=O)[C@H](Cc1ccc([N+](=O)[O-])cc1)NC(=O)[C@H](C)N(C)C(=O)OC(C)(C)C]

A) (S)-Methyl 2-((S)-2-((tert-butoxycarbonyl)(methyl)amino)propanamido)-3-(4-nitrophenyl)propanoate Following a procedure analogous to that for the synthesis of Compound G of Example 1, (S)-2-((tert-butoxycarbonyl)(methyl)amino)propanoic acid (Advanced ChemTech, 0.78 g, 3.84 mmol) and (S)-methyl 2-amino-3-(4-nitrophenyl)propanoate, HCl (Aldrich, 1.00 g, 3.84 mmol) were converted to the title compound (1.14 g, 72%). MS(ESI⁺) m/z 310.1 (M+H-Boc)⁺.

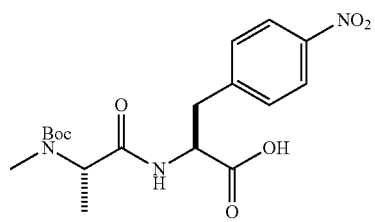 [SMILES: C[C@@H](C(=O)N[C@@H](Cc1ccc([N+](=O)[O-])cc1)C(=O)O)N(C)C(=O)OC(C)(C)C]

B) (S)-2-((S)-2-((tert-Butoxycarbonyl)(methyl)amino)propanamido)-3-(4-nitrophenyl)propanoic acid To a solution of (S)-methyl 2-((S)-2-((tert-butoxycarbonyl)(methyl)amino)propanamido)-3-(4-nitrophenyl)propanoate (568 mg, 1.39 mmol) in THF (2.3 mL) and MeOH (1.2 mL) was added 1N NaOH (6.9 mL, 6.94 mmol). The resulting solution was stirred at room temperature for 2 h and then poured into a sep funnel containing EtOAc and 1N HCl. The aqueous layer was extracted with EtOAc (3×). The combined organics were washed with sat. NaCl, dried over Na₂SO₄, filtered and concentrated in vacuo to give the title compound (547 mg, 100%) as a yellow oil. MS(ESI⁺) m/z 296.1 (M+H-Boc)⁺.

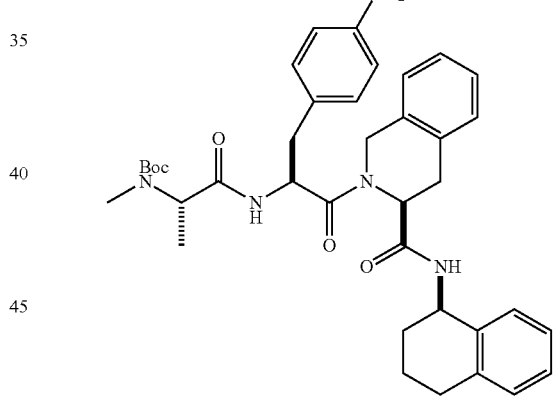

C) tert-Butyl methyl((S)-1-(((S)-3-(4-nitrophenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)carbamate Following a procedure analogous to that for the synthesis of Compound G of Example 1, (S)-2-((S)-2-((tert-butoxycarbonyl)(methyl)amino)propanamido)-3-(4-nitrophenyl)propanoic acid (250 mg, 0.63 mmol) and (S)—N—((R)-1,2,3,4-tetrahydronaphthalen-1-yl)-1,2,3,4-tetrahydroisoquinoline-3-carboxamide (Compound F of Example 1, 194 mg, 0.63 mmol) were converted to the title compound (348 mg, 80%). MS(ESI⁺) m/z 684.4 (M+H)⁺.

D) tert-Butyl ((S)-1-(((S)-3-(4-aminophenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate

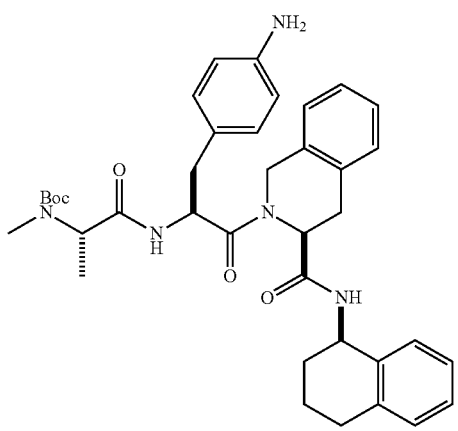

To a 50 mL pressure flask containing 5% Pd/C (54 mg, 0.51 mmol) was added tert-butyl methyl((S)-1-(((S)-3-(4-nitrophenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)carbamate (347 mg, 0.51 mmol) in MeOH (5.0 mL). The resulting suspension was stirred under $H_2$ at 5 psi for 8 h and then filtered through a pad of CELITE® washing with EtOAc. The filtrate was concentrated in vacuo. The residue was dissolved in $CH_2Cl_2$ and filtered through a pad of silica gel washing with EtOAc and then with 5% MeOH/$CHCl_3$. The filtrate was concentrated in vacuo to give the title compound (272 mg, 82%) as a yellow oil. MS(ESI$^+$) m/z 654.4 (M+H)$^+$.

E) 4-(((4-((S)-2-((S)-2-((tert-Butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)amino)methyl)benzoic acid To tert-butyl ((S)-1-(((S)-3-(4-aminophenyl)-1-oxo-1-((S)-3-(((R)-1,2,3,4-tetrahydronaphthalen-1-yl)carbamoyl)-3,4-dihydroisoquinolin-2(1H)-yl)propan-2-yl)amino)-1-oxopropan-2-yl)(methyl)carbamate (50 mg, 0.076 mmol), 4-formylbenzoic acid (13 mg, 0.084) and 4 Å molecular sieves (200 mg) in DCE (380 µL) was added AcOH (22 µL, 0.38 mmol). The resulting reaction mixture was stirred at room temperature for 1.5 h. Na(OAc)$_3$BH (32 mg, 0.15 mmol) was added to the mixture and stirring was continued for 5 min. The reaction mixture was then filtered through a pad of CELITE®, rinsing with EtOAc. The filtrate was washed with 1N NaOH and sat. NaCl, and then dried over Na$_2$SO$_4$. Filtration and concentration in vacuo provided a crude oil which was purified using prep SFC to give the title compound (31 mg, 50%) as a pale yellow oil. MS(ESI$^+$) m/z 788.4 (M+H)$^+$.

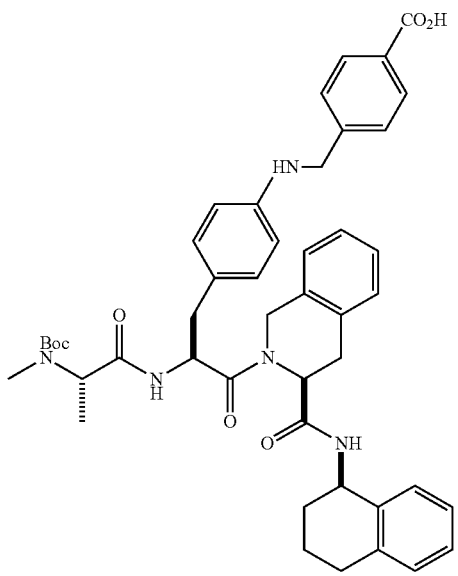

F) (S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)amino)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide Following a procedure analogous to that for the synthesis of Compound M of Example 1, 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)amino)methyl)benzoic acid (31 mg, 0.039 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D of Example 1, 24 mg, 0.043 mmol) were converted to the title compound (2 mg, 4%). MS(ESI$^+$) m/z 1128.5 (M+H)$^+$.

Example 8

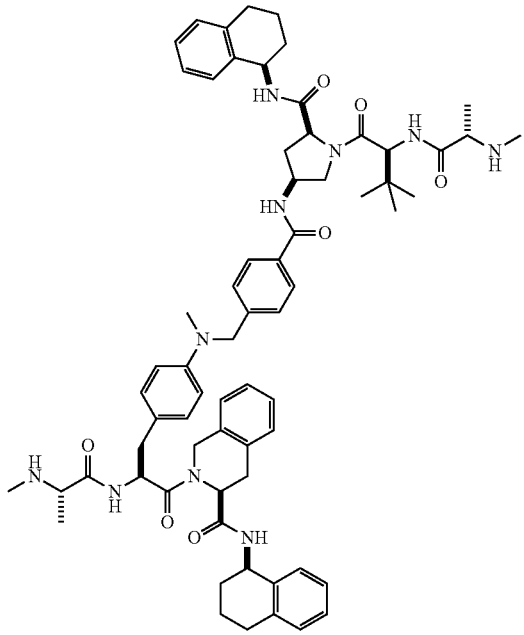

(S)-2-((S)-3-(4-((4-(((3S,5S)-1-((S)-3,3-Dimethyl-2-
((S)-2-(methylamino)propanamido)butanoyl)-5-
(((R)-1,2,3,4-tetrahydronaphthalen-1-yl)carbamoyl)
pyrrolidin-3-yl)carbamoyl)benzyl)(methyl)amino)
phenyl)-2-((S)-2-(methylamino)propanamido)
propanoyl)-N—((R)-1,2,3,4-tetrahydronaphthalen-1-
yl)-1,2,3,4-tetrahydroisoquinoline-3-carboxamide

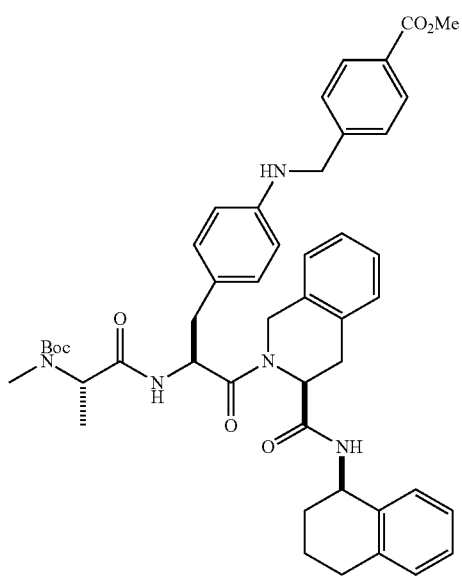

A) Methyl 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)amino)methyl)benzoate Following a procedure analogous to that for the synthesis of Compound E of Example 7, tert-butyl ((S)-1-(((S)-3-(4-aminophenyl)-1-oxo-1-((S)-3-(((R)-1,2,3,4-tetrahydronaphthalen-1-yl)carbamoyl)-3,4-dihydroisoquinolin-2(1H)-yl) propan-2-yl)amino)-1-oxopropan-2-yl)(methyl)carbamate (Compound D of Example 7, 100 mg, 0.15 mmol) and methyl 4-formylbenzoate (25 mg, 0.15 mmol) were converted to the title compound (102 mg, 83%). MS(ESI⁺) m/z 802.7 (M+H)⁺.

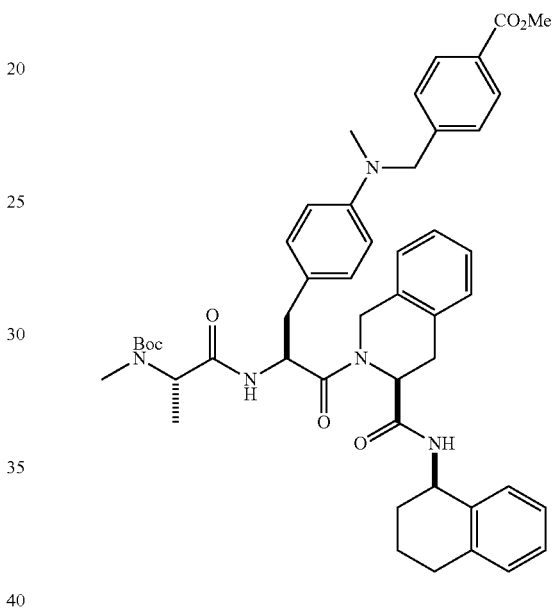

B) Methyl 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)(methyl)amino)methyl)benzoate To methyl 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)amino)methyl)benzoate (57 mg, 0.071 mmol) in CH₂Cl₂ (1.0 mL) and i-PrOH (0.5 mL) was added formaldehyde (16 μL, 0.21 mmol) followed by Na(OAc)₃BH (45 mg, 0.21 mmol). The resulting reaction mixture was stirred at room temperature for 2 h. Additional formaldehyde (16 μL, 0.21 mmol) and Na(OAc)₃BH (45 mg, 0.21 mmol) were then added and stirring was continued for 60 h. Additional formaldehyde (16 μL, 0.21 mmol) and Na(OAc)₃BH (45 mg, 0.21 mmol) were added, and the reaction mixture was stirred for 1.5 h at room temperature. Formaldehyde (16 μL, 0.21 mmol) and Na(OAc)₃BH (45 mg, 0.21 mmol) were again added, and after 1 h the reaction mixture was poured into a sep funnel containing EtOAc and sat. aq. NaHCO₃ solution. The aqueous layer was extracted with EtOAc (3×), and the combined organic extracts were washed with brine. The extracts were dried over Na₂SO₄, filtered, concentrated in vacuo to give a crude oil (60 mg)

which was used with purification in the subsequent step. MS(ESI⁺) m/z 817.3 (M+H)⁺.

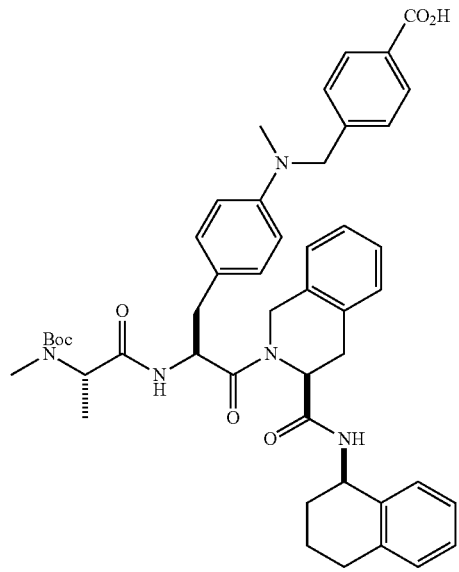

C) 4-(((4-((S)-2-((S)-2-((tert-Butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)(methyl)amino)methyl)benzoic acid Following a procedure analogous to that for the synthesis of Compound B of Example 7, methyl 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)(methyl)amino)methyl)benzoate (58 mg, 0.071 mmol) was converted to the title compound (20 mg, 35%) after purification using prep SFC. MS(ESI⁺) m/z 802.5 (M+H)⁺.

D) (S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)(methyl)amino)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide Following a procedure analogous to that for the synthesis of Compound M of Example 1, 4-(((4-((S)-2-((S)-2-((tert-butoxycarbonyl)(methyl)amino)propanamido)-3-oxo-3-((S)-3-(((R)-1,2,3,4-tetrahydronaphthalen-1-yl)carbamoyl)-3,4-dihydroisoquinolin-2(1H)-yl)propyl)phenyl)(methyl)amino)methyl)benzoic acid (20 mg, 0.025 mmol) and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D of Example 1, 14 mg, 0.025 mmol) were converted to the title compound (8 mg, 25%). MS(ESI⁺) m/z 1341.7 (M+H)⁺.

Example 9

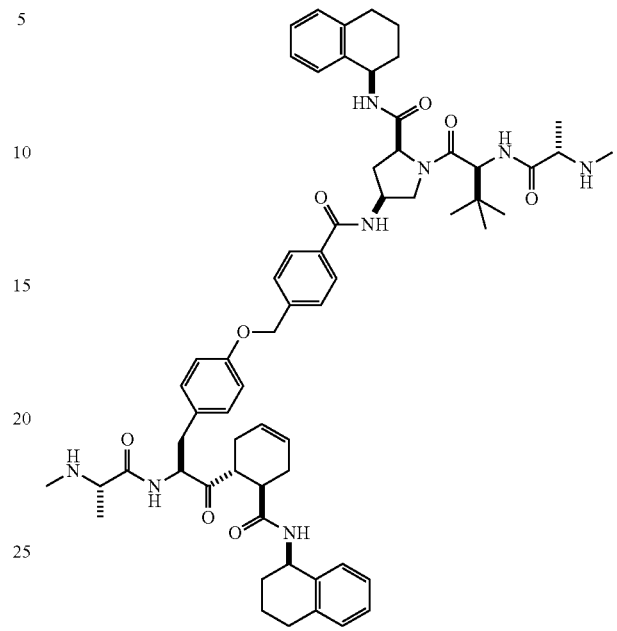

(2S,4S)-1-((S)-3,3-Dimethyl-2-((S)-2-(methylamino)propanamido)butanoyl)-4-(4-((4-((S)-2-((S)-2-(methylamino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzamido)-N—((R)-1,2,3,4-tetrahydronaphthalen-1-yl)pyrrolidine-2-carboxamide

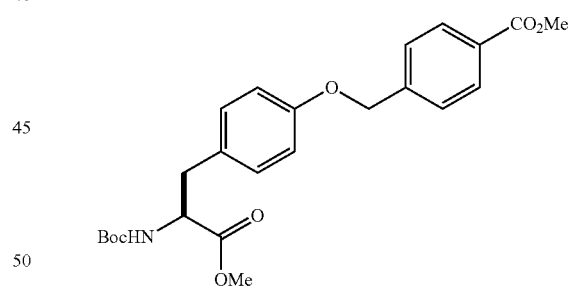

A) (S)-Methyl 4-((4-(2-((tert-butoxycarbonyl)amino)-3-methoxy-3-oxopropyl)phenoxy)methyl)benzoate To a solution of (S)-methyl 2-((tert-butoxycarbonyl)amino)-3-(4-hydroxyphenyl)propanoate (Aldrich, 2.9 g, 10 mmol) and methyl 4-(bromomethyl)benzoate (Aldrich, 2.3 g, 10 mmol) in DMF (10 mL) was added K₂CO₃ (4.2 g, 30 mmol). The resulting reaction mixture was stirred at room temperature for 2 h and then quenched by the addition of cold water (100 mL). The sticky solid that formed was collected by filtration, and purified using flash column chromatography (SiO₂, eluting with CH₂Cl₂) to provide the title compound (3.53 g, 80%) as a light tan solid. ¹H NMR (400 MHz, CDCl$_3$) δ 8.08 (d, J=7.9 Hz, 2H), 7.52 (d, J=7.9 Hz, 2H), 7.07 (d, J=8.1 Hz, 2H), 6.92 (d, J=8.1 Hz, 2H), 5.12 (s, 2H), 5.01 (d, J=7.0 Hz, 1H), 4.57 (d, J=7.0 Hz, 1H), 3.95 (s, 3H), 3.73 (s, 3H), 3.17-2.91 (m, 1H), 1.44 (s, 9H); MS(ESI$^+$) m/z 444.1 (M+H)$^+$.

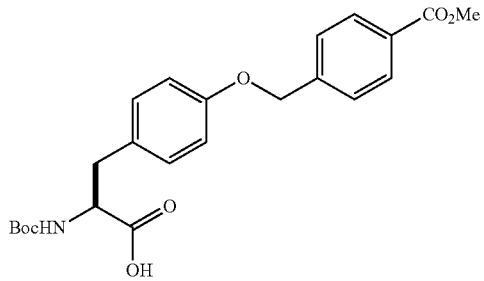

B) (S)-2-((tert-Butoxycarbonyl)amino)-3-(4-((4-(methoxycarbonyl)benzyl)oxy)phenyl)propanoic acid To a solution of (S)-methyl 4-((4-(2-((tert-butoxycarbonyl)amino)-3-methoxy-3-oxopropyl)phenoxy)methyl)benzoate (3.53 g, 7.96 mmol) in THF (15 mL) and MeOH (15 mL) at rt was added LiOH (7.96 mL, 7.96 mmol) dropwise. The reaction mixture was stirred at rt for 2 h, cooled to 0° C. and neutralized to pH 3-4 with 1 N HCl. The mixture was extracted with DCM (3×). The combined organic extracts were dried and concentrated in vacuo and purified by flash column chromatography (SiO$_2$, DCM—EtOAc gradient elution) to provide the title compound (2.84 g, 83%) as a white solid. $^1$H NMR (CDCl$_3$) δ 8.07 (d, J=8.4 Hz, 2H), 7.51 (d, J=8.4 Hz, 2H), 7.14 (d, J=8.6 Hz, 2H), 6.93 (d, J=8.4 Hz, 2H), 5.11 (s, 2H), 5.01 (d, J=6.1 Hz, 1H), 4.61 (d, J=6.1 Hz, 1H), 3.95 (s, 3H), 3.23-3.00 (m, 2H), 1.45 (br s, 9H); MS(ESI$^+$) m/z 430.1 (M+H)$^+$.

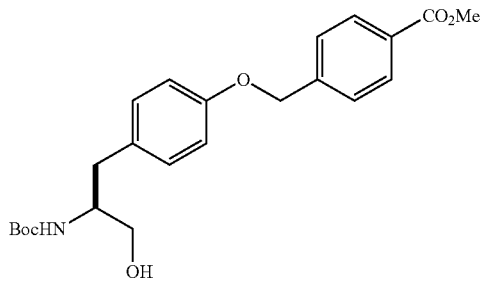

C) (S)-Methyl 4-((4-(2-((tert-butoxycarbonyl)amino)-3-hydroxypropyl)phenoxy)methyl)benzoate To a solution of (S)-2-((tert-butoxycarbonyl)amino)-3-(4-((4-(methoxycarbonyl)benzyl)oxy)phenyl)propanoic acid (1.0 g, 2.3 mmol) in THF (5 mL) at −15° C. (MeOH/wet ice bath) was added NMM (0.47 g, 4.7 mmol) followed by the addition of isobutyl chloroformate (0.61 mL, 4.7 mmol). The reaction mixture was stirred for 10 min. The NMM-HCl precipitate was then removed by vacuum filtration with an oven dried Buchner funnel. The filter cake was washed with THF (2×3 mL). The filtrate was cooled to −15° C. and treated with sodium borohydride (0.26 g, 7.0 mmol) in water (3 mL) rapidly. The mixture was stirred for 20 minutes at −10° C. Additional water was added (5 mL) and the solution was transferred to a separatory funnel and extracted with EtOAc (3×). The organics were combined, dried over sodium sulfate, filtered and concentrated in vacuo. The residue was purified by flash column chromatography (SiO$_2$, DCM—EtOAc gradient elution) to provide the title compound (0.80 g, 83%) as a white solid. $^1$H NMR (CDCl$_3$) δ 8.06 (d, J=8.4 Hz, 2H), 7.50 (d, J=8.4 Hz, 2H), 7.14 (d, J=8.6 Hz, 2H), 6.99-6.83 (m, 2H), 5.11 (s, 2H), 4.72 (m., 1H), 3.93 (s, 3H), 3.73-3.62 (m, 1H), 3.55 (m, 1H), 2.79 (d, J=7.0 Hz, 2H), 1.42 (s, 9H); MS(ESI$^+$) m/z 416.1 (M+H)$^+$.

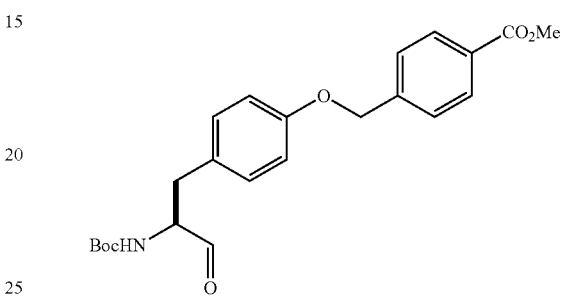

D) (S)-Methyl 4-((4-(2-((tert-butoxycarbonyl)amino)-3-oxopropyl)phenoxy)methyl)benzoate To a solution of (S)-methyl 4-((4-(2-((tert-butoxycarbonyl)amino)-3-hydroxypropyl)phenoxy)methyl)benzoate (0.40 g, 0.96 mmol) in DCM (10 mL) at rt was added Dess-Martin Periodinane (0.61 g, 1.44 mmol). The reaction mixture was stirred at rt for 1 h and quenched by the addition of 20% aq. Na$_2$S$_2$O$_3$ solution (2 mL). The organic layer was washed with brine, dried and concentrated in vacuo. The residue was purified by flash column chromatography (SiO$_2$, DCM—EtOAc gradient elution) to provide the title compound (0.30 g, 75%) as a white solid. $^1$H NMR (CDCl$_3$) δ 9.62 (s, 1H), 8.05 (d, J=8.1 Hz, 2H), 7.48 (d, J=8.1 Hz, 2H), 7.09 (d, J=8.6 Hz, 2H), 6.90 (d, J=8.6 Hz, 2H), 5.28 (s, 1H), 5.09 (s, 2H), 4.39 (m, 1H), 3.91 (s, 3H), 3.06 (d, J=6.2 Hz, 2H), 1.43 (s, 9H); MS(ESI$^+$) m/z 414.1 (M+H)$^+$.

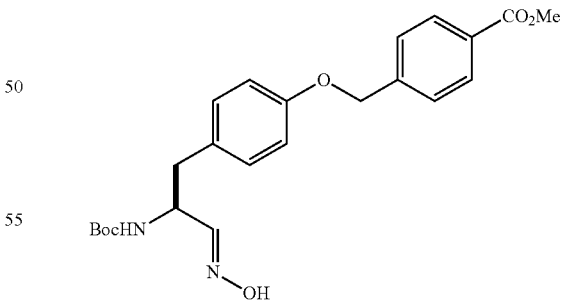

E) (S,E)-Methyl 4-((4-(2-((tert-butoxycarbonyl)amino)-3-(hydroxyimino)propyl)phenoxy)methyl)benzoate To a solution of (S)-methyl 4-((4-(2-((tert-butoxycarbonyl)amino)-3-oxopropyl)phenoxy)methyl)benzoate (0.40 g, 0.97 mmol) in MeOH (5 mL) and water (5 mL) at 0° C. were added hydroxylamine hydrochloride (0.13 g, 1.94 mmol) and sodium carbonate (0.10 g, 0.97 mmol). The reaction mixture was stirred at rt for 4 h and extracted with EtOAc (3×). The combined organic extracts were dried, concentrated, and purified by flash column chromatography (SiO$_2$, DCM—EtOAc gradient elution) to afford the title compound (0.30 g, 75%) as a white solid. $^1$H NMR (CDCl$_3$) δ 9.62 (s, 1H), 8.05 (d, J=8.1 Hz, 2H), 7.48 (d, J=8.1 Hz, 2H), 7.09 (d, J=8.6 Hz, 2H), 6.96-6.83 (m, 2H), 5.09 (s, 2H), 4.39 (m, 1H), 3.91 (s, 3H), 3.06 (d, J=6.2 Hz, 2H), 1.43 (s, 9H); MS(ESI$^+$) m/z 429.2 (M+H)$^+$.

toxycarbonyl)amino)-3-(hydroxyimino)propyl)phenoxy)methyl)benzoate (0.21 g, 0.49 mmol) in EtOAc (3 mL) was added to the solution, followed by sodium hypochlorite (12-15% in water, 0.091 mL, 1.47 mmol). The reaction mixture was gradually warmed to rt and stirred at rt for 2 h. The solid that formed was removed by filtration. The filtrate was diluted with ~EtOAc (50 mL) and washed with aq. KH$_2$PO$_4$ solution. The organic layer was dried over MgSO$_4$, and concentrated in vacuo. The residue was purified by flash column chromatography (SiO$_2$, DCM/EtOAc gradient elution) to afford the title compound (240 mg, 78%) as a tan solid. MS(ESI$^+$) m/z 628.4 (M+H)$^+$.

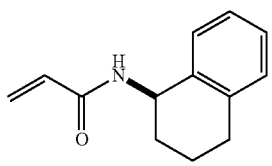

F) (R)—N-(1,2,3,4-Tetrahydronaphthalen-1-yl)acrylamide

To a solution of (R)-1,2,3,4-tetrahydronaphthalen-1-amine and acryloyl chloride (Aldrich, 0.18 g, 2.0 mmol) in DCM (2 mL) at 0° C. were added (R)-1,2,3,4-tetrahydronaphthalen-1-amine (ALFA AESAR®, 0.29 g, 2.0 mmol) and NMM (0.41 g, 4.0 mmol). The reaction mixture was stirred at rt for 30 min and diluted with DCM (30 mL). The organic phase was washed with aq. KH$_2$PO$_4$, solution, dried over MgSO$_4$ and concentrated in vacuo. The residue was purified by flash column chromatography (SiO2, DCM—EtOAc gradient elution) to afford the title compound (0.28 g, 70%) as a white solid. $^1$H NMR (CDCl$_3$) δ 7.35-7.26 (m, 1H), 7.23-7.09 (m, 3H), 6.34 (dd, J=16.9, 1.4 Hz, 1H), 6.19-6.06 (m, 1H), 5.68 (dd, J=10.2, 1.4 Hz, 1H), 5.35-5.23 (m, 1H), 2.91-2.72 (m, 2H), 2.16-2.07 (m, 1H), 1.95-1.82 (m, 3H); MS(ESI$^+$) m/z 202.1 (M+H)$^+$.

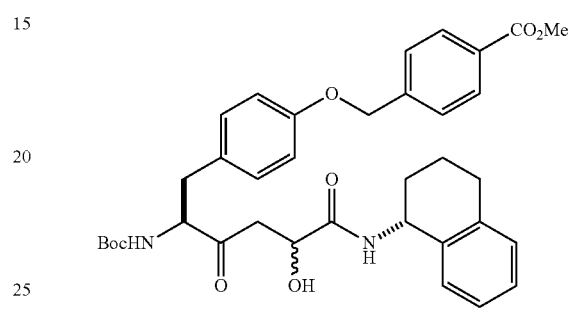

H) Methyl 4-((4-((2S)-2-((tert-butoxycarbonyl)amino)-5-hydroxy-3,6-dioxo-6-(((R)-1,2,3,4-tetrahydronaphthalen-1-yl)amino)hexyl)phenoxy)methyl)benzoate To a stirred solution of methyl 4-((4-((2S)-2-((tert-butoxycarbonyl)amino)-2-(5-(((R)-1,2,3,4-tetrahydronaphthalen-1-yl)carbamoyl)-4,5-dihydroisoxazol-3-yl)ethyl)phenoxy)methyl)benzoate (0.55 g, 0.88 mmol) in MeOH (20 mL) and water (4 mL) were added boric acid (0.16 g, 2.6 mmol) and catalytic amount of Raney-nickel. The mixture was stirred under 1 atm of H$_2$ at rt for 4 h. The reaction mixture was diluted with EtOAc (30 mL) and filtered through CELITE®. The filtrate was then concentrated in vacuo. The residue was purified by preparative HPLC to afford the title compound (300 mg, 54%) as a white solid. MS(ESI$^+$) m/z 631.5 (M+H)$^+$.

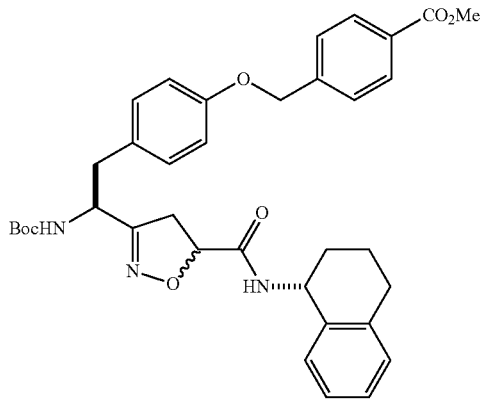

G) Methyl 4-((4-((2S)-2-((tert-butoxycarbonyl)amino)-2-(5-(((R)-1,2,3,4-tetrahydronaphthalen-1-yl)carbamoyl)-4,5-dihydroisoxazol-3-yl)ethyl)phenoxy)methyl)benzoate (R)—N-(1,2,3,4-Tetrahydronaphthalen-1-yl)acrylamide (99 mg, 0.49 mmol) was dissolved in ethyl acetate (2 mL) at 0° C. A suspension of (S,E)-methyl 4-((4-(2-((cert-bu-

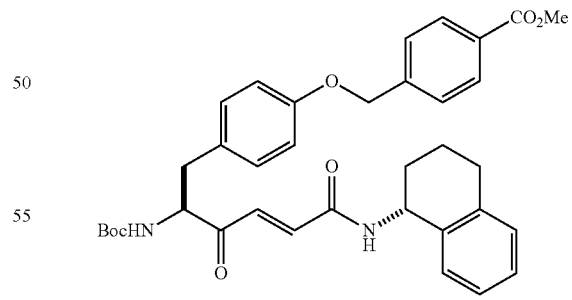

I) Methyl 4-((4-((S,E)-2-((tert-butoxycarbonyl)amino)-3,6-dioxo-6-(((R)-1,2,3,4-tetrahydronaphthalen-1-yl)amino)hex-4-en-1-yl)phenoxy)methyl)benzoate To a solution of methyl 4-((4-((2S)-2-((tert-butoxycarbonyl)amino)-5-hydroxy-3,6-dioxo-6-(((R)-1,2,3,4-tetrahydronaphthalen-1-yl)amino)hexyl)phenoxy)methyl)benzoate (0.30 g, 0.48 mmol) in pyridine (5 mL) at 0° C. was added methanesulfonyl chloride (0.19 mL, 2.4 mmol). The reaction mixture was stirred at 0° C. for 1 h and at rt for 3 h. The reaction mixture was diluted with EtOAc (50 mL) and washed with 5% aq. citric acid solution and brine. The organic layer was dried, concentrated, and purified by flash column chromatography (SiO$_2$, DCM/EtOAc gradient elution) to provide the title compound (152 mg, 52%) as a light yellow solid. MS(ESI$^+$) m/z 557.3 (M+H)$^+$.

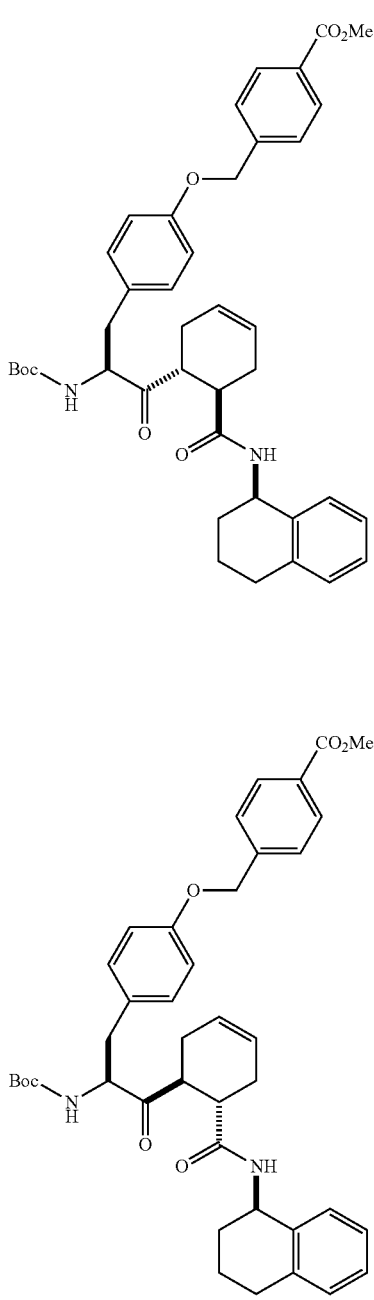

J) Methyl 4-((4-((S)-2-((tert-butoxycarbonyl) amino)-3-oxo-3-((1R,6R)-6-(((R)-1,2,3,4-tetrahydronaphthalen-1-yl)carbamoyl)cyclohex-3-en-1-yl) propyl)phenoxy)methyl)benzoate (ISOMER A)

Methyl 4-((4-((S)-2-((tert-butoxycarbonyl)amino)-3-oxo-3-((1S,6S)-6-(((R)-1,2,3,4-tetrahydronaphthalen-1-yl)carbamoyl)cyclohex-3-en-1-yl)propyl)phenoxy)methyl)benzoate (ISOMER B)

A resealable glass tube was charged with methyl 4-((4-((S,E)-2-((tert-butoxycarbonyl)amino)-3,6-dioxo-6-(((R)-1,2,3,4-tetrahydronaphthalen-1-yl)amino)hex-4-en-1-yl)phenoxy)methyl)benzoate (0.10 g, 0.16 mmol), toluene (5 mL) and buta-1,3-diene (15% in hexane, 0.59 mg, 1.63 mmol). The tube was sealed and the reaction mixture was heated at 95° C. for 6 h. The reaction mixture was concentrated in vacuo to give a crude oil as a 5:1 mixture of diastereomers. The diastereomers were separated using prep HPLC: the major product was assigned as ISOMER A (60 mg, 55%), and the minor product was assigned as ISOMER B (15 mg, 14%). MS(ESI$^+$) m/z 667.5 (M+H)$^+$ for both.

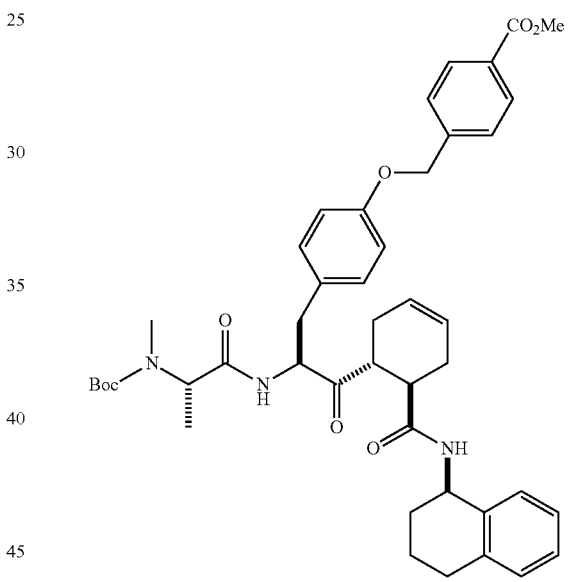

K) Methyl 4-((4-((S)-2-((S)-2-((tert-butoxycarbonyl)(methyl)amino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzoate To a solution of ISOMER A (60 mg, 0.090 mmol) in DCM (2.0 mL) was added TFA (0.5 mL). The reaction mixture was stirred at rt for 1 h and concentrated in vacuo to give a foaming solid (51 mg, 100%), which was used directly in the next step. MS(ESI$^+$) m/z 567.5 (M+H)$^+$.

To a solution of the above product (51 mg, 0.09 mmol) in DMF (1 mL) were added HOAt (28 mg, 0.18 mmol), EDC (35 mg, 0.18 mmol), NMM (36 mg, 0.36 mmol) and (S)-2-((tert-butoxycarbonyl)(methyl)amino)propanoic acid (37 mg, 0.18 mmol). The resulting reaction mixture was stirred at room temperature for 1 h and purified by preparative HPLC to give the title compound (53 mg, 78%) as a white solid. MS(ESI$^+$) m/z 752.6 (M+H)$^+$.

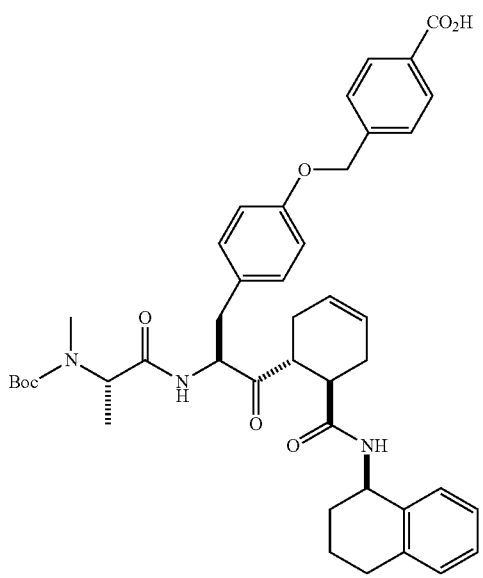

L) 4-((4-((S)-2-((S)-2-((tert-Butoxycarbonyl)(methyl)amino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzoic acid To a solution of methyl 4-((4-((S)-2-((S)-2-((tert-butoxycarbonyl)(methyl) amino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzoate (53 mg, 0.070 mmol) in THF (1 mL) and MeOH (1 mL) was added 2N NaOH (0.35 mL, 0.70 mmol). The reaction mixture was stirred at rt for 2 h, cooled to 0° C. and neutralized to pH 3-4 with 1N HCl. The mixture was then extracted with DCM (3×). The combined organic layers were dried and concentrated in vacuo. The residue was purified by preparative HPLC to give the title compound as a white solid (47 mg, 90%).

M) N-Boc Precursor I

To a solution of 4-((4-((S)-2-((S)-2-((tert-butoxycarbonyl)(methyl)amino) propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzoic acid (14 mg, 0.019 mmol) in DMF (1 mL) were added HATU (15 mg, 0.039 mmol), DIEA (10 µl, 0.058 mmol) and methyl 4-((4-((S,E)-2-((tert-butoxycarbonyl)amino)-3,6-dioxo-6-(((R)-1,2,3,4-tetrahydronaphthalen-1-yl)amino)hex-4-en-1-yl)phenoxy)methyl)benzoate (18 mg, 0.039 mmol). The reaction mixture was stirred at room temperature for 2 h and purified by preparative HPLC to give the N-Boc Precursor I as a white solid (14 mg, 57%). MS(ESL+) m/z 1277.8 (M+H)$^+$.

N) (2S,4S)-1-((S)-3,3-Dimethyl-2-((S)-2-(methylamino)propanamido)butanoyl)-4-(4-((4-((S)-2-((S)-2-(methylamino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzamido)-N—((R)-1,2,3,4-tetrahydronaphthalen-1-yl)pyrrolidine-2-carboxamide To a solution of N-Boc Precursor I in DCM (1.5 mL) was added TFA (0.5 mL). The reaction mixture was stirred at rt for 1 h and concentrated in vacuo. The residue was dissolved in CH$_3$CN/H$_2$O and lyophilized to dryness to give the title compound as a white solid (10 mg, 81%). MS(ESI$^+$) m/z 1077.8 (M+H)$^+$.

Example 10

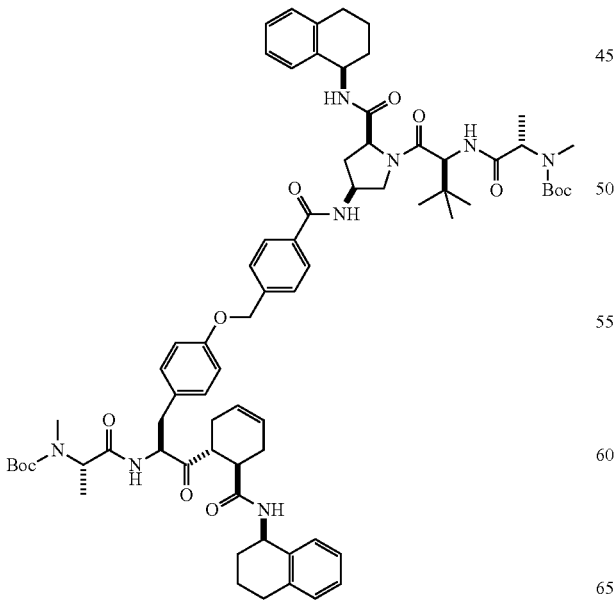

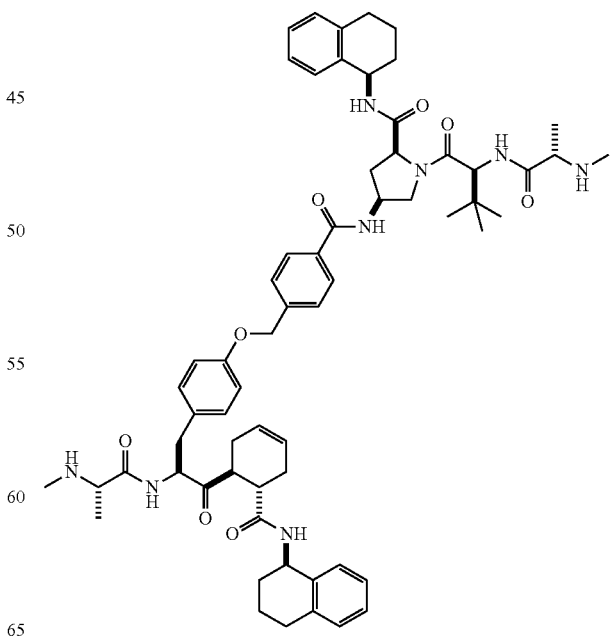

(2S,4S)-1-((S)-3,3-Dimethyl-2-((S)-2-(methylamino)
propanamido)butanoyl)-4-(4-((4-((S)-2-((S)-2-
(methylamino)propanamido)-3-oxo-3-((1S,6S)-6-
(((R)-1,2,3,4-tetrahydronaphthalen-1-yl)carbamoyl)
cyclohex-3-en-1-yl)propyl)phenoxy)methyl)
benzamido)-N—((R)-1,2,3,4-tetrahydronaphthalen-
1-yl)pyrrolidine-2-carboxamide Following procedures analogous to those for the synthesis of Example 9, ISOMER B (Compound J of Example 9, 15 mg, 0.022 mmol) was converted to the title compound. MS(ESI⁺) m/z 1077.8 (M+H)⁺.

Example 11

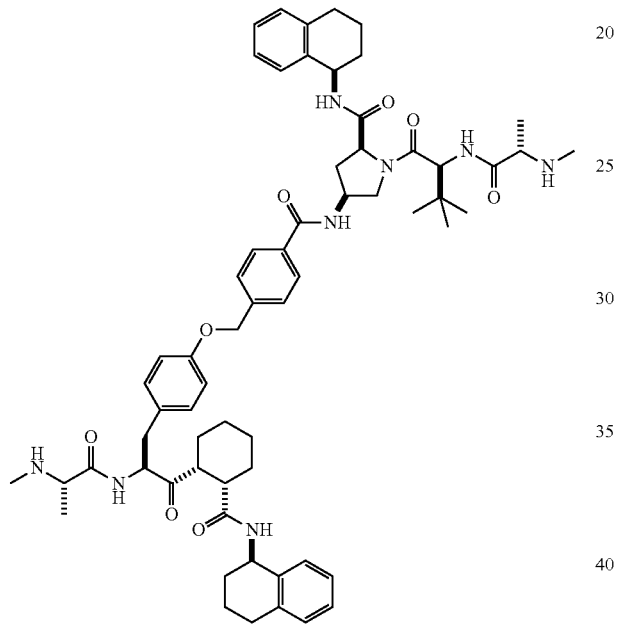

(2S,4S)-1-((S)-3,3-Dimethyl-2-((S)-2-(methylamino)
propanamido)butanoyl)-4-(4-((4-((S)-2-((S)-2-
(methylamino)propanamido)-3-oxo-3-((1R,2R)-2-
(((R)-1,2,3,4-tetrahydronaphthalen-1-yl)carbamoyl)
cyclohexyl)propyl)phenoxy)methyl)benzamido)-N—
((R)-1,2,3,4-tetrahydronaphthalen-1-yl)pyrrolidine-
2-carboxamide To a solution (2S,4S)-1-((S)-3,3-dimethyl-2-((S)-2-(methylamino)propanamido)butanoyl)-4-(4-((4-((S)-2-((S)-2-(methylamino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzamido)-N—((R)-1,2,3,4-tetrahydronaphthalen-1-yl)pyrrolidine-2-carboxamide (Example 9, 5.0 mg, 4.6 μmol) in i-PrOH (2.0 mL) was added Pd/C (2.0 mg, 0.019 mmol). The reaction mixture was stirred at rt under H₂ balloon for 3 h and filtered through a pad of CELITE®. The filtrate was concentrated and lyophilized to dryness to give the title compound as a white solid (5 mg, 90%). MS(ESI⁺) m/z 1079.9 (M+H)⁺.

Example 12

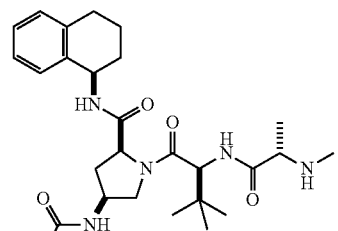

(2S,4S)-1-((S)-3,3-Dimethyl-2-((S)-2-(methylamino)
propanamido)butanoyl)-4-(4-((4-((S)-2-((S)-2-
(methylamino)propanamido)-3-oxo-3-((1S,2S)-2-
(((R)-1,2,3,4-tetrahydronaphthalen-1-yl)carbamoyl)
cyclohexyl)propyl)phenoxy)methyl)benzamido)-N—
((R)-1,2,3,4-tetrahydronaphthalen-1-yl)pyrrolidine-
2-carboxamide Following a procedure analogous to that for the synthesis of Example 11, (2S,4S)-1-((S)-3,3-dimethyl-2-((S)-2-(methylamino)propanamido)butanoyl)-4-(4-((4-((S)-2-((S)-2-(methylamino)propanamido)-3-oxo-3-((1S,6S)-6-(((R)-1,2,3,4-tetrahydronaphthalen-1-yl)carbamoyl)cyclohex-3-en-1-yl)propyl)phenoxy)methyl)benzamido)-N—((R)-1,2,3,4-tetrahydronaphthalen-1-yl)pyrrolidine-2-carboxamide (Example 10, 5.0 mg, 4.64 μmol) was converted to the title compound (5 mg, 90%). MS(ESI⁺) m/z 1080.4 (M+H)⁺.

Example 13

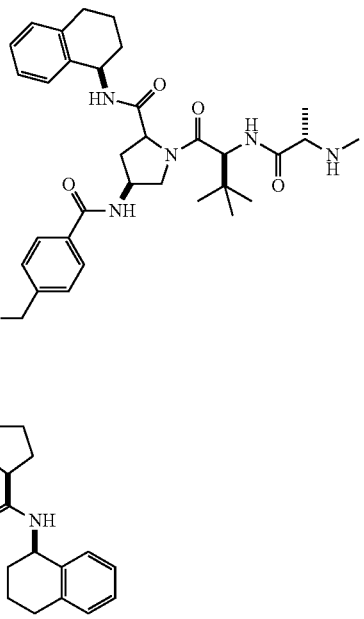

((4S)-1-((S)-3,3-Dimethyl-2-((S)-2-(methylamino) propanamido)butanoyl)-4-(4-((4-((2-((S)-2-(methyl-amino)propanoyl)-1-((1R,2R)-2-(((R)-1,2,3,4-tetra-hydronaphthalen-1-yl)carbamoyl) cyclopentanecarbonyl)hydrazinyl)methyl)phenoxy) methyl)benzamido)-N—((R)-1,2,3,4-tetrahydronaphthalen-1-yl)pyrrolidine-2-carboxamide

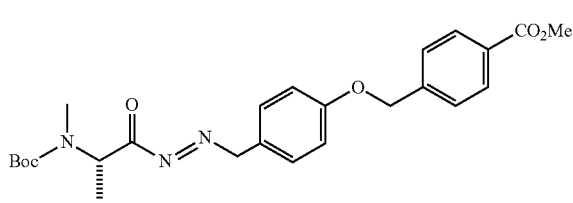 [SMILES: COC(=O)c1ccc(COc2ccc(C/N=N/C(=O)[C@H](C)N(C)C(=O)OC(C)(C)C)cc2)cc1]

A) (S,E)-Methyl 4-((4-(((2-((tert-butoxycarbonyl) (methyl)amino)propanoyl)diazenyl)methyl)phenoxy) methyl)benzoate To a solution of (S)-2-((tert-butoxycarbonyl)(methyl) amino)propanoic acid (Chem-Impex, 1.0 g, 5.0 mmol) and hydrazine (0.48 g, 15 mmol) in DMF (8.0 mL) were added EDC (1.2 g, 6.5 mmol), HOAt (1.0 g, 6.5 mmol) and NMM (1.5 g, 15 mmol). The resulting reaction mixture was stirred at room temperature for 2 h, diluted with cold water and extracted with EtOAc (3×). The combined organic extracts were dried and concentrated in vacuo to give a thick colorless oil, which was used directly in the next step. MS(ESI⁺) m/z 240.2 (M+Na)⁺.

To the solution of the above intermediate in DCM (20 mL) were added methyl 4-((4-formylphenoxy)methyl)benzoate (ALFA AESAR®, 1.1 g, 4.1 mmol), 4-methylbenzenesulfonic acid (0.71 g, 4.1 mmol) and 4 Å molecular sieves (1 g). The reaction mixture was stirred at room temperature overnight and diluted with DCM (100 mL). The organic solution was washed with aq. $K_2HPO_4$ solution, dried and concentrated in vacuo. The residue was purified by flash column chromatography ($SiO_2$, DCM/EtOAc gradient elution) to give the desired product as a white foam (890 mg, 38% for two steps). MS(ESI⁺) m/z 470.3 (M+H)⁺.

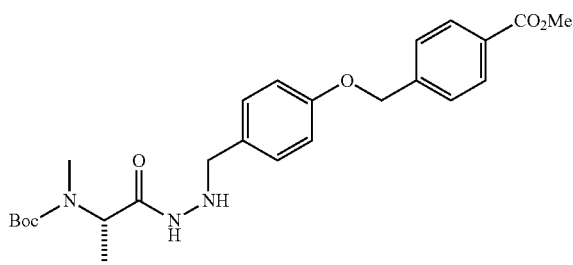 [SMILES: COC(=O)c1ccc(COc2ccc(CNNC(=O)[C@H](C)N(C)C(=O)OC(C)(C)C)cc2)cc1]

B) (S)-Methyl 4-((4-((2-(2-((tert-butoxycarbonyl) (methyl)amino)propanoyl) hydrazinyl)methyl)phenoxy)methyl)benzoate To a solution of (S,E)-methyl 4-((4-(((2-((tert-butoxycarbonyl)(methyl)amino)propanoyl)diazenyl)methyl)phenoxy) methyl)benzoate (80 mg, 0.17 mmol) in 2-propanol (10 mL) was added and Pd/C (50% wet, 8.1 mg, 0.17 mmol). The resulting reaction mixture was degassed and stirred under 1 atm $H_2$ at room temperature for 1 h. The reaction mixture was degassed to remove $H_2$ and diluted with EtOAc (30 mL). The mixture was filtered through a pad of CELITE® and the filtrate was concentrated in vacuo. The residue was purified by preparative HPLC and the appropriate fractions were lyophilized to give a white solid (41 mg, 51%). MS(ESI⁺) m/z 472.3 (M+H)⁺.

ISOMER A

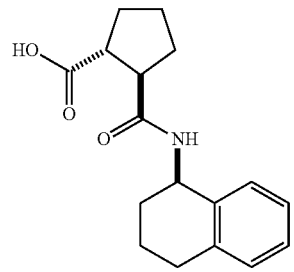

ISOMER B

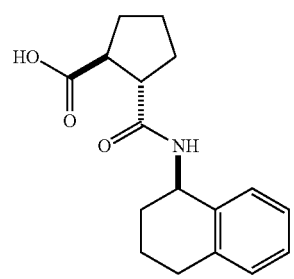

C) (1R,2R)-2-(((R)-1,2,3,4-tetrahydronaphthalen-1-yl)carbamoyl)cyclopentanecarboxylic acid (ISOMER A)

(1S,2S)-2-(((R)-1,2,3,4-tetrahydronaphthalen-1-yl) carbamoyl)cyclopentanecarboxylic acid (ISOMER B)

To a solution of trans-DL-cyclopentane-1,2-dicarboxylic acid (0.11 g, 0.70 mmol) in DMF (2 mL) were added HOAt (0.13 g, 0.84 mmol), EDC (0.16 g, 0.84 mmol), 4-methylmorpholine (0.21 mg, 2.1 mmol) and (R)-1,2,3,4-tetrahydronaphthalen-1-amine (0.10 g, 0.70 mmol). The resulting reaction mixture was stirred at room temperature for 1 h. The mixture of trans-isomers was then separated by preparative HPLC: the faster eluting product was assigned as ISOMER A (70 mg, 35%), and the slower eluting product was assigned as ISOMER B (40 mg, 14%). MS(ESI⁺) m/z 288.2 (M+H)⁺ for both.

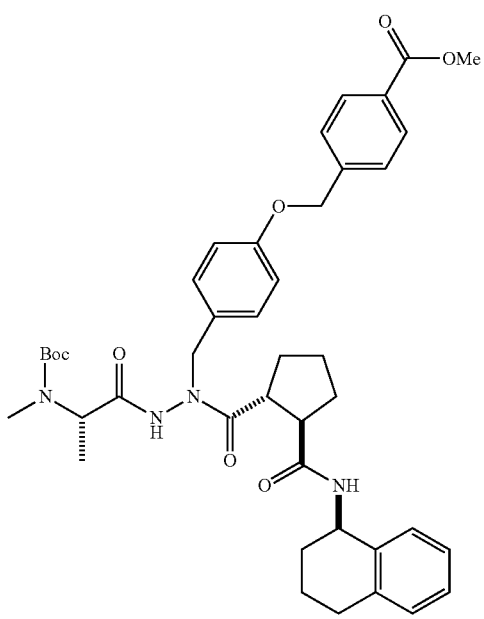

D) Methyl 4-((4-((2-((S)-2-((tert-butoxycarbonyl)(methyl)amino)propanoyl)-1-((1R,2R)-2-(((R)-1,2,3,4-tetrahydronaphthalen-1-yl)carbamoyl)cyclopentanecarbonyl)hydrazinyl)methyl)phenoxy)methyl)benzoate To a solution of (1R,2R)-2-(((R)-1,2,3,4-tetrahydronaphthalen-1-yl)carbamoyl)cyclopentanecarboxylic acid (ISOMER A, 46 mg, 0.16 mmol) in DMF (1 mL) were added HATU (61 mg, 0.16 mmol) and DIEA (0.056 mL, 0.32 mmol). The reaction mixture was stirred at rt for 10 min and treated with a solution of (S)-methyl 4-((4-((2-(2-((tert-butoxycarbonyl)(methyl)amino)propanoyl)hydrazinyl)methyl)phenoxy) methyl)benzoate (Compound A, 50 mg, 0.11 mmol) in DMF. The resulting reaction mixture was stirred at room temperature for 2 h. The reaction was quenched by adding cold water (10 mL). The desired product was precipitated and the solid was collected by filtration (80 mg, 100%). MS(ESI$^+$) m/z 741.5 (M+H)$^+$.

E) ((4S)-1-((S)-3,3-Dimethyl-2-((S)-2-(methylamino)propanamido)butanoyl)-4-(4-((4-((2-((S)-2-(methylamino)propanoyl)-1-((1R,2R)-2-(((R)-1,2,3,4-tetrahydronaphthalen-1-yl)carbamoyl)cyclopentanecarbonyl)hydrazinyl)methyl)phenoxy)methyl)benzamido)-N—((R)-1,2,3,4-tetrahydronaphthalen-1-yl)pyrrolidine-2-carboxamide To a solution of methyl 4-((4-((2-((S)-2-((tert-butoxycarbonyl)(methyl)amino) propanoyl)-1-((1R,2R)-2-(((R)-1,2,3,4-tetrahydronaphthalen-1-yl)carbamoyl)cyclopentanecarbonyl)hydrazinyl)methyl)-phenoxy)methyl)benzoate (15 mg, 0.020 mmol) in THF (0.5 mL) and MeOH (0.5 mL) was added 2N NaOH (0.11 mL, 0.20 mmol). The reaction mixture was stirred at rt for 4 h, cooled to 0° C., neutralized to pH 3-4 with 1.0 N HCl, and extracted with DCM (3×). The combined organic extracts were dried and concentrated to give a white solid, which was used directly in the next step.

The above compound (14 mg, 0.019 mmol) in DMF (1.0 ml) were added HATU (14.7 mg, 0.039 mmol), DIEA (10.1 µl, 0.058 mmol) and the compound from Example I (18.2 mg, 0.039 mmol). The resulting reaction mixture was stirred at room temperature for 2 h and quenched by the addition of cold water (5 mL). The desired product was precipitated as a solid and was collected by filtration (14 mg, 57%). MS(ESI$^+$) m/z 1266.7 (M+H)$^+$.

To a solution of the above compound (14 mg, 0.011 mmol), in DCM (1.5 mL) was added TFA (0.5 mL). The reaction mixture was stirred at rt for 1 h and concentrated in vacuo. The residue was purified by preparative HPLC and lyophilized to dryness to give the title compound as a white solid (8 mg, 68%). MS(ESI$^+$) m/z 1066.6 (M+H)$^+$.

Example 14

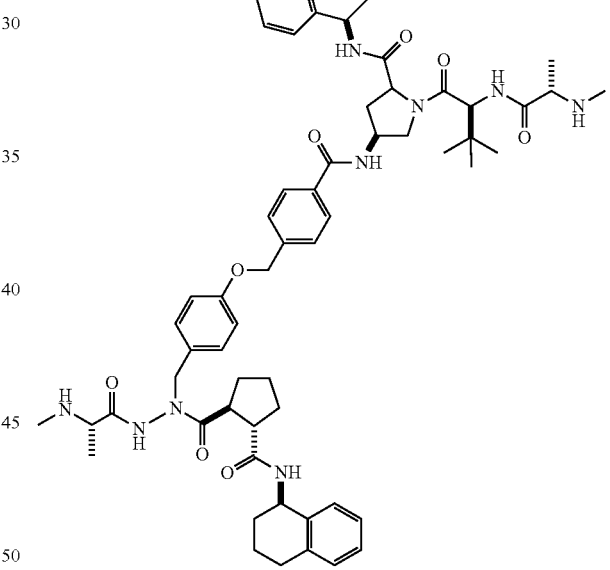

(4S)-1-((S)-3,3-Dimethyl-2-((S)-2-(methylamino)propanamido)butanoyl)-4-(4-((4-((2-((S)-2-(methylamino)propanoyl)-1-((1S,2S)-2-(((R)-1,2,3,4-tetrahydronaphthalen-1-yl)carbamoyl)cyclopentanecarbonyl)hydrazinyl)methyl)phenoxy)methyl)benzamido)-N—((R)-1,2,3,4-tetrahydronaphthalen-1-yl)pyrrolidine-2-carboxamide Following procedures analogous to those for the synthesis of Example 13, ISOMER B (Compound B of Example 13, 40 mg, 0.024 mmol) was converted to the title compound. MS(ESI$^+$) m/z 1066.6 (M+H)$^+$.

Example 15

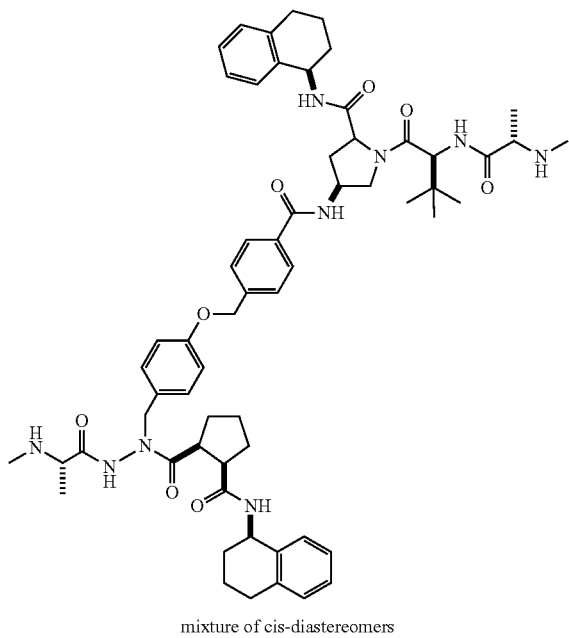

mixture of cis-diastereomers (4S)-1-((S)-3,3-Dimethyl-2-((S)-2-(methylamino) propanamido)butanoyl)-4-(4-((4-((2-((S)-2-(methyl-amino)propanoyl)-1-((1S,2R)-2-(((R)-1,2,3,4-tetra-hydronaphthalen-1-yl)carbamoyl) cyclopentanecarbonyl)hydrazinyl)methyl)phenoxy) methyl)benzamid)-N—((R)-1,2,3,4-tetrahydronaphthalen-1-yl)pyrrolidine-2-carboxamide

A) (1R,2S)-2-(((R)-1,2,3,4-Tetrahydronaphthalen-1-yl)carbamoyl)cyclopentanecarboxylic acid

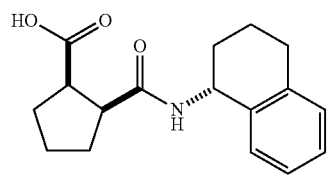

mixture of cis-diastereomers

To a solution of cis-2-carbomethoxy cyclopentane-1-carboxylic acid (RIEKE®, 400 mg, 2.32 mmol) in DMF (4 ml) were added HATU (1.06 g, 2.79 mmol), and DIEA (1.22 ml, 6.97 mmol). The reaction mixture was stirred at rt for 10 min and treated with (R)-1,2,3,4-tetrahydronaphthalen-1-amine (ALFA AESAR®, 342 mg, 2.32 mmol) in 1 mL of DMF. The resulting reaction mixture was stirred at room temperature for 2 h and quenched by the addition of cold water (50 mL). The solid that formed was collected by filtration, and purified by flash column chromatography (SiO$_2$, DCM/EtOAc gradient elution) to afford the title compound (320 mg, 46%) as a white solid. MS(ESI$^+$) m/z 302.1 (M+H)$^+$.

To a solution of the above compound (80 mg, 0.11 mmol) in THF (1 mL) and MeOH (1 mL) was added 2N NaOH (0.32 mL, 0.65 mmol). The reaction mixture was stirred at rt until no starting material was observed based on LCMS. The reaction mixture was cooled to 0° C., neutralized to pH 3-4 with 1N HCl, and extracted with DCM (3×). The combined organic extracts were dried, concentrated and purified by preparative HPLC to give the title compound (70 mg, 89%) as a white solid. MS(ESI$^+$) m/z 288.2 (M+H)$^+$.

B) (4S)-1-((S)-3,3-Dimethyl-2-((S)-2-(methylamino) propanamido)butanoyl)-4-(4-((4-((2-((S)-2-(methyl-amino)propanoyl)-1-((1S,2R)-2-(((R)-1,2,3,4-tetra-hydronaphthalen-1-yl)carbamoyl) cyclopentanecarbonyl)hydrazinyl)methyl)phenoxy) methyl)benzamido)-N—((R)-1,2,3,4-tetrahydronaphthalen-1-yl)pyrrolidine-2-carboxamide Using Compound A as starting material and following procedures analogous to those for the synthesis of Example 13, the title compound was prepared as a mixture of cis-diastereomers. MS(ESI$^+$) m/z 1066.6 (M+H)$^+$.

Example 16

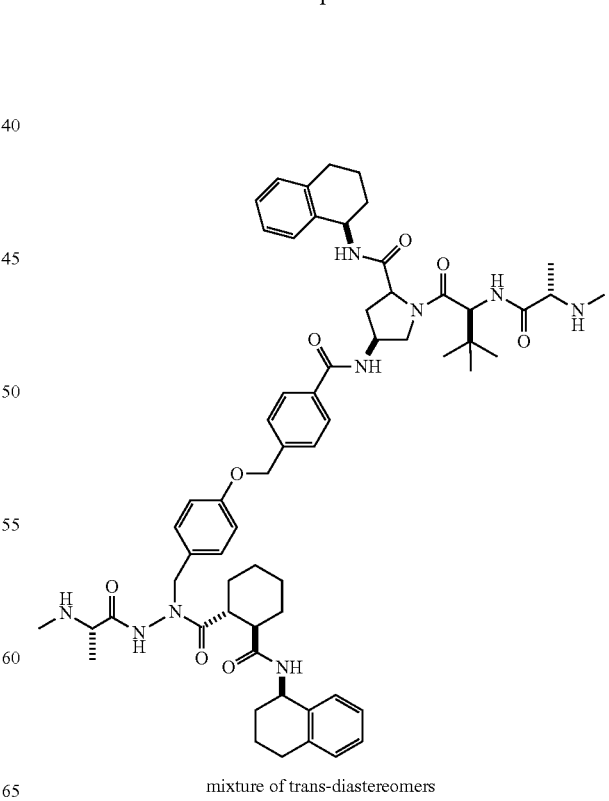

mixture of trans-diastereomers (4S)-1-((S)-3,3-Dimethyl-2-((S)-2-(methylamino)
propanamido)butanoyl)-4-(4-((4-((2-((S)-2-(methyl-
amino)propanoyl)-1-((1R,2R)-2-(((R)-1,2,3,4 tetra-
hydronaphthalen-1-yl)carbamoyl)
cyclohexanecarbonyl)hydrazinyl)methyl)phenoxy)
methyl)benzamido)-N—((R)-1,2,3,4-
tetrahydronaphthalen-1-yl)pyrrolidine-2-
carboxamide Example 17

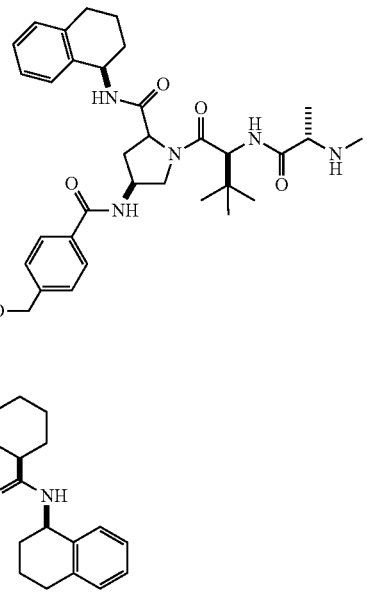

mixture of cis-diastereomers

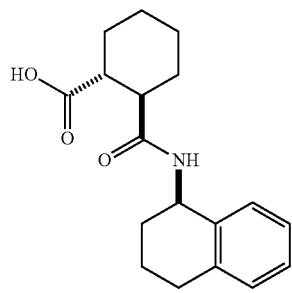

mixture of trans-diastereomers

A) (1R,2R)-2-(((R)-1,2,3,4-Tetrahydronaphthalen-1-
yl)carbamoyl)cyclohexanecarboxylic acid To a solution of trans-1,2-cyclohexane dicarboxylic anhydride (Aldrich, 0.31 g, 2.0 mmol) in DCM (5 mL) was added (R)-1,2,3,4-tetrahydronaphthalen-1-amine (0.294 g, 2.0 mmol). The reaction mixture was stirred at rt for 1 h and diluted with DCM (50 mL). The organic layer was washed with water and aq. $KH_2PO_4$ solution, dried and concentrated in vacuo. The residue was purified by flash column chromatography ($SiO_2$, DCM/MeOH gradient elution) to provide the title compound (458 mg, 76%) as a tan solid. MS(ESI$^+$) m/z 302.1 (M+H)$^+$.

B) (4S)-1-((S)-3,3-Dimethyl-2-((S)-2-(methylamino)
propanamido)butanoyl)-4-(4-((4-((2-((S)-2-(methyl-
amino)propanoyl)-1-((1R,2R)-2-(((R)-1,2,3,4-tetra-
hydronaphthalen-1-yl)carbamoyl)
cyclohexanecarbonyl)hydrazinyl)methyl)phenoxy)
methyl)benzamido)-N—((R)-1,2,3,4-
tetrahydronaphthalen-1-yl)pyrrolidine-2-
carboxamide The title compound was prepared as a mixture of trans-diastereomers by using Compound A as starting material and following procedures analogous to those for the synthesis of Example 13. MS(ESI$^+$) m/z 1080.7 (M+H)$^+$.

(4S)-1-((S)-3,3-Dimethyl-2-((S)-2-(methylamino)
propanamido)butanoyl)-4-(4-((4-((2-((S)-2-(methyl-
amino)propanoyl)-1-((1S,2R)-2-(((R)-1,2,3,4-tetra-
hydronaphthalen-1-yl)carbamoyl)
cyclohexanecarbonyl)hydrazinyl)methyl)phenoxy)
methyl)benzamido)-N—((R)-1,2,3,4-
tetrahydronaphthalen-1-yl)pyrrolidine-2-
carboxamide

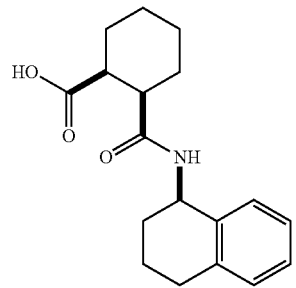

mixture of cis-diastereomers

A) ((1S,2R)-2-(((R)-1,2,3,4-Tetrahydronaphthalen-
1-yl)carbamoyl)cyclohexanecarboxylic acid To a solution of cis-1,2-cyclohexane dicarboxylic anhydride (Aldrich, 0.31 g, 2.0 mmol) in DCM (5 mL) were added (S)-1,2,3,4-tetrahydronaphthalen-1-amine (0.29 g, 2.0 mmol) and DIEA (0.87 mL, 5.0 mmol). The reaction mixture was stirred at rt for 1 h and diluted with DCM (50 mL). The organic layer was washed with water and aq. $KH_2PO_4$, dried and concentrated in vacuo. The residue was purified by flash column chromatography ($SiO_2$, DCM/

MeOH gradient elution) to provide the title compound (458 mg, 76%) as a tan solid. MS(ESI⁺) m/z 302.1 (M+H)⁺.

B) (4S)-1-((S)-3,3-Dimethyl-2-((S)-2-(methylamino)propanamido)butanoyl)-4-(4-((4-((2-((S)-2-(methylamino)propanoyl)-1-((1S,2R)-2-(((R)-1,2,3,4-tetrahydronaphthalen-1-yl)carbamoyl)cyclohexanecarbonyl)hydrazinyl)methyl)phenoxy)methyl)benzamido)-N—((R)-1,2,3,4-tetrahydronaphthalen-1-yl)pyrrolidine-2-carboxamide The title compound was prepared as a mixture of cis-diastereomers by using Compound A as starting material and following procedures analogous to those for the synthesis of Example 13. MS(ESI⁺) m/z 1080.7 (M+H)⁺.

Example 18

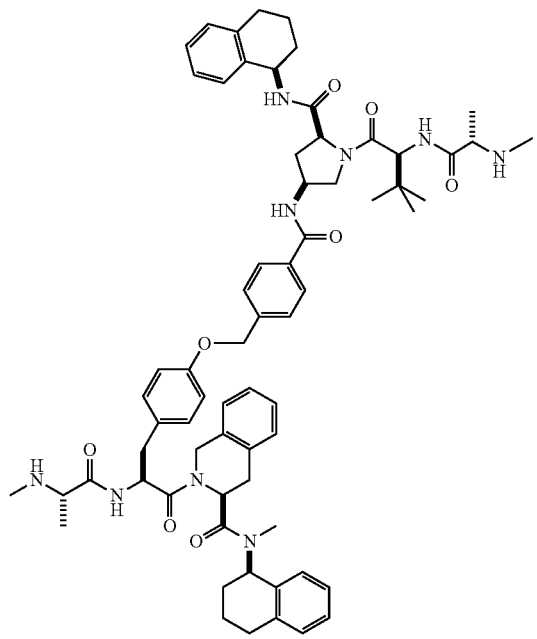

(S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanoyl)propanoyl)-N-methyl-N—((R)-1,2,3,4-tetrahydronaphthalen-1-yl)-1,2,3,4-tetrahydroisoquinoline-3-carboxamide

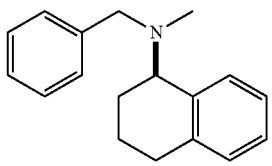

A) (R)—N-Benzyl-N-methyl-1,2,3,4-tetrahydronaphthalen-1-amine

To a solution of (R)-1,2,3,4-tetrahydronaphthalen-1-amine (0.59 g, 4.0 mmol) in DCM (10 mL) and 2-propanol (5 mL) were added benzaldehyde (0.42 g, 4.0 mmol) and sodium triacetoxyborohydride (1.27 g, 6.00 mmol). The reaction mixture was stirred at rt for 2 h. The reaction was quenched by adding 2 mL of MeOH and aq. K₂HPO₄. The reaction mixture was extracted with DCM (3×). The combined organic extracts were dried, concentrated in vacuo and used in the next reaction without purification. MS(ESI⁺) m/z 238.2 (M+H)⁺.

To a solution of the above compound in DCM (10 mL) and 2-propanol (5 mL) were added formaldehyde (417 mg, 5.00 mmol) and sodium triacetoxyborohydride (795 mg, 3.75 mmol). The reaction mixture was stirred at rt for 2 h and quenched by adding 2 mL of MeOH and aq. K₂HPO₄. The reaction mixture was extracted with DCM (3×). The combined organic extracts were dried, concentrated in vacuo and purified using flash column chromatography (0 to 20% EtOAc/DCM gradient elution) to provide the title compound (380 mg, 61% over two steps) as a light yellow solid. ¹H NMR (CDCl₃) δ 8.06 (d, J=7.7 Hz, 1H), 7.59 (d, J=7.5 Hz, 2H), 7.49 (t, J=7.5 Hz, 2H), 7.43-7.34 (m, 2H), 7.30 (t, J=7.3 Hz, 1H), 7.24-7.20 (m, 1H), 4.18-4.09 (m, 1H), 3.91-3.82 (m, 1H), 3.78-3.69 (m, 1H), 3.02-2.83 (m, 2H), 2.37 (s, 3H), 2.24-2.12 (m, 2H), 2.00-1.82 (m, 2H); MS(ESI⁺) m/z 252.2 (M+H)⁺.

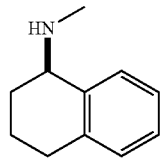

B) (R)—N-Methyl-1,2,3,4-tetrahydronaphthalen-1-amine

To a solution of (R)—N-benzyl-N-methyl-1,2,3,4-tetrahydronaphthalen-1-amine (380 mg, 1.51 mmol) in MeOH (5.0 mL) and EtOAc (2.0 mL) was added Pd/C (64.4 mg, 0.30 mmol). The reaction mixture was shaken on a Parr shaker at 30 psi for 2 h and then 10.0 mL of EtOAc was added. The reaction mixture was filtered through a pad of CELITE®. The filtrate was concentrated in vacuo and purified by preparative HPLC to provide the title compound (80 mg, 33%) as a white solid. ¹H NMR (CDCl₃) δ 8.06 (d, J=7.7 Hz, 1H), 7.59 (d, J=7.5 Hz, 2H), 7.49 (t, J=7.5 Hz, 2H), 7.43-7.34 (m, 2H), 7.30 (t, J=7.3 Hz, 1H), 7.24-7.20 (m, 1H), 4.18-4.09 (m, 1H), 3.91-3.82 (m, 1H), 3.78-3.69 (m, 1H), 3.02-2.83 (m, 2H), 2.37 (s, 3H), 2.24-2.12 (m, 2H), 2.00-1.82 (m, 2H); MS(ESI⁺) m/z 162.1 (M+H)⁺.

C) (S)-tert-Butyl 3-(methyl((R)-1,2,3,4-tetrahydronaphthalen-1-yl)carbamoyl)-3,4-dihydroisoquinoline-2(1H)-carboxylate

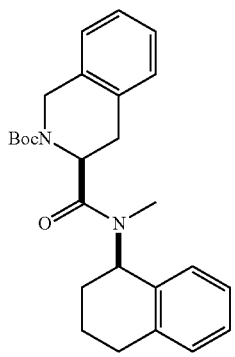

To a solution of (S)-2-(tert-butoxycarbonyl)-1,2,3,4-tetrahydroisoquinoline-3-carboxylic acid (ALFA AESAR®, 172 mg, 0.620 mmol) in DMF (3.0 mL) were added BOP (357 mg, 0.81 mmol) and NMM (251 mg, 2.48 mmol). The reaction mixture was stirred at rt for 10 min, and then a solution of (R)—N-methyl-1,2,3,4-tetrahydronaphthalen-1-amine (Compound B, 100 mg, 0.62 mmol) in DMF (1.0 mL) was added. The reaction mixture was stirred at rt for 4 h and quenched by adding ~30 mL of cold water. The solid that formed was collected by filtration, and purified using flash column chromatography (0 to 50% EtOAc/DCM gradient elution) to provide the title compound (110 mg, 42%) as a thick colorless oil. MS(ESI$^+$) m/z 421.3 (M+H)$^+$.

D) (S)—N-Methyl-N—((R)-1,2,3,4-tetrahydronaphthalen-1-yl)-1,2,3,4-tetrahydroisoquinoline-3-carboxamide

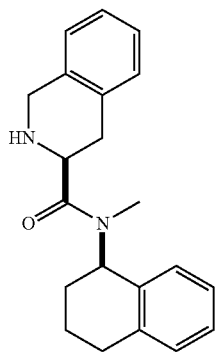

To a solution of (S)-tert-butyl 3-(methyl((R)-1,2,3,4-tetrahydronaphthalen-1-yl)carbamoyl)-3,4-dihydroisoquinoline-2(1H)-carboxylate (110 mg, 0.26 mmol) in DCM (5.0 mL) at rt was added HCl, 4 M in 1,4-dioxane (1.31 mL, 5.23 mmol). The reaction mixture was stirred at rt for 2 h, and concentrated in vacuo to give the title compound (83 mg, 99%) as a light yellow solid. MS(ESI$^+$) m/z 321.2 (M+H)$^+$.

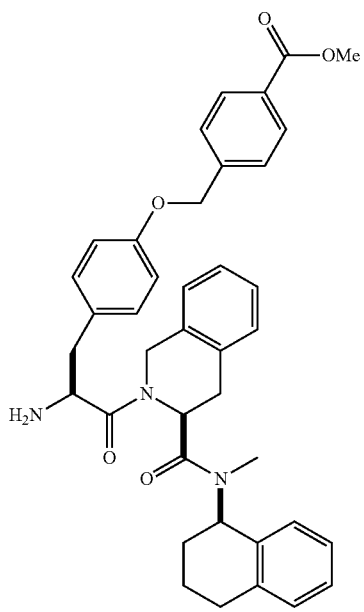

E) Methyl 4-((4-((S)-2-amino-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoate To a solution of (S)-2-((tert-butoxycarbonyl)amino)-3-(4-((4-(methoxycarbonyl)benzyl)oxy)phenyl)propanoic acid (Compound A of Example 9) (0.13 g, 0.31 mmol) in DMF (2.0 mL) at rt under nitrogen was added HOAt (0.060 g, 0.39 mmol), EDC (0.075 g, 0.39 mmol) and NMM (0.079 g, 0.78 mmol). The reaction mixture was stirred at rt for 20 min, and then a solution of (S)—N-methyl-N—((R)-1,2,3,4-tetrahydronaphthalen-1-yl)-1,2,3,4-tetrahydroisoquinoline-3-carboxamide (Compound D, 0.083 g, 0.26 mmol) in DMF (1.0 mL) was added. The mixture was then stirred under nitrogen for 2 h and then quenched with 20 mL of cold water. The solid that formed was collected by filtration and dried under vacuum. MS(ESI$^+$) m/z 732.4 (M+H)$^+$.

To a solution of the above compound (0.17 g, 0.23 mmol) in DCM (5.0 mL) at rt was added HCl, 4 M in 1,4-dioxane (1.15 mL, 4.60 mmol). The reaction mixture was stirred at rt for 2 h and then concentrated in vacuo to give the title compound (83 mg, 88% over two steps) as a light yellow solid. MS(ESI$^+$) m/z 632.3 (M+H)$^+$.

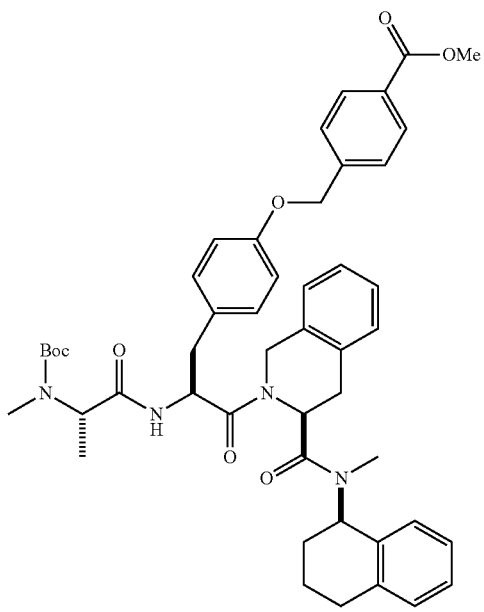

F) Methyl 4-((4-((S)-2-((S)-2-((tert-butoxycarbonyl)(methyl)amino)propanamido)-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoate To a solution of (S)-2-((tert-butoxycarbonyl)(methyl)amino)propanoic acid (Chem-Impex, 0.056 g, 0.28 mmol) in DMF (2.0 mL) were added HOAt (0.053 g, 0.34 mmol), EDC (0.066 g, 0.34 mmol) and NMM (0.070 g, 0.69 mmol). The reaction mixture was stirred at rt for 20 min, and then a solution of methyl 4-((4-((S)-2-amino-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoate (Compound E, 0.14 g, 0.23 mmol) in DMF (1.0 mL) was added. The mixture was stirred under nitrogen for 2 h and then quenched with 20 mL of cold water. The solid that formed was collected by filtration and purified using flash column chromatography (0 to 50% EtOAc/DCM gradient elution) to provide the title compound (163 mg, 87%) as a light yellow solid. MS(ESI+) m/z 817.4 (M+H)+.

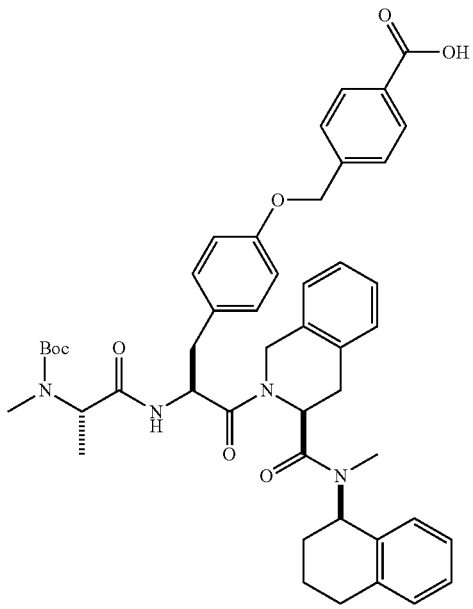

G) 4-((4-((S)-2-((S)-2-((tert-Butoxycarbonyl)(methyl)amino)propanamido)-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoic acid To a solution of methyl 4-((4-((S)-2-((S)-2-((tert-butoxycarbonyl)(methyl)amino)propanamido)-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoate (0.16 g, 0.20 mmol) in MeOH (1.0 mL) and THF (1.0 mL) was added 2N NaOH (0.30 mL, 0.60 mmol). The reaction was stirred at rt for 7 h and then cooled to 0° C. The reaction mixture was neutralized to pH 3-4 with 1N HCl and extracted with DCM (3×). The combined organic extracts were dried, concentrated in vacuo and purified by prep HPLC to give the title compound (70 mg, 44%) as a white solid. MS(ESI+) m/z 803.5 (M+H)+.

H) (S)-2-((S)-3-(4-((4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)benzyl)oxy)phenyl)-2-((S)-2-(methylamino)propanamido)propanoyl)-N-methyl-N—((R)-1,2,3,4-tetrahydronaphthalen-1-yl)-1,2,3,4-tetrahydroisoquinoline-3-carboxamide To a solution of 4-((4-((S)-2-((S)-2-((tert-butoxycarbonyl)(methyl)amino)propanamido)-3-((S)-3-(methyl((R)-1,2,3,4-tetrahydronaphthalen-1-yl)carbamoyl)-3,4-dihydroisoquinolin-2(1H)-yl)-3-oxopropyl)phenoxy)methyl)benzoic acid (70 mg, 0.087 mmol) in DMF (1.0 mL) at rt were added HATU (50 mg, 0.13 mmol) and DIEA (0.030 mL, 0.17 mmol), followed by the addition of a homogeneous solution of tert-butyl ((S)-1-((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D of Example 1, 49 mg, 0.087 mmol) in DMF (0.5 mL). The reaction mixture was stirred at rt for 2 h and then purified by preparative HPLC to give a white solid (82 mg, 70%). MS(ESI+) m/z 1342.6 (M+H)+.

To a solution of the above compound (82 mg, 0.061 mmol) in DCM (1.0 mL) was added TFA (0.5 mL). The reaction mixture was stirred at rt for 1 h, and then concentrated in vacuo. The residue was purified by prep HPLC to provide the title compound (47 mg, 67%) as a white solid. MS(ESI+) m/z 1142.6 (M+H)+.

Example 19

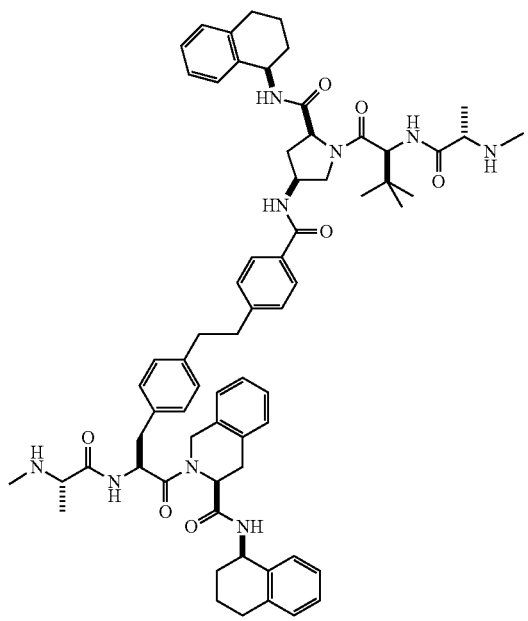

(S)-2-((S)-3-(4-(4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)phenethyl)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide, 2 TFA

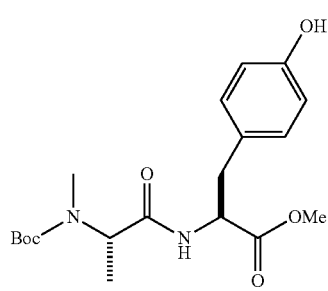 [SMILES: COC(=O)[C@H](Cc1ccc(O)cc1)NC(=O)[C@H](C)N(C)C(=O)OC(C)(C)C]

A) (S)-Methyl 2-((S)-2-(tert-butoxycarbonyl(methyl)amino)propanamido)-3-(4-hydroxyphenyl)propanoate Boc-N-Me-Ala-OH (Matrix Scientific, 0.877 g, 4.32 mmol), EDC (0.993 g, 5.18 mmol) and HOAt (Advanced ChemTech, 0.705 g, 5.18 mmol) were dissolved in DMF (10 mL) and the reaction mixture stirred at rt for 10 minutes. The reaction mixture was cooled to 0° C. and was then treated with L-tyrosine methyl ester hydrochloride (1.00 g, 4.32 mmol) followed by NMM (1.42 mL, 13.0 mmol). The resulting reaction mixture was stirred at 0° C. for 15 minutes then allowed to warm to rt and stirred at rt for 1 h. The reaction mixture was then quenched with 10% aq. LiCl solution and the resulting solution was extracted with ethyl acetate (3×). The combined organic extracts were washed with 10% aq. LiCl solution (3×) and 1N HCl (1×). The organic fraction was dried, filtered and concentrated in vacuo to afford the product that was used directly in the next step. $^1$H NMR (DMSO-$d_6$) δ 9.18 (s, 1H), 8.00 (d, J=7.7 Hz, 1H), 6.97 (d, J=8.4 Hz, 2H), 6.71-6.54 (m, 2H), 4.38 (d, J=5.5 Hz, 2H), 3.30 (s, 3H), 3.00-2.72 (m, 2H), 1.98 (s, 3H), 1.55-1.25 (m, 9H), 1.22-0.94 (m, 3H); MS(ESI$^+$) m/z 381.3 (M+H)$^+$.

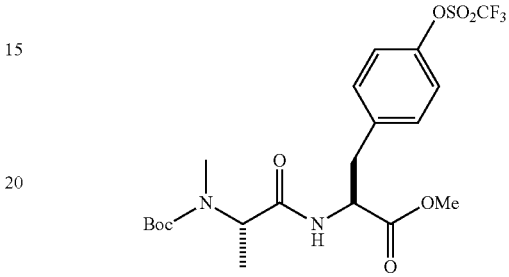

B) (S)-Methyl 2-((S)-2-(tert-butoxycarbonyl(methyl)amino)propanamido)-3-(4-(trifluoromethyl-sulfonyloxy)phenyl)propanoate Trifluoromethanesulfonic acid anhydride (407 mL, 2.42 mmol) was added to a mixture of (S)-methyl 2-((S)-2-(tert-butoxycarbonyl(methyl)amino)propanamido)-3-(4-hydroxyphenyl)propanoate (0.80 g, 2.1 mmol) and pyridine (0.850 mL, 10.5 mmol) in DCM (10 mL) at 0° C. The reaction mixture was then stirred at 0° C. for 30 minutes, then was treated with triflic anhydride (1.5 eq.) and pyridine (5 eq.). The reaction mixture was then stirred at 0° C. for 30 minutes. The reaction mixture was quenched with 1 NaOH and the solution extracted with CHCl$_3$ (3×). The combined organic fractions were then washed with 10% aq. citric acid solution. The organic fraction was dried, filtered and concentrated in vacuo. The residue was purified by flash column chromatography (SiO2, eluting with 2/1 ethyl acetate/hexane) to afford the product. MS(ESI$^-$) m/z 511.4 (M−H)$^-$

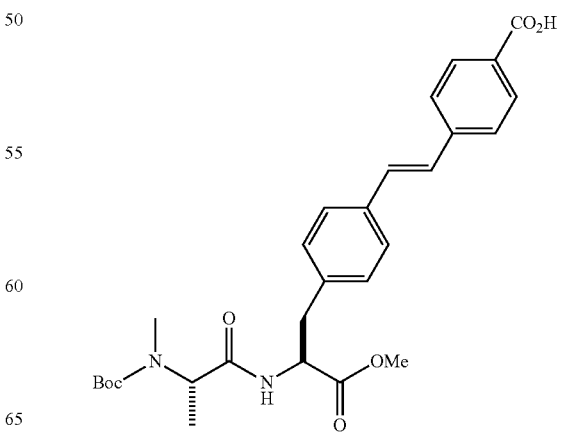

C) 4-((E)-4-((S)-2-((S)-2-((tert-Butoxycarbonyl) (methyl)amino)propanamido)-3-methoxy-3-oxopropyl)styryl)benzoic acid (S)-Methyl 2-((S)-2-(tert-butoxycarbonyl(methyl)amino) propanamido)-3-(4-(trifluoromethylsulfonyloxy)phenyl) propanoate (0.20 g, 0.39 mmol), palladium (II) acetate (8.8 mg, 0.039 mmol), tetrabutylammonium chloride hydrate (0.13 g, 0.47 mmol), potassium carbonate (0.27 g, 1.95 mmol), tri-o-tolylphosphine (0.024 g, 0.078 mmol) and p-vinylbenzoic acid (0.087 g, 0.56 mmol) were stirred in a solution of DMF (5 mL), degassed with argon and heated to 90° C. overnight. The reaction mixture was quenched with 10% aq. LiCl solution and the resulting was solution extracted with ethyl acetate (3×). The combined organic extracts were washed with 10% aq. LiCl solution and the organic fraction was washed with 1N HCl (1×). The organic fraction was dried, filtered and concentrated in vacuo. The residue was purified by C-18 reverse phase preparative HPLC (eluting 63-90% aq. MeOH with 0.1% TFA over a 30 minute gradient). The appropriate fractions were isolated and concentrated in vacuo. The residue was further dried by azeotroping with methanol and toluene. The solid was further dried under high vacuum to afford the product as a solid. $^1$H NMR (CDCl$_3$) δ 8.08 (dd, J=8.4, 1.8 Hz, 2H), 7.57 (dd, J=8.5, 2.1 Hz, 2H), 7.46 (dd, J=7.8, 5.2 Hz, 2H), 7.23-6.99 (m, 4H), 4.97-4.83 (m, 1H), 4.72 (br. s., 1H), 3.84-3.66 (m, 3H), 3.28-2.96 (m, 2H), 2.82-2.46 (m, 3H), 1.58-1.40 (m, 9H), 1.36-1.17 (m, 3H); MS(ESI$^-$) m/z 509.6 (M–H)$^-$.

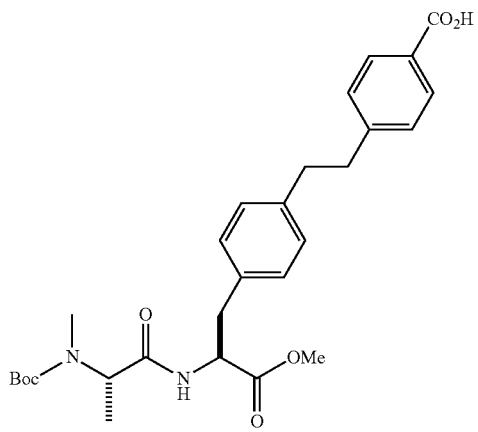 [SMILES: COC(=O)[C@H](Cc1ccc(CCc2ccc(C(=O)O)cc2)cc1)NC(=O)[C@H](C)N(C)C(=O)OC(C)(C)C]

D) 4-(4-((S)-2-((S)-2-((tert-Butoxycarbonyl) (methyl)amino)propanamido)-3-methoxy-3-oxopropyl)phenethyl)benzoic acid 4-((E)-4-((S)-2-((S)-2-((tert-Butoxycarbonyl)(methyl) amino)-propanamido)-3-methoxy-3-oxopropyl)styryl)benzoic acid (0.018 g, 0.035 mmol) and 10% palladium on carbon (3.75 mg, 0.035 mmol) were stirred in ethanol (1 mL) under 1 atm hydrogen for 1 h. The reaction mixture was filtered through CELITE® and the filtrate concentrated in vacuo. The residue was further dried under high vacuum and the product was used directly in the next reaction. MS(ESI$^+$) m/z 513.3 (M+H)$^+$.

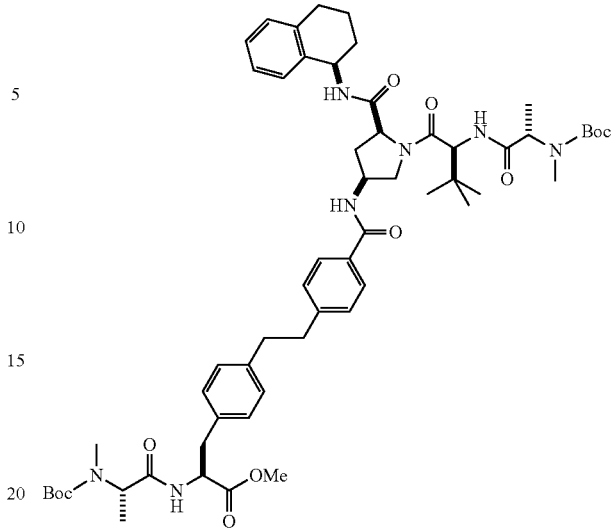

E) (S)-Methyl 2-((S)-2-((tert-Butoxycarbonyl) (methyl)amino)propanamido)-3-(4-(4-(((3S,5S)-1-((S)-2-((S)-2-((tert-butoxycarbonyl)(methyl)amino) propanamido)-3,3-dimethylbutanoyl)-5-(((R)-1,2,3, 4-tetrahydronaphthalen-1-yl)carbamoyl)pyrrolidin-3-yl)carbamoyl)phenethyl)phenyl)propanoate 4-(4-((S)-2-((S)-2-((tert-Butoxycarbonyl)(methyl)amino) propanamido)-3-methoxy-3-oxopropyl)phenethyl)benzoic acid (0.017 g, 0.033 mmol) was dissolved in DMF (1 mL) along with HOAt (5.42 mg, 0.040 mmol) and N1-((ethylimino)methylene)-N3,N3-dimethylpropane-1,3-diamine hydrochloride (7.63 mg, 0.040 mmol) at rt and the reaction mixture was stirred for 15 minutes. The reaction mixture was then cooled to 0° C. and tert-butyl ((S)-1-(((S)-1-((2S, 4S)-4-amino-2-(((R)-1,2,3,4-tetrahydronaphthalen-1-yl)carbamoyl)pyrrolidin-1-yl)-3,3-dimethyl-1-oxobutan-2-yl) amino)-1-oxopropan-2-yl)(methyl)carbamate (Compound D of Example 1, 0.018 g, 0.033 mmol) was added followed by 4-methylmorpholine (11 µl, 0.099 mmol). The reaction mixture was stirred at 0° C. for 30 minutes and then allowed to warm to rt and stirred for 2 h. The reaction mixture was quenched with 10% aq. LiCl solution and the resulting solution was extracted with ethyl acetate (3×). The combined organic extracts were washed with 10% aq. LiCl solution (3×) and 10% aq. citric acid solution (1×). The organic fraction was dried, filtered and concentrated in vacuo to afford the product, which was used directly in the next reaction. $^1$H NMR (CD$_3$OD) δ 8.74 (br. s., 1H), 8.61 (d, J=8.8 Hz, 1H), 8.43 (d, J=8.4 Hz, 1H), 7.98 (s, 1H), 7.87-7.69 (m, 2H), 7.60-7.21 (m, 3H), 7.17-6.89 (m, 4H), 5.21-4.99 (m, 1H), 4.79-4.46 (m, 5H), 4.19-4.01 (m, 1H), 3.93-3.81 (m, 1H), 3.77-3.54 (m, 3H), 3.20-3.07 (m, 1H), 3.04-2.69 (m, 9H), 2.66-2.44 (m, 2H), 2.17-1.73 (m, 7H), 1.56-1.16 (m, 27H), 1.10-0.77 (m, 9H); MS(ESI$^+$) m/z 1052.8 (M+H)$^+$.

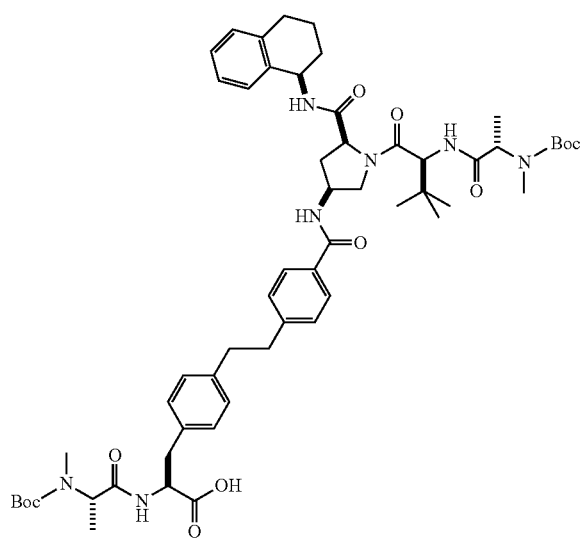

F) (S)-2-((S)-2-((tert-Butoxycarbonyl)(methyl)
amino)propanamido)-3-(4-(4-(((3S,5S)-1-((S)-2-
((S)-2-((tert-butoxycarbonyl)(methyl)amino)pro-
panamido)-3,3-dimethylbutanoyl)-5-(((R)-1,2,3,4-
tetrahydronaphthalen-1-yl)carbamoyl)pyrrolidin-3-
yl)carbamoyl)phenethyl)phenyl)propanoic acid (S)-Methyl 2-((S)-2-((tert-butoxycarbonyl)(methyl)
amino)propanamido)-3-(4-(4-(((3S,5S)-1-((S)-2-((S)-2-
((tert-butoxycarbonyl)(methyl)amino)propanamido)-3,3-di-
methylbutanoyl)-5-(((R)-1,2,3,4-tetrahydronaphthalen-1-yl)
carbamoyl)pyrrolidin-3-yl)carbamoyl)phenethyl)phenyl)
propanoate (0.034 g, 0.032 mmol) was dissolved in 1/1
MeOH (0.5 mL)/THF (0.5 mL) and the resulting solution
was treated with LiOH (0.081 mL, 0.162 mmol, 2N) at rt.
The resulting reaction mixture was stirred at rt for 1 h. The
reaction mixture was quenched with 1N HCl and the result-
ing solution was extracted with CHCl₃ (3×). The combined
organic extracts were dried, filtered and concentrated in
vacuo to afford the product that was used without further
purification. MS(ESI⁺) m/z 1038.8 (M+H)⁺.

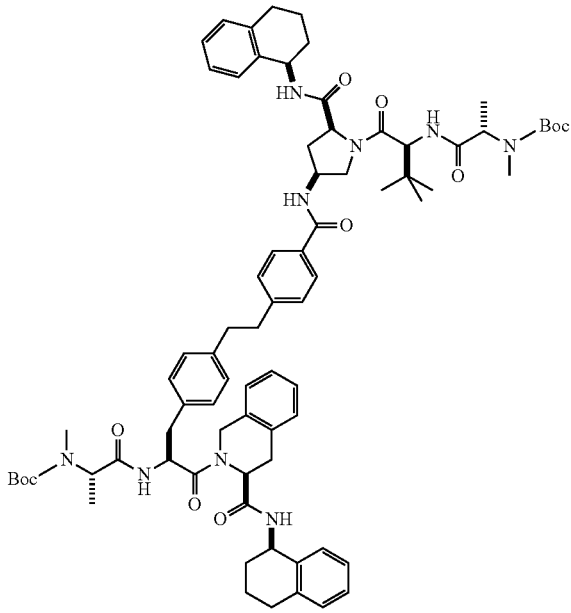

G) N-Boc-Precursor (S)-2-((S)-2-((tert-Butoxycarbonyl)(methyl)amino)pro-
panamido)-3-(4-(4-(((3S,5S)-1-((S)-2-((S)-2-((tert-butoxy-
carbonyl)(methyl)amino)propanamido)-3,3-dimethylbu-
tanoyl)-5-(((R)-1,2,3,4-tetrahydronaphthalen-1-yl)
carbamoyl)pyrrolidin-3-yl)carbamoyl)phenethyl)phenyl)
propanoic acid (0.033 g, 0.032 mmol), 3H-[1,2,3]triazolo[4,
5-b]pyridin-3-ol (5.19 mg, 0.038 mmol) and N1-
((ethylimino)methylene)-N3,N3-dimethylpropane-1,3-
diamine hydrochloride (7.31 mg, 0.038 mmol) were stirred
at 0° C. in a solution of DMF (1 mL) for 10 minutes.
(S)—N—((R)-1,2,3,4-tetrahydronaphthalen-1-yl)-1,2,3,4-
tetrahydroisoquinoline-3-carboxamide (0.012 g, 0.038
mmol) followed by NMM (10.5 µl, 0.095 mmol) were then
added and the resulting reaction mixture was stirred at 0° C.
for 15 minutes. The mixture was allowed to warm to rt and
stirred for 1 h. The reaction mixture was quenched with 10%
aq. LiCl solution and the resulting solution extracted with
ethyl acetate (3×). The combined organic extracts were
washed with 10% aq. LiCl solution (3×). The organic
fraction was dried, filtered and concentrated in vacuo to
afford the product, which was used directly in the next
reaction. MS(ESI⁺) m/z 1326.1 (M+H)⁺.

H) (S)-2-((S)-3-(4-(4-(((3S,5S)-1-((S)-3,3-Dimethyl-
2-((S)-2-(methylamino)propanamido)butanoyl)-5-
(((R)-1,2,3,4-tetrahydronaphthalen-1-yl)carbamoyl)
pyrrolidin-3-yl)carbamoyl)phenethyl)phenyl)-2-((S)-
2-(methylamino)propanamido)propanoyl)-N—((R)-
1,2,3,4-tetrahydronaphthalen-1-yl)-1,2,3,4-
tetrahydroisoquinoline-3-carboxamide, 2 TFA The N-Boc-precursor (0.043 g, 0.032 mmol) was dis-
solved in DCM (0.5 mL) and the resulting solution was
treated with HCl (0.446 mL, 1.78 mmol, 4M in dioxane).
The reaction mixture was stirred at rt for 1 h and concen-
trated in vacuo. The residue was purified by C18 reverse
phase preparative HPLC (eluting with 63-90% aq MeOH
over a 30 minute gradient). The appropriate fractions were
isolated and concentrated in vacuo. The residue was dis-
solved in methanol and azeotroped with toluene (3×). The
solid was then dissolved in aq. CH₃CN and freeze dried to
afford the product as a TFA salt lyophilate. ¹H NMR
(CD₃OD) δ 8.63-8.51 (m, 1H), 8.41 (d, J=7.9 Hz, 1H),
7.86-7.67 (m, 2H), 7.41 (d, J=7.7 Hz, 1H), 7.35-6.80 (m,
17H), 5.15-5.08 (m, 1H), 5.03-4.94 (m, 1H), 4.77-4.70 (m,
1H), 4.67-4.48 (m, 3H), 4.45-4.35 (m, 1H), 4.18-4.04 (m,
2H), 3.99-3.79 (m, 4H), 3.73 (q, J=7.1 Hz, 1H), 3.26-3.12
(m, 2H), 3.07-2.50 (m, 14H), 2.43-2.33 (m, 1H), 2.21-1.55
(m, 13H), 1.52-1.34 (m, 8H), 1.06 (s, 9H); MS(ESI⁺) m/z
1126.1 (M+H)⁺.

Example 20

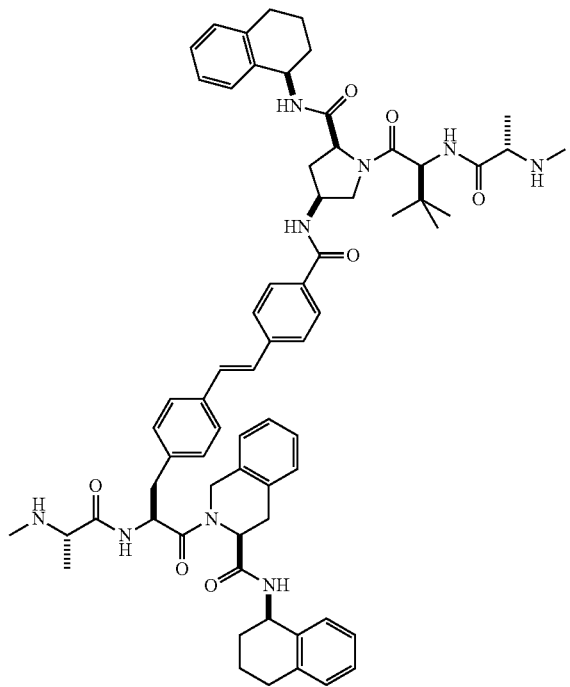

(S)-2-((S)-3-(4-((E)-4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)styryl)phenyl)-2-((S)-2-(methylamino)propanamido)propanoyl)-N—((R)-1,2,3,4-tetrahydronaphthalen-1-yl)-1,2,3,4-tetrahydroisoquinoline-3-carboxamide, 2 TFA

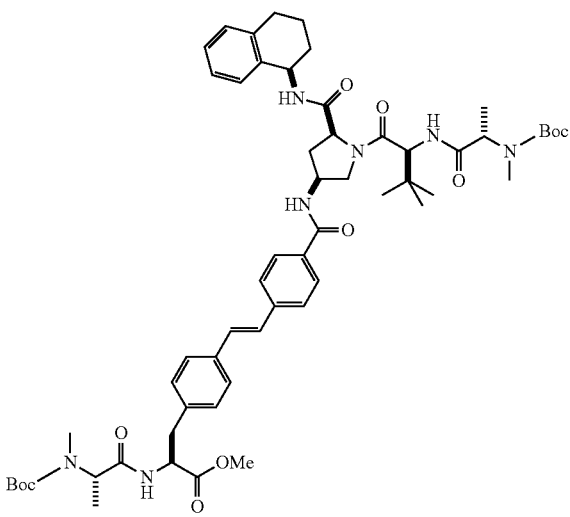

A) (S)-Methyl 2-((S)-2-((tert-butoxycarbonyl)(methyl)amino)propanamido)-3-(4-((E)-4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)styryl)phenyl)propanoate 4-((E)-4-((S)-2-((S)-2-((tert-Butoxycarbonyl)(methyl)amino)-propanamido)-3-methoxy-3-oxopropyl)styryl)benzoic acid (Compound C of Example 19, 0.018 g, 0.035 mmol), 3H-[1,2,3]triazolo[4,5-b]pyridin-3-ol (5.76 mg, 0.042 mmol) and N1-((ethylimino)methylene)-N3,N3-dimethylpropane-1,3-diamine hydrochloride (8.11 mg, 0.042 mmol) were stirred in DMF (1 mL) at rt for 10 min. The reaction mixture was cooled to 0° C. and tert-butyl ((S)-1-(((S)-1-((2S,4S)-4-amino-2-(((R)-1,2,3,4-tetrahydronaphthalen-1-yl)carbamoyl)pyrrolidin-1-yl)-3,3-dimethyl-1-oxobutan-2-yl)amino)-1-oxopropan-2-yl)(methyl)carbamate (Compound D of Example 1, 0.020 g, 0.035 mmol) followed by NMM (0.012 mL, 0.11 mmol) was added and the resulting reaction mixture was stirred at 0° C. for 30 minutes. The reaction mixture was allowed to warm to rt and stirred for 2 h. The reaction mixture was then quenched with 10% aq. LiCl solution and the resulting solution was extracted with ethyl acetate (3x). The combined organic extracts were washed with 10% aq. LiCl solution (3x) and 1N HCl (1x). The organic fraction was dried, filtered and concentrated in vacuo to afford the product, which was used without further purification. $^1$H NMR (CD$_3$OD) δ 8.64 (d, J=8.8 Hz, 1H), 7.95-7.80 (m, 2H), 7.74-7.50 (m, 2H), 7.48-7.47 (m, 2H), 7.45-6.96 (m, 7H), 5.18-4.98 (m, 1H), 4.78-4.44 (m, 3H), 4.20-4.01 (m, 1H), 3.91 (dd, J=10.6, 3.3 Hz, 1H), 3.79-3.63 (m, 3H), 3.29-3.15 (m, 2H), 3.08-2.93 (m, 3H), 2.90-2.70 (m, 4H), 2.68-2.48 (m, 1H), 2.17-1.90 (m, 5H), 1.86-1.66 (m, 2H), 1.54-1.16 (m, 24H), 1.13-0.75 (m, 9H); MS(ESI$^+$) m/z 1050.8 (M+H)$^+$.

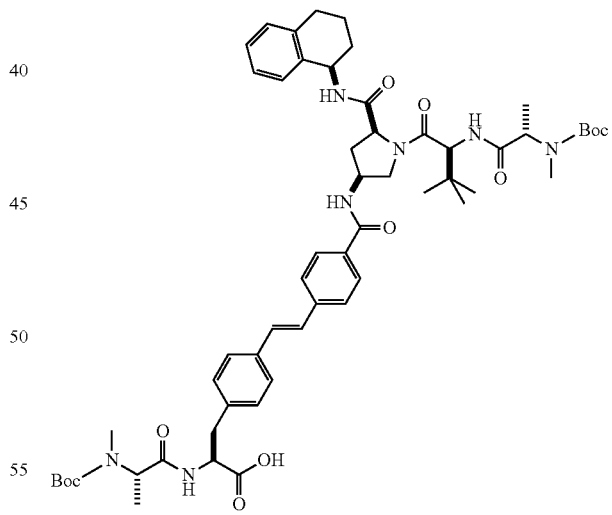

B) (S)-2-((S)-2-((tert-Butoxycarbonyl)(methyl)amino)propanamido)-3-(4-((E)-4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)styryl)phenyl)propanoic acid (S)-Methyl 2-((S)-2-((tert-butoxycarbonyl)(methyl)amino)propanamido)-3-(4-((E)-4-(((3S,5S)-1-((S)-2-((S)-2-

((tert-butoxycarbonyl)(methyl)amino)-propanamido)-3,3-dimethylbutanoyl)-5-(((R)-1,2,3,4-tetrahydronaphthalen-1-yl)carbamoyl)pyrrolidin-3-yl)carbamoyl)styryl)phenyl)propanoate (0.038 g, 0.036 mmol) was dissolved in MeOH (0.5 mL)/THF (0.5 mL) and the resulting solution was treated with 4N LiOH (0.090 mL, 0.18 mmol). The reaction mixture was stirred at rt for 1 h and quenched with 1N HCl. The resulting solution was extracted with CHCl₃ (3×). The combined organic extracts were dried, filtered and concentrated in vacuo to afford the product, which was used without further purification. $^1$H NMR (CD$_3$OD) δ 8.66 (d, J=8.8 Hz, 1H), 8.00-7.83 (m, 2H), 7.70 (s, 2H), 7.54 (d, J=8.1 Hz, 2H), 7.49-7.37 (m, 2H), 7.37-6.97 (m, 6H), 5.27-5.05 (m, 1H), 4.84-4.43 (m, 5H), 4.21-4.03 (m, 1H), 3.93 (dd, J=10.8, 3.5 Hz, 1H), 3.76 (ddd, J=6.7, 4.1, 2.6 Hz, 1H), 3.31-3.18 (m, 2H), 3.15-2.97 (m, 2H), 2.94-2.74 (m, 4H), 2.70-2.49 (m, 2H), 2.24-1.70 (m, 8H), 1.62-1.19 (m, 24H), 1.16-0.80 (m, 9H); MS(ESI⁺) m/z 1036.9 (M+H)⁺.

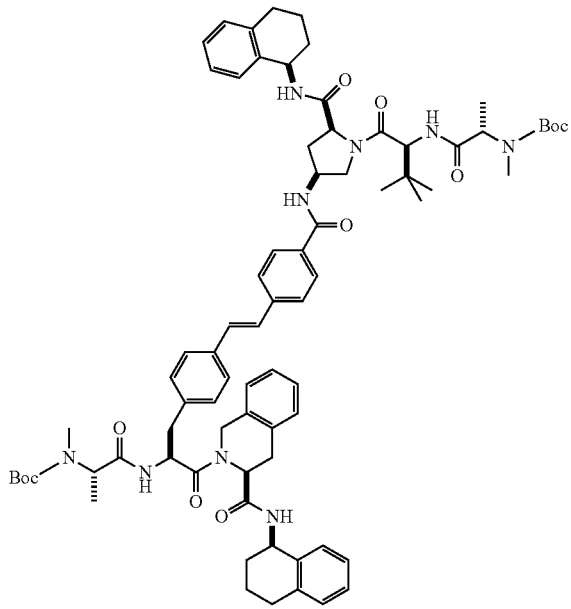

C) N-Boc-Precursor II (S)-2-((S)-2-((tert-Butoxycarbonyl)(methyl)amino)propanamido)-3-(4-((E)-4-(((3S,5S)-1-((S)-2-((S)-2-((tert-butoxycarbonyl)(methyl)amino)propanamido)-3,3-dimethylbutanoyl)-5-(((R)-1,2,3,4-tetrahydronaphthalen-1-yl)carbamoyl)pyrrolidin-3-yl)carbamoyl)styryl)phenyl)propanoic acid (0.031 g, 0.030 mmol), 3H-[1,2,3]triazolo[4,5-b]pyridin-3-ol (4.9 mg, 0.036 mmol) and N1-((ethylimino)methylene)-N3,N3-dimethylpropane-1,3-diamine hydrochloride (6.9 mg, 0.036 mmol) were stirred in DMF (1 mL) at 0° C. for 10 minutes. (S)—N—((R)-1,2,3,4-tetrahydronaphthalen-1-yl)-1,2,3,4-tetrahydroisoquinoline-3-carboxamide (9.2 mg, 0.030 mmol) followed by NMM (9.9 μl, 0.090 mmol) were added. The reaction mixture was stirred at 0° C., allowed to warm to rt and stirred for 1 h. The reaction mixture was filtered and the filtrate purified by C18 reverse phase preparative HPLC (eluting 81-90% aq. MeOH with 0.1% TFA over a 30 minute gradient). The appropriate fractions were isolated and concentrated in vacuo to remove the MeOH. The solution was then neutralized with sat. aq. NaHCO₃ solution and the resulting solution extracted with CHCl₃ (3×). The combined organic extracts were dried, filtered and concentrated in vacuo to afford the product. $^1$H NMR (CD$_3$OD) δ 7.99-7.80 (m, 2H), 7.69-7.55 (m, 2H), 7.54-7.36 (m, 3H), 7.34-7.18 (m, 3H), 7.17-6.90 (m, 12H), 5.13 (d, J=3.7 Hz, 2H), 4.79-4.72 (m, 2H), 4.69-4.47 (m, 4H), 4.15-4.01 (m, 2H), 3.97-3.77 (m, 2H), 3.40-3.33 (m, 1H), 3.27-2.91 (m, 5H), 2.87-2.52 (m, 9H), 2.25 (d, J=7.5 Hz, 11H), 1.55-1.15 (m, 25H), 1.08-0.75 (m, 9H); MS(ESI⁺) m/z 1324.1 (M+H)⁺.

D) (S)-2-((S)-3-(4-((E)-4-(((3S,5S)-1-((S)-3,3-Dimethyl-2-((S)-2-(methylamino)propanamido)butanoyl)-5-(((R)-1,2,3,4-tetrahydronaphthalen-1-yl)carbamoyl)pyrrolidin-3-yl)carbamoyl)styryl)phenyl)-2-((S)-2-(methylamino)propanoyl)-N—((R)-1,2,3,4-tetrahydronaphthalen-1-yl)-1,2,3,4-tetrahydroisoquinoline-3-carboxamide, 2 TFA N-Boc-Precursor II (0.015 g, 0.011 mmol) was dissolved in CHCl₃ (0.5 mL) at rt and the resulting solution was treated with hydrogen chloride (0.14 mL, 0.57 mmol, 4M in dioxane). The reaction mixture was stirred at rt for 1 h and concentrated in vacuo. The residue was purified by C18 reverse phase preparative HPLC (eluting 63-90% aq. MeOH over a 30 minute gradient). The appropriate fractions were isolated and concentrated in vacuo. The residue was dissolved in methanol and azeotroped (3×) with toluene. The solid was dissolved in aq. CH₃CN and freeze dried to afford the product as a white lyophilate. $^1$H NMR (CD$_3$OD) δ 8.42 (d, J=7.9 Hz, 1H), 7.96-7.84 (m, 2H), 7.75-7.61 (m, 3H), 7.57-7.36 (m, 4H), 7.31 (s, 13H), 5.45-5.32 (m, 1H), 5.21-5.09 (m, 1H), 5.01-4.89 (m, 1H), 4.77-4.73 (m, 1H), 4.66-4.52 (m, 3H), 4.22-4.10 (m, 1H), 4.03-3.81 (m, 4H), 3.76-3.65 (m, 1H), 3.30-3.01 (m, 4H), 2.93-2.50 (m, 11H), 2.17-1.54 (m, 12H), 1.52-1.44 (m, 6H), 1.40-1.31 (m, 2H), 1.08 (s, 9H); MS(ESI⁺) m/z 1124.1 (M+H)⁺.

Example 21

Evaluation of Biological Activity

Exemplary compounds were tested for inhibition of XIAP BIR2 and BIR3 and cIAP BIR3 activity. Experimental procedures and results are provided below.

A) XIAP-BIR2/SMAC Peptide AlphaScreen Assay

Assays were performed in white, flat-bottom, 384-well ProxiPlates (Perkin Elmer). The final assay volume was 10 μL prepared from additions of His-BIR2 (124-240/C202A/C213G), Biotinylated SMAC peptide, and test compounds in assay buffer consisting of 25 mM Hepes, 100 mM NaCl, 0.1% BSA, and 5 mM CaCl₂. The reaction was incubated at room temperature for 60 minutes. After 60 minutes, 2.5 μL of AlphaScreen detection reagent (Perkin Elmer) was added to the reaction mixture and incubated at room temperature in the dark for 120 minutes. The AlphaScreen signal generated by the reaction was detected on the Envision Plate Reader. Inhibition data were calculated from an AlphaScreen signal generated by the no protein control reactions for 100% inhibition and vehicle-only reactions for 0% inhibition. The final concentration of reagents in the assay was 50 nM His-BIR2 (124-240/C202A/C213G), 50 nM Biotinylated SMAC peptide, 4 µg/mL AlphaScreen detection reagents, and 0.5% DMSO. Dose response curves were generated to determine the concentration required for inhibiting 50% of the activity ($IC_{50}$). Compounds were dissolved at 10 mM in dimethylsulfoxide (DMSO) and evaluated at eleven concentrations. $IC_{50}$ values were derived by non-linear regression analysis.

B) XIAP-BIR3 SMAC Peptide Fluorescence Polarization Assay (FPA)

Assays were performed in black, flat-bottom, 384-well plates. The final assay volume was 50 µL prepared from additions of N-His-Tb-BIR3(241-356, XIAP), fluoresceinated modified SMAC peptide, and test compounds in assay buffer consisting of 20 mM Sodium Phosphate, 1 mM EDTA, 50 mM NaCl, and 0.05% PLURONIC® F68. The reaction was incubated at room temperature for 60 minutes and fluorescence polarization of the reaction was detected on the LJL Plate Reader Inhibition data were calculated from mP values generated by the no protein control reactions for 100% inhibition and vehicle-only reactions for 0% inhibition. The final concentration of reagents in the assay was 130 nM N-His-Tb-BIR3(241-356, XIAP), 1.4 nM fluoresceinated modified SMAC peptide, and 1% DMSO. Dose response curves were generated to determine the concentration required for inhibiting 50% of polarization activity ($IC_{50}$). Compounds were dissolved at 10 mM in dimethylsulfoxide (DMSO) and evaluated at eleven concentrations. $IC_{50}$ values were derived by non-linear regression analysis.

Results:

Results of the BIR2 and BIR3 assays are shown in Table 1 below.

"NT" means that the compound was not tested in the assay.

| Example No. | XIAP BIR3 | XIAP BIR2 |
|---|---|---|
| 1 | 0.14 | 1.11 |
| 2 | 0.06 | 0.49 |
| 3 | 0.08 | 0.46 |
| 4 | 0.06 | 0.22 |
| 5 | 0.16 | 1.84 |
| 6 | 0.14 | 1.19 |
| 7 | 0.14 | 1.10 |
| 8 | NT | NT |
| 9 | 0.06 | 0.72 |
| 10 | 0.13 | 0.48 |
| 11 | 0.25 | 1.70 |
| 12 | 0.06 | 0.62 |
| 13 | 0.15 | 2.43 |
| 14 | 0.08 | 1.14 |
| 15 | 0.23 | 2.00 |
| 16 | 0.07 | 2.11 |
| 17 | 0.27 | 2.44 |
| 18 | 0.22 | 2.68 |
| 19 | 0.21 | 2.21 |
| 20 | 0.18 | 1.25 |

What is claimed is:

1. A compound of Formula (I)

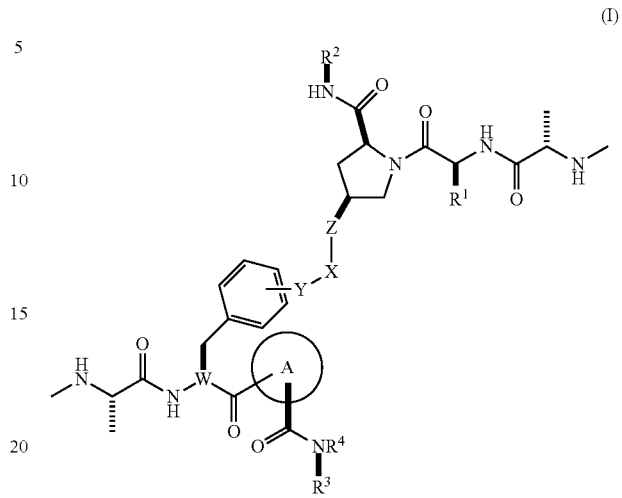

(I)

wherein
A is

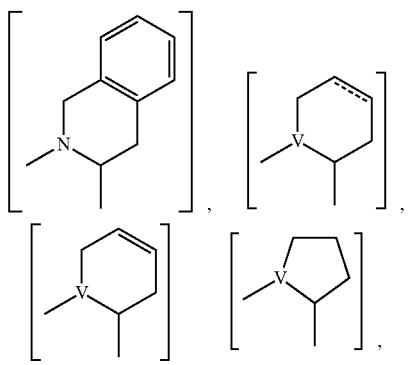

where the dotted line represents an optional double bond;
X is a —$(CR^7R^8)_m$—,

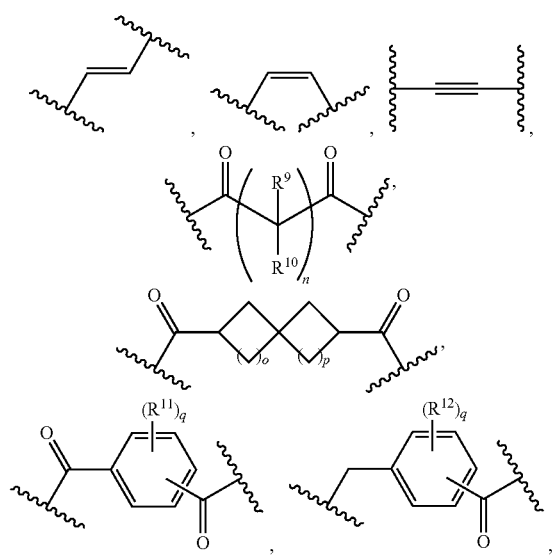

-continued

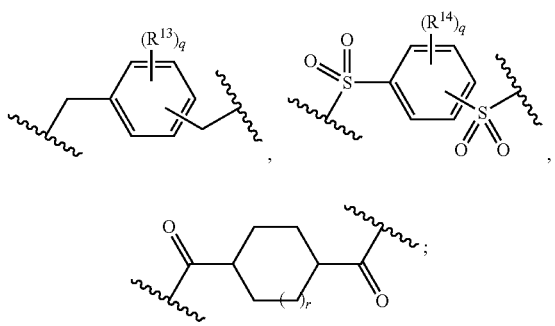

Y and Z are independently —O—, —NR⁶— or are absent;
V is —N— or —CH—;
W is —CH— or —N—;
R¹ is optionally substituted alkyl, optionally substituted cycloalkylalkyl, optionally substituted arylalkyl or optionally substituted aryl;
R² and R³ are independently optionally substituted alkyl, optionally substituted cycloalkyl, optionally substituted aryl, optionally substituted heteroaryl, optionally substituted heterocyclyl, optionally substituted arylalkyl, optionally substituted heteroarylalkyl or optionally substituted heterocycloalkyl, with the proviso that they cannot be naphthyl;
R⁴ is hydrogen or optionally substituted alkyl;
R⁶ is hydrogen or optionally substituted alkyl, optionally substituted cycloalkyl;
R⁷ and R⁸ are independently hydrogen, halogen or optionally substituted alkyl;
R⁹ and R¹⁰ are independently hydrogen, halogen or optionally substituted alkyl, or R⁹ and R¹⁰ can be taken together to form a ring;
R¹¹, R¹², R¹³ and R¹⁴ are independently hydrogen, halogen, optionally substituted alkyl or OR¹⁵;
R¹⁵ is hydrogen, optionally substituted alkyl or optionally substituted cycloalkyl;
m and n are independently 0, 1, 2, 3, or 4;
o and p are independently 0, 1, 2 or 3;
q is 0, 1, 2, 3, or 4;
r is 0 or 1;
or a pharmaceutically acceptable salt, tautomer or stereoisomer thereof.

2. The compound according to claim 1 wherein:
R¹ is optionally substituted alkyl;
R² and R³ are independently optionally substituted alkyl, optionally substituted aryl or optionally substituted arylalkyl; with the proviso that they cannot be naphthyl;
R⁴ is hydrogen or alkyl;
R⁶ is hydrogen or optionally substituted alkyl;
R⁷ and R⁸ are independently alkyl;
or a pharmaceutically acceptable salt, tautomer or stereoisomer thereof.

3. The compound according to claim 2 wherein
R¹ is alkyl;
R² and R³ are independently aryl, with the proviso that they cannot be naphthyl;
R⁴ is hydrogen or methyl;
or a pharmaceutically acceptable salt, tautomer or stereoisomer thereof.

4. The compound according to claim 3 wherein
R¹ is t-butyl;
R² and R³ are independently 1,2,3,4-tetrahydronaphthalene;
or a pharmaceutically acceptable salt, tautomer or stereoisomer thereof.

5. A pharmaceutical composition comprising a compound of claim 1 and a pharmaceutically acceptable carrier.

6. A compound according to claim 1 selected from the following
(S)-1-((S)-3-(4-((4-(((3S,5S)-1-((S)-3,3-Dimethyl-2-((S)-2-(methylamino) propanamido)butanoyl)-5-(((R)-1,2,3,4-tetrahydronaphthalen-1-yl)carbamoyl) pyrrolidin-3-yl)carbamoyl)benzyl)oxy) phenyl)-2-((S)-2-(methylamino) propanoyl)-N-((R)-1,2,3,4-tetrahydronaphthalen-1-yl)-1,2,3,6-tetrahydropyridine-2-carboxamide,
(2S,4S)-1-((S)-3,3-Dimethyl-2-((S)-2-(methylamino)propanamido)butanoyl)-4-(4-((4-((S)-2-((S)-2-(methylamino)propanamido)-3-oxo-3-((1R,6R)-6-(((R)-1,2,3,4-tetrahydronaphthalen-1-yl)carbamoyl)cyclohex-3-en-1-yl)propyl)phenoxy)methyl)benzamido)-N-((R)-1,2,3,4-tetrahydronaphthalen-1-yl)pyrrolidine-2-carboxamide,
(2S,4S)-1-((S)-3,3-Dimethyl-2-((S)-2-(methylamino)propanamido)butanoyl)-4-(4-((4-((S)-2-((S)-2-(methylamino)propanamido)-3-oxo-3-((1S,6S)-6-(((R)-1,2,3,4-tetrahydronaphthalen-1-yl)carbamoyl)cyclohex-3-en-1-yl)propyl)phenoxy)methyl)benzamido)-N-((R)-1,2,3,4-tetrahydronaphthalen-1-yl)pyrrolidine-2-carboxamide,
or a pharmaceutically acceptable salt, tautomer or stereoisomer thereof.

* * * * *